(12) United States Patent
Sena-Esteves et al.

(10) Patent No.: US 6,677,155 B1
(45) Date of Patent: Jan. 13, 2004

(54) TRIPLE HYBRID AMPLICON VECTOR SYSTEMS TO GENERATE RETROVIRAL PACKAGING LINES

(75) Inventors: Miguel Sena-Esteves, Philadelphia, PA (US); Xandra O Breakefield, Newton, MA (US); Yoshinaga Saeki, Toyama (JP)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/557,910

(22) Filed: Apr. 21, 2000

Related U.S. Application Data
(60) Provisional application No. 60/130,551, filed on Apr. 22, 1999.

(51) Int. Cl.$^7$ ..................... C12N 15/63; C12N 15/00; A01N 43/04; A61K 31/70
(52) U.S. Cl. ................. 435/456; 435/320.1; 435/457; 435/69.1; 435/325; 514/44; 424/93.21
(58) Field of Search ............................ 435/320.1, 69.1, 435/325, 456, 457; 514/44; 424/93.1, 93.21

(56) References Cited

U.S. PATENT DOCUMENTS

| | | | |
|---|---|---|---|
| 5,529,774 A | 6/1996 | Barba et al. | 424/93.21 |
| 5,601,818 A | 2/1997 | Freeman et al. | 424/93.21 |
| 5,631,236 A | 5/1997 | Woo et al. | 514/44 |
| 5,670,488 A | 9/1997 | Gregory et al. | 514/93.2 |

(List continued on next page.)

FOREIGN PATENT DOCUMENTS

| | | | |
|---|---|---|---|
| WO | 95/06486 | | 3/1995 |
| WO | WO-9604789 | * | 2/1996 |

(List continued on next page.)

OTHER PUBLICATIONS

Palu et. al.; In pursuit of new development for gene therapy of human diseases, 1999, Journal of Biotechnology 68:1–13.*
Reynolds et al.; Chimeric viral vectors– the best of both worlds, 1999, Molecular Medicine Today: 25–31.*
Aghi et. al.; Synergistic Anticancer Effects of Ganciclovir/ Thymidine Kinase and 5–Fluorocytosine / Cytosine Deaminase Gene Therapies, 1998, Journal of the National Cancer Institute, vol. 90, No. 5:: 370–380.*
Feng, M., et al., "Stable in vivo gene transduction via a novel adenoviral/retroviral chimeric vector," *Nature Biotechnol.* 15:866–870 (1997).
Johnston, K.M., et al., "HSV/AAV Hybrid Amplican Vectors Extend Transgene Expression in Human Glioma Cells," *Hum. Gene Ther.* 8:359–370 (1997).
Aboody–Guterman, K.S. et al., "Green Fluorescent Protein as a Reporter for Retrovirus and Helper Virus–free HSV–Amplicon vector–mediated Gene Transfer into Neural Cells in Culture and in vivo," *Neuroreport* 8:3801–3808 (1997).

Bender, M.A., et al., "Evidence that the Packaging Signal of moloney Murine Leukemia Virus Extends into the *gag* Region," *J. Virol.* 61:1639–1646 (1987).
Bilbao, G. et al., "Adenoviral/retroviral Vector Chimeras: a Novel Strategy to Achieve High–efficiency stable Transduction in vivo," *FASEB J.* 11:624–634 (1997).
Boviatsis, E.J., et al., "Long–Term Survival of Rats Harboring Brain Neoplasms Treated with Ganciclovir and a Herpes Simplex Virus Vector That Retains an Intact Thymidine Kinase Gene," *Cancer Res.* 54:5745–5751 (1994).
Breakefield, x.o. et al., "Herpes Simplex Virus Vectors for Tumor Therapy," *The Internet Book of Gene Therapy: Cancer Gene Therapeutics*, R.E. Sobol and K.J. Scanton, eds. Appelton and Lange, Stamford Ct, pp. 41–56 (1995).
Burns, J.C., et al., "Vesicular stomatitus virus G glycoprotein pseudotyped retroviral vectors: Concentration to very high titer and efficient gene transfer into mammalian and nonmammalian cells," *Proc. Natl. Acad. Sci. USA* 90:8033–8037 (1993).
Chakraborty, A.K., et al., "Transmission of endogenous VL30 retrotransposons by helper cells used in gene therapy," *Cancer Gene Ther.* 1:113–118 (1994).
Chase, M., et al., "An oncolytic viral mutant that delivers the CYP2B1 transgene and augments cyclophosphamide chemotherapy," *TransNature Biotechnol.* 16:444–448 (1998).
Chattapadhyay, S.K., et al., "Genomes of Murine Leukemia Viruses Isolated from Wild Mice," *J. Virol.* 39:777–791 (1981).
Chen L., and Waxman, D.J., "Intratumoral Activation and Enhanced Chemotherapeutic Effect of Oxazaphosphorines following cytochrome P–450 Gene Transfer: Development of a Combined Chemotherapy/Cancer Gene Therapy Strategy," *Cancer Research* 55:581–589 (1995).
Coffin, J.M., "Retroviridae: The Viruses and Their Replication," in B.N. Fields et al., (ed.) *Fields Virology*, Raven Publishers, Philadelphia (1996).
Cosset, F.L., et al., "High–Titer Packaging Cells Producing Recombinant Retroviruses Resistant to Human Serum," *J. Virol.* 69:7430–7436 (1995).

(List continued on next page.)

*Primary Examiner*—Deborah Crouch
*Assistant Examiner*—Joseph Woitach
(74) *Attorney, Agent, or Firm*—Sterne, Kessler, Goldstein & Fox P.L.L.C.

(57) ABSTRACT

The present invention relates to a triple hybrid vector amplicon system comprising genetic elements derived from Herpes Simplex Virus (HSV), Epstein-Barr Virus (EBV) or Adeno-Associated Virus (AAV), and a retrovirus. The vector was developed to stably transform cells, both in culture or in vivo, into retrovirus packaging cells in a single step. This step can be accomplished both by transfection using liposomes, electroporation, calcium phosphate, or any other methodology used to transfer naked or complexed DNA into cells or by infection when the vector is packaged as an amplicon vector in HSV virions.

30 Claims, 22 Drawing Sheets

U.S. PATENT DOCUMENTS

| | | | |
|---|---|---|---|
| 5,688,773 A | 11/1997 | Chiocca et al. | 514/44 |
| 5,691,177 A | 11/1997 | Guber et al. | 435/172.3 |
| 5,741,486 A | 4/1998 | Pathak et al. | 424/93.21 |
| 5,756,283 A | 5/1998 | Wilson et al. | 435/5 |
| 5,763,217 A | 6/1998 | Cynader et al. | 435/69.1 |
| 5,763,242 A | 6/1998 | Zhang et al. | 435/172.3 |
| 5,830,725 A | 11/1998 | Nolan et al. | 435/172.3 |
| 5,830,727 A | 11/1998 | Wang et al. | 435/172.3 |

FOREIGN PATENT DOCUMENTS

| | | |
|---|---|---|
| WO | 97/05263 | 2/1997 |
| WO | Wo 98/21345 | 5/1998 |

OTHER PUBLICATIONS

Constantini, L.C., et al., "Gene transfer to the Nigrostriatal System by Hybrid Herpes Himplex Virus/Adeno–Associated Virus Amplicon Vectors," *Human Gene Ther.* 10:2481–94 (Oct. 1999).

Cukor, et al., "Biology of Adeno–Associated Virus," *The Pavoviruses*, ed., K.I. Berns, Plenum, N.Y., pp. 33–36 (1984).

Culver, K.W., et al., "In Vivo Gene Transfer with Retroviral Vector–Producer Cells for Treatment of Experimental Brain Tumors," *Science* 256:1550–1552 (1992).

Cunningham, C., and Davison, A.J., "A Cosmid–Based System for Constructing Mutants of Herpes Simplex Virus Type 1, " *Virology* 197: 116–124 (1993).

Danos, O., and Mulligan, R.C., "Safe and efficient generation of recombinant retroviruses with amphotropic and ecotropic host ranges," *Proc. Natl. Acad. Sci. USA* 85:6460–6464 (1988).

Duan, D., et al., "Formation of Adeno–Associated Virus Circular Genomes Is Differently Regulated by Adenovirus E4 ORF6 and E2a Gene Expression," *J. Virol.* 73:161–169 (1999).

Duisit, G., et al., "Functional Characterization of Adenoviral/Retroviral Chimeric Vectors and Their Use for Efficient Screening of Retroviral Producer Cell Lines," *Human Gene Ther.* 10:189–200 (1996).

During, H.J., et al., "Long–Term Behavioral Recovery in Parkinsonian Rats by an HSV Vector Expressing Tyrosine Hydroxylase," *Science* 266, 1399–1403 (1994).

Flotte, T.R. and Carter, B.J., "Adeno–associated virus for gene therapy," *Gene Ther.* 2:357–362 (1995).

Fraefel, C., et al., "Helper Virus–Free Transfer of Herpes Simplex Virus Type 1 Plasmid Vectors into Neural Cells," *J. Virol.* 70:7190–7197 (1996).

Fraefel, C. et al., "Gene Transfer into Hepatocytes Mediated by Helper Virus–Free HSV/AAV Hybrid Vectors," *Mol. Med.* 3:813–825 (1997).

Fraefel, C., et al., "HSV–1 Amplicon" in *Gene Therapy for Neurological Disorders and Brain Tumors*, E.A. Choices and X.O. Breakfield, eds. Humana Press, Totowa, pp. 63–82 (1998).

Freeman, S.M., et al., "In Situ Use of Suicide Genes for Cancer Therapy," *Semin. Oncol.* 23:31–45 (1996).

Geller, A.I., et al., "An Efficient Deletion Mutant Packaging System for Defective Herpes Simplex Virus Vectors: Potential Applications to Human Gene Therapy and Neuronal Physiology," *Proc. Natl. Acad. Sci USA* 87:8950–8954 (1990).

Geller, A.I. and Breakfield, X.O., "A Defective HSV–1 Vector Expresses *Escherichia coli* β–Galactosidase in Cultered Peripheral Neurons," *Science* 241: 1667–1669 (1988).

Glorioso, J.C. et al., "Herpes Simplex Virus as a Gene–Delivery Vector for the Central Nervous System," in *Viral Vectors: Gene Therapy and Neuroscience Applications*, M.G. Kaplitt and A.D. Loewy eds., Academic Press, New York, pp. 1–23 (1995).

Goldman, M.J., et al., "Lentiviral Vectors for Gene Therapy of Cystic Fibrosis," *Human Gene Ther.* 8:2261–2268 (1997).

Heise, C. et al., "Onyx–D15, an E1B gene–attenuated adenovirus, causes tumor–specific cytolysis and antitumoral efficacy that can be augmented by standard chemotherapeutic agents," *Nat. Med.* 3:639–645 (1997).

Isacson, O. and Breakefield, X.O., "Benefits and risks of hosting animal cells in the human brain," *Nature Med.* 3:964–969 (1997).

Jacoby, D.R. et al., "Hybrid vectors: a new generation of virus–based vectors designed to control cellular fate of delivered genes," *Gene Therapy* 4:1281–1283 (1997).

Savard, N., et al., "Defective Herpes Simplex Virus Type 1 Vectors Harboring gag, pol, and env Genes Can Be Used To Rescue Defective Retrovirus Vectors," *J. Virol.* 71:4111–4117 (1997).

Kafri, T., et al., "Sustained expression of genes delivered directly into liver and muscle by lentiviral vectors," *Nat. Genet.* 17:314–317 (1997).

Karacostas, V., et al., "Overexpression of HIV–1 Gag–Pol Polyprotein Results in Intracellular Activation of HIV–1 Protease and Inhibition of Assembly and Budding of Virus––like Particles," *J. Virol.* 193:661–671 (1993).

Wang, S. and Vos, J.M., "A Hybrid Herpesvirus Infectious Vector Based on Epstein–Barr Virus and Herpes Simplex Virus Type 1 for Gene Transfer into Human Cells In Vitro and In Vivo," *J. Virol.* 70:8422–8430 (1996).

Kasahara, N., et al., "Tissue–Specific Targeting of Retroviral Vectors Through Ligand–Receptor Interactions," *Science* 266:1373–1376 (1994).

Kim, S.H., et al., "Construction of Retroviral Vectors with Improved Safety, Gene Expression, and Versatility," *J. Virol.* 72:994–1004 (1998).

Kotin, R.M., et al., "Site–specific integration by adeno–associated virus," *Proc. Natl. Acad. Sci. USA* 87:2211–2215 (1990).

Kramm, C.M. et al., "Gene Therapy for Brain Tumors," *Brain Pathology* 5:345–381 (1995).

Lal, B., et al., "Endothelial cell implantation and survival within experimental gliomas," *Proc. Natl. Acad. Sci. USA* 91:9695–9699 (1994).

Landau, N.R., and Littman, D.R., "Packaring System for Rapid Production of Murine Leukemia Virus vectors with Variable Tropism," *J. Virol.* 66:5510–5113 (1992).

Laquerre, S., et al., "Recombinant Herpes Simplex Virus Type 1 Engineered for Targeted Binding to Erythropoietin Receptor–Bearing Cells," *J. Virol.* 72:9683–9697 (1998).

Latchman, D.S., "Herpes–Simplex Virus Vectors for Gene Therapy," *Mol. Biotechnol.* 2:179–195 (1994).

Lebkowski, J.S., et al., "Adeno–Associated Virus: a Vector System for Efficient Introduction and Integration of DNA into a Variety of Mammalian Cell Types," *Mol. Cell. Biol.* 8:3988–3996 (1988).

Fisher, L.J. and Ray, J., "In vivo and ex vivo transfer to the brain," *Curr. Opin. Neurobiol.* 4:735–741 (1994).

Reynolds, P.N., et al., "Chimeric viral vectors—the best of both worlds?" *Mol. Med. Today* 5:25–31 (Jan. 1999).

Li, K.J., and Garoff, H., "Production of infectious recombinant Moloney murine leukemia virus particles in BHK cells using Semliki Forest virus–derived RNA expression vectors," *Proc. Natl. Acad. Sci. USA* 93:11658–11663 (1996).

Lim, F., et al., "Generation of High–Titer Defective HSV–1 Vectors using an IE 2 Deletion Mutant and Quantative Study of Expression in Cultered Cortical Cells," *BioTechniques 20*: 458–469 (1996).

Lin, X., "Construction of new retrovival producer cells from adenoviral and retroviral vectors," *Gene Ther.* 5:1251–1258 (1998).

Sena–Esteves, M., et al., "Single–Step Conversion of Cells to Retrovirus Vector Producers with Herpes Simplex Virus–Epstein–Barr Virus Hybrid Amplicons," *J. Virol.* 73:10426–10439, American Society for Microbiology (Dec. 1999).

Mann, R., et al., "Construction of a Retrovirus Packaging Mutant and Its Use to Produce Helper–Free Defective Retrovirus," *Cell* 33:153–159 (1983).

Morgenstern, J.P., and Land, J., "Advanced mammalian gene transfer: high titre retroviral vectors with multiple drug selection markers and a complementary helper–free packaging cell line," *Nucleic Acids Res.* 18:3587–3596 (1990).

Mullen, C.A., et al., "Transfer of the bacterial gene for cytosine deaminase to mammalian cells confers lethal sensitivity to 5–fluorocytosinr: A negative selection system," *Proc. Natl. Acad. Sci. USA* 89:33–37 (1992).

Mullen C.A., et al., "Tumors Expressing the Cytosine Deaminase Suicide Gene Can Be Eliminated in Vivo with 5–Fluorocytisine and Induce Protectivity Immunity to Wild Type Tumor," *Cancer Res.* 54:1503–1506 (1994).

Muzyczka, N., "Use of Adeno–Associated Virus as a General Transduction Vector for Mammalian Cells," *Curr Top Microbiol. Immunol.* 158:97–129 (1992).

Naviaux, R.K., et al., "The pCL Vector System: Rapid Production of Helper–Free, High–Titer, Recombinant Retroviruses," *J. Virol.* 70:5701–5705 (1996).

Nakanishi, M., "Gene Introduction into Animal Tissues," *Crit. Rev. Therapeu. Drug Carrier Systems* 12:263–310 (1995).

Naldini, L., "Lentiviruses as gene transfer agents for delivery to non–dividing cells," *Curr. Opin. Biotechnol.* 9:457–463 (1998).

Naldini, L., et al., "In Vivo Gene Delivery and Stable Transduction of Nondividing Cells by a Lentiviral Vector," *Science* 272:263–267 (1996).

Nelson, D.R., et al., "The P450 Superfamily: Update on new Sequences, Gene Mapping, Accesion Numbers, Early Trivial Names of Enzymes, and Nomenclature," *DNA and Cell Biology* 12:1–51 (1993).

Ni, T.H., et al., "Cellular Proteins Required for Adeno–Associated Virus DNA Replication in the Absence of Adenovirus Coinfection," *J. Virol.* 72:2777–2787 (1998).

Noguiez–Hellin, P., et al., "Plasmoviruses: Nonviral/viral vectors for gene therapy," *Proc. Natl. Acad. Sci. USA* 93:4175–4180 (1996).

Ostrove, J.M., et al., "Inhibition of Adenovirus–Transformed Cell Oncogenicity by Adeno–Associated Virus," *Virology* 113:521–533 (1981).

Palombo, F., et al., "Site–Specific Integration in Mammalian Cells Mediated by a New Hybrid Baciovirus–Adeno–Associated Virus Vector," *J. Virol.* 72:5025–5034 (1998).

Patience, C., et al., "Packaging of Endogenous Retroviral Sequences in Retroviral Vectors Produced by Murine and Human Packaging Cells," *J. Virol.* 72:2671–2676 (1998).

Pear, W.S., et al., "Production of high–titer helper–free retroviruses by transient transfection," *Proc. Natl. Acad. Sci USA* 90:8392–8396 (1993).

Preiss, A., et al., "Molecular genetics of Krüppel, a gene required for segmentation of the *Drosophila* embryo," *Nature* 313:27–32 (1985).

Puumalainen, A.M., et al., "β–Galactosidase Gene Transfer to human Malignant Glioma In Vivo Using Replication–Deficient Retroviruses and Adenoviruses," *Human Gene Ther.* 9:1769–1774 (1998).

Ram, Z. et al., "Therapy of malignant brain tumors by intratumoral implantation of retroviral vector–producing cells," *Nature Med.* 182:1354–1361 (1997).

Recchia, A., et al., "Site–specific integration mediated by a hybrid adenovirus/adeno–associated virus vector," *Proc. Natl. Acad. Sci. USA* 96:2615–2620 (1998).

Robbins, P.D., et al., "Viral vectors for gene therapy," *Trends Biotechnol.* 16:35–40 (1998).

Seeki, Y., et al., Herpes Simplex Virus Type 1 DNA Amplified Bacterial Artificial Chromosome in *Escherichia coli*: Rescue of Replication–Competent Virus Progeny and Packaging of Amplicon Vectors, *Human Gene Ther.* 9:2787–2794 (1998).

Samulski, R.J., et al., "Targeted integration of adeno–associated virus (AAV) into human chromosome 19," *EMBO J.* 10:3941–3950 (1991).

Soneoka, Y., et al., "A transient three–plasmid expression system for the production of high titer retroviral vectors," *Nucleic Acids Res.* 23:628–633 (1995).

Spaete, R.R. and Frenke, N., "The Herpes Simplex Virus Amplicon: A new Eurcaryotic Defective–Virus Cloning–Amplifying Vector," *Cell* 30:295–304 (1982).

Tamiya, T., et al., "Transgene inheritance and retroviral infection contribute to the efficiency of gene expression in solid tumors inoculated with retroviral vector producer cells," *Gene Ther.* 2:531–538 (1995).

Tamura, M., et al., "Targeted Killing of Migrating Glioma Cells by Injection of HTK–Modified Glioma Cells," *Human Gene Ther.* 8:381–391 (1997).

Vile, R.G., et al., "Retroviruses as vectors," *Br. Med. Bull.* 51:12–30 (1995).

Watson, J.D. et al, "Working Toward Human Gene Therapy," Ch 28, *Recombinant DNA* , 2nd ed. New York, Scientific American Books, pp. 567–581 (1992).

Wei, M.X., et al., "Experimental tumor therapy in mice using the cyclophosphamide–activating cytochrome P450 2B1 gene," *Hum. Gene. Ther.* 5:969–978 (1994).

Wendelberg, B.J., et al., "An enhanced EBNA1 variant with reduced 1R3 domain for long–term episomal maintenance and transgene expression of oriP–based plasmids in human cells," *Gene Ther.* 5:1389–1399 (1998).

Wilson, J.M., "Vectors–shuttle vehicles for gene therapy," *Clin. Exp. Immunol.* 107(Suppl 1):31–32 (1997).

Wolfe, J.H., et al., Herpesvirus Vector Gene Transfer and Expression of β-glucuronidase in the Central Nervous System of MPS VII Mice, *Nat. Genet. 1*:379–384 (1992).

Yamada, M., et al., "Migration of Genetically Labeled Glioma Cells After Implantation Into Murine Brain," *J. Neurosci. Res. 38*:415–423 (1994).

Yates, J.L., et al., "Stable replication of plasmids deriveds from Epstein–Barr virus in various mammalian cells," *Nature 313*:812–815 (1985).

Yoshida, Y., et al., "VSV–G–Pseudotyped Retroviral Packaging through Adenovirus–Mediated Inducible Gene Expression," *Biochem. Biophys. Res. Comm. 232*:379–382 (1997).

Zhang, J., et al., "Vectors for Cancer Gene Therapy," *Cancer Metastasis Rev. 16*:385–401 (1996).

\* cited by examiner

A

HyRMOVAmpho
(18.7 kb)

B

HyBPlacZ
(14.8 kb)

A

B

TRIPLE HYBRID AMPLICON VECTOR SYSTEMS TO GENERATE RETROVIRAL PACKAGING LINES

CROSS-REFERENCE TO RELATED APPLICATIONS

This application claims the benefit of U.S. Provisional Application No. 60/130,551, filed on Apr. 22, 1999, which is herein incorporated by reference.

STATEMENT AS TO THE RIGHTS TO INVENTIONS MADE UNDER FEDERALLY-SPONSORED RESEARCH AND DEVELOPMENT

Part of the work performed during development of this invention utilized U.S. Government funds under grant numbers NINDS NS24279, awarded by the National Institutes of Health, and NCI CA 69246, awarded by the National Cancer Institute. The U.S. Government has certain rights in this invention.

BACKGROUND OF THE INVENTION

1. Field of the Invention

The present invention relates to triple hybrid amplicon vector constructs comprising elements from Herpes Simplex virus (HSV), Epstein-Barr virus (EBV) or Adeno-Associated Virus (AAV), and retrovirus. The hybrid amplicon vectors of the present invention are capable of transforming dividing and non-dividing cells into retroviral packaging cells in a single step, which can be mediated in vitro or in vivo. Because the vector system of the present invention can convert cells in vivo to packaging cells, it creates, in vivo, a self-sustained gene delivery system.

2. Related Art

The terms "gene transfer" and "gene therapy" have been used to describe a variety of methods for delivering genetic material to a cell using viral or non-viral based vector systems. Substantial attention has been given to human gene therapy. The transfer of genetic material to a cell may one day become one of the most important forms of medicine. A variety of public and private institutions now participate in research and development related to the use of genetic material in therapeutic applications. Hundreds of human gene transfer protocols are being conducted at any given time with the approval of the Recombinant DNA Advisory Committee (RAC) and the National Institutes of Health (NIH). Most of these protocols focus on therapy, while others involve marking and non-therapeutic applications. The therapeutic protocols are primarily concerned with infectious diseases, monogenic diseases, and cancer. Gene-based therapies are now expanding into fields such as cardiovascular disease, autoimmune disease, and neurodegenerative disease. The availability of an efficient gene delivery and expression system is essential to the success and efficacy of gene-based therapy.

One method of delivering a gene of interest to a target cell of interest is by using a viral-based vector. Techniques for the formation of vectors or virions are generally described in "Working Toward Human Gene Therapy," Chapter 28 in *Recombinant DNA*, 2nd Ed., Watson, J. D. et al., eds., New York: Scientific American Books, pp. 567–581 (1992). An overview of viral vectors or virions that have been used in gene therapy can be found in Wilson, J. M., Clin. *Exp. Immunol.* 107(Suppl. 1):31–32 (1997), as well as Nakanishi, M., *Crit. Rev. Therapeu. Drug Carrier Systems* 12:263–310 (1995); Robbins, P. D., et al., *Trends Biotechnol.* 16:35–40 (1998); Zhang, J., et al., *Cancer Metastasis Rev.* 15:385–401 (1996); and Kramm, C. M., et al., *Brain Pathology* 5:345–381 (1995). Such vectors may be derived from viruses that contain RNA (Vile, R. G., et al., *Br. Med Bull.* 51:12–30 (1995)) or DNA (Ali M., et al., *Gene Ther.* 1:367–384 (1994)).

Specific examples of viral vector systems that have been utilized include: retroviruses (Vile, R. G., supra; U.S. Pat. Nos. 5,741,486 and 5,763,242); adenoviruses (Brody, S. L., et al., *Ann. N.Y. Acad. Sci.* 716: 90–101 (1994); Heise, C. et al., *Nat. Med.* 3:639–645 (1997)); adenoviral/retroviral chimeras (Bilbao, G., et al., *FASEB J.* 11:624–634 (1997); Feng, M., et al., *Nat. Biotechnol.* 15:866–870 (1997)); adeno-associated viruses (Flotte, T. R. and Carter, B. J., *Gene Ther.* 2:357–362 (1995); U.S. Pat. No. 5,756,283); herpes simplex virus I or II (Latchman, D. S., *Mol. Biotechnol.* 2:179–195 (1994); U.S. Pat. No. 5,763,217; Chase, M., et al., *Nature Biotechnol.* 16:444–448 (1998)); parvovirus (Shaughnessy, E., et al., *Semin Oncol.* 23:159–171 (1996)); reticuloendotheliosis virus (Donburg, R., *Gene Therap.* 2:301–310 (1995)). Other viruses that can be used as vectors for gene delivery include poliovirus, papillomavirus, vaccinia virus, lentivirus, as well as hybrid or chimeric vectors incorporating favorable aspects of two or more viruses (Nakanishi, M. *Crit. Rev. Therapeu. Drug Carrier Systems* 12:263–310 (1995); Zhang, J., e al., *Cancer Metastasis Rev.* 15:385–401 (1996); Jacoby, D. R., et al., *Gene Therapy* 4:1281–1283 (1997)). Guidance in the construction of gene therapy vectors and the introduction thereof into affected animals for therapeutic purposes may be obtained in the above-referenced publications, as well as U.S. Pat. Nos. 5,631,236, 5,688,773, 5,691,177, 5,670,488, 5,529,774, 5,601,818, and WO 95/06486.

The viral vectors mentioned above each have advantages and disadvantages. For example, retroviruses have the ability to infect cells and have their genetic material integrated into the host cell with high efficiency. The development of a helper virus free packaging system for retrovirus vectors was a key innovation in the development of this vector system for human gene therapy. Retroviral helper virus free packaging systems generally employ the creation of a stable producer cell line that expresses a selected vector. The relatively small size of the retroviral genome (approximately 11 kb), and the ability to express viral genes without killing cells, allows for the production of a packaging cell line that synthesizes all the proteins required for viral assembly. Producer lines are made by introducing the retroviral vector into such a packaging cell line.

On a down side, however, numerous difficulties with retroviruses have been reported. For example, most retroviral vectors are not capable of gene transfer to postmitotic (nondividing) cells and thus are not applicable to the nervous system because most of the cells in the adult nervous system, especially neurons, are quiescent or postmitotic. In addition, outbreaks of wild-type virus from recombinant virus-producing cell lines have also been reported, with the vector itself causing a disease.

Difficulties have been noted with other viral vectors as well. Adenovirus vectors can only support limited long-term (2 months) gene expression, they appear to be gradually lost from neural cells, and moreover, they can cause both cytopathic effects and an immune response (Le Gal La Salle, G., et al., *Science* 259:988–990 (1993); Davidson et al., *Nat. Genet.* 3:219–223 (1993); Yang, Y., et al., *J. Virol.* 69:2004–2015 (1995)). Adeno-associated virus vectors cause minimal cytopathic effects and can support at least some gene expression for up to 4 months, but gene transfer is inefficient and these vectors can accept only about 4 kb of foreign DNA (Kaplitt, M. G., et al., *Nat. Genet.* 8:148–154 (1994)).

Vectors based on herpes simplex virus (HSV), and especially HSV-1, have shown promise as potent gene delivery vehicles for several reasons: the virus has a very large genome and thus can accommodate large amounts of foreign DNA (greater than 30 kb), the virus can persist long-term in cells, and can efficiently infect many different cell types, including post-mitotic neural cells (Breakefield, X. O., et al., "Herpes Simplex Virus Vectors for Tumor Therapy," in *The Internet Book of Gene Therapy: Cancer Gene Therapeutics*, R. E. Sobol and K. J. Scanlon, eds., Appleton and Lange, Stamford, Conn., pp. 41–56 (1995); Glorioso, J. C., et al., "Herpes Simplex Virus as a Gene-Delivery Vector for the Central Nervous System," in Viral Vectors: *Gene Therapy and Neuroscience Applications*, M. G. Kaplitt and A. D. Loewy, eds., Academic Press, New York, pp. 1–23 (1995)).

Two types of HSV-1 vector systems are known: recombinant and amplicon. Recombinant HSV-1 vectors (Wolfe, J. H. et al., *Nat. Genet.* 1:379–384 (1992)) are created by inserting genes of interest directly into the 152 kb viral genome, thereby mutating one or more of the approximately 80 viral genes, and concomitantly reducing cytotoxicity.

In contrast, HSV-1 amplicons are bacterial plasmids containing only about 1% of the 152 kb HSV-1 genome. They are packaged into HSV-1 particles (virions) using HSV-1 helper virus. HSV-1 amplicons contain: (i) a transgene cassette with a gene of interest; (ii) sequences that allow plasmid propagation in *E. coli*, such as the origin of DNA replication colE1 and the ampicillin resistance gene; and (iii) non-coding elements of the HSV-1 genome, in particular an origin of DNA replication (ori) and a DNA cleavage/packaging signal (pac), to support replication and subsequent packaging of the amplicon DNA into virions in the presence of helper functions (Spaete, R. R. and Frenkel, N., *Cell* 30:295–304 (1982)). HSV amplicon vectors are one of the most versatile, most efficient, and least toxic, and have the largest transgene capacity of the currently available virus vectors. HSV-1 amplicon vectors can support some gene expression for up to one year in non-dividing cells (During, M. J., et al., *Science* 266:1399–1403 (1994)).

Because HSV-1 encodes many toxic functions, improvements on the amplicon system have been targeted at reducing the risk associated with the helper virus. First, replication-competent HSV-1, initially used as helper virus, was replaced by a temperature-sensitive (ts) mutant of HSV-1 (HSV-1 tsK; Preston, C., *J. Virol.* 29:257–284 (1979)). This mutant encodes a temperature-sensitive form of the essential HSV-1 infected cell protein (ICP) 4, allowing HSV-1 replication to proceed at 31° C., but not at 37° C. Amplicons packaged at 31° C. in the presence of HSV-1 tsK were successfully used to transfer the *E. coli* lacZ gene into primary cultures of rat neural cells (Geller, A. I. and Breakefield, X. O., *Science* 241:1667–1669 (1988)). Because the infection was performed at 37° C., the lytic cycle of the HSV-1 tsK helper virus present in the vector stock was blocked and cell damage was limited. Although replication of HSV-1 tsK was inhibited at the restrictive temperature, the expression of other viral genes caused cytopathic effects. Moreover, reversion to wild type (wt) HSV-1 occurred at a relatively high frequency, due to remaining functionality and reversion of the point mutation in tsICP4.

To counter these problems, replication-defective mutants of HSV-1 were then used as helper viruses (Geller, A. I. et al., *Proc. Natl. Acad. Sci. USA* 87:8950–8954 (1990); Lim, F., et al., *Bio Techniques* 20:458–469 (1996)). These mutants carry deletions in genes that are essential for virus replication, but they can support amplicon packaging in cells that complement the missing functions. However, many problems associated with the presence of helper virus in amplicon stocks still remained, including: (i) pronounced cytopathic effects and immune responses caused by gene expression from the helper virus; (ii) interactions between the helper virus and endogenous viruses; (iii) reversion of the helper virus to wt HSV-1; and (iv) disregulation of transgene expression by virus proteins.

Many of these problems have been overcome by the more recent development of a packaging system for herpes virus vectors that was free of helper virus (Fraefel, C., et al., *J. Virol.* 70:7190–7197 (1996); International Patent Publication WO 97/05263, published Feb. 13, 1997)). This system utilizes transient co-transfection of amplicon DNA with a set of five cosmids that overlap and represent the entire HSV-1 genome, but which are mutated to delete the DNA cleavage/packaging (pac) signals. Cunningham, C. and Davison, A. J., *Virology* 197:116–124 (1993), had demonstrated previously that after transfection into cells, an overlapping HSV-1 cosmid set can produce infectious virus progeny. By deleting the pac signals and making a pac-minus helper virus genome, HSV-1 genomes that are potentially reconstituted from the cosmids via homologous recombination, are not packageable, but can still provide all the helper functions required for the replication and packaging of the co-transfected amplicon DNA. The resulting vector stocks are, therefore, virtually free of detectable helper virus and have titers of $10^6$–$10^7$ tu./ml of culture medium. Because of minimal sequence homology between the cosmids and the amplicon DNA ($ori_S$ 0.2–1 kb), the formation of a packageable and replication-competent HSV-1 genome is possible but requires 6 recombination events, and is therefore very rare.

Amplicon vector stocks, produced by using the helper virus-free packaging system, can efficiently transduce many different cell types, including neural cells and hepatocytes in culture and in vivo, while causing minimal to no cytopathic effects (Fraefel, C., et al., *J. Virol.* 70:7190–7197 (1996); Fraefel, C., et al., *Mol. Med.* 3:813–825 (1997); Fraefel, C., et al., "HSV-1 Amplicon" in *Gene Therapy for Neurological Disorders and Brain Tumors*, E. A. Chiocca and X. O. Breakefield, eds., Humana Press, Totowa, pp. 63–82 (1998); Johnston, K. M., et al., *Hum. Gene Ther.* 8:359–370 (1997); Aboody-Guterman, K. S., et al., *Neuroreport* 8:3801–3808 (1997)). Even more recently, helper virus-free packaging has also been achieved using an oversized pac minus HSV genome, defective in an essential gene encoding ICP27, cloned into a BAC plasmid (Saeki, Y., et al., *Hum Gene Ther* 9:2787–2794 (1998).

One of the main objectives of gene therapy is to achieve stable genetic modification of target cells. This means that their progeny, or themselves in the case of non-dividing cells, should retain and express the newly introduced genetic material until the end of their lifespan, ideally in a regulated manner. This principle is equally valid when transgenes are introduced to correct genetic deficiencies or for treatment of non-hereditary diseases. The viral vector systems discussed above can achieve retention of the transgene through different mechanisms. For example, retrovirus and AAV vectors can integrate genes into the genome of infected cells, while EBV-derived vectors are maintained by episomal replication.

Moloney murine leukemia virus (MoMLV) derived retrovirus vectors are among the most commonly used vectors in gene therapy because of their ability to stably integrate transgenes in the genome of target cells, as well as their relative safety, simplicity, and easy production. However, their use for direct gene delivery in vivo has been limited due to several factors which result in low efficiency of gene transfer. These properties include: low titer, inability to infect non-dividing cells, limited tropism, and relatively short half-life. Although improvements have been made to address some of these issues, MoMLV-based retrovirus vectors are still mostly used for ex vivo protocols. These strategies involve removal of the target cells from the experimental subject or use of donor cells, genetic modification in culture by infection with retrovirus vectors carrying the transgene of interest, selection and characterization of transduced cells, and implantation of these cells in vivo.

An alternative to the direct injection of retroviral particles for in vivo gene delivery is the injection of retrovirus producer cells resulting in the local production of retrovirus vectors. This strategy has been used with therapeutic success in the treatment of experimental brain tumors (Culver, K. W. et al., *Science* 256:1550–1552 (1992)). In the clinical setting, however, the retrovirus packaging cells remain localized near the injection site, resulting in a very low efficiency of gene delivery to tumor cells, limited to areas in the immediate vicinity of the packaging cells (Ram, Z., et al., *Nature Med.* 182:1354–1361 (1997)). Further, the fact that the retrovirus packaging cells used are derived from mouse fibroblasts has several disadvantages and potential risks (Isacson, O. and X. O. Breakefield, *Nature Med.* 3:964–969 (1997)).

First, the retrovirus particles produced are extremely sensitive to inactivation by human serum via complement activation. This occurs because non-primate packaging cells add a Gal($\alpha$1–3)galactosyl group to the retroviral envelope and human serum has pre-existing antibodies against that sugar group (Rother, R. P., et al., *J. Experimen. Med.* 182:1345–1355 (1995); Takeuchi, Y., et al., *Nature* 379:85–88 (1996)). Second, the fact that these cells are mouse fibroblasts presents two difficulties: first, that fibroblasts transplanted into a brain tumor remain largely at the injection site and do not distribute throughout the tumor (Tamiya, T., et al., *Gene Ther.* 2:531–538 (1995); Tamura, M., et al., *Human Gene Ther.* 8:381–391 (1997)); second, their xenogeneic origin is likely to exacerbate an immune response even in immune privileged regions such as the central nervous system (CNS), thus limiting their survival time. A third consideration is safety since murine cells carry in their genome a large variety of MLV-like genomes which can be packaged by type C Gag proteins (Chakraborty, A. K., et al., *Cancer Gene Ther.* 1:113–118 (1994); Hatzoglou, M. et al., *Human Gene Ther.* 1:385–397 (1990); Scadden, D. T., et al., *J. Virol.* 64:424–427 (1990)) leading to recombination events which result in the production of replication-competent retroviruses (RCR).

Several packaging cell lines derived from human cells have been developed which could be used instead of the murine versions. These human retrovirus packaging cell lines package fewer endogenous sequences (Patience, C., et al., *J. Virol.* 72:2671–2676 (1998)), which reduce the probability of generating RCRs, and the virus particles are resistant to inactivation by human serum (Cossett, F. L., et al., *J. Virol.* 69:7430–7436 (1995)). However, there is also an increased risk for tumor formation since most of these cell lines are derived from transformed cells or human tumors. Since all stable retrovirus packaging cell lines available are derived from fibroblasts, fibrosarcomas or kidney cells, their migratory properties, for example, in the central nervous system (CNS), are very limited, while the target tumor cells present extensive migratory patterns (Pederson, P. H., et al., *Cancer Res.* 53:5158–5165(1993); Tamura, M. K., et al., *Hum. Gene Ther.* 8:381–391 (1997).

To increase the efficiency of gene delivery by retrovirus packaging cells, it will be necessary to generate new packaging cell lines derived from cells of different origins than fibroblasts or human kidney cells, preferentially primary cells, which by their migratory or tissue targetting properties will gain access to tumor cells or other target cell populations (Aboody-Guterman, K. S., "Neural stem cells migrate throughout and express foreign genes within experimental gliomas—a potential gene therapy approach to brain tumors" (submitted for publication, 1999); Brown, A. B. et al., "Vascular targeting of therapeutic cells to tumors" (in preparation,1999); Lal, B., et al., *Proc. Natl. Acad. Sci. USA* 91:9695–9699 (1994)). However, generation of retrovirus packaging cell lines is usually an inefficient, cumbersome work that takes, at least, several months to complete.

Several transient transfection systems that produce high titer retrovirus vector stocks in a very short period of time have been developed (Landau, N. R., and Littman, D. R., *J. Virol.* 66:5110–5113(1992); Naviaux, R. K., et al., *J. Virol.* 70:5701–5705 (1996); Soneoka, Y., et al., *Nucleic Acids Res.* 23:628–633 (1995)). Noguiez-Hellin et al. generated retrovirus producing cells in situ by transfection with a plasmid carrying all necessary functions for retrovirus packaging and vector generation (Noguiez-Hellin, P., et al., *Proc. Natl. Acad. Sci. USA* 93:4175–4180 (1996)). This group showed that the transgene could be generated in culture, but to a lesser extent on a tumor model in vivo, probably due to low transfection efficiency with the plasmid Although these systems produce high retrovirus titers, they are limited by varying efficiencies of transfection between cell lines and their transient nature.

Other systems for producing retroviral vectors take advantage of the efficient gene delivery and expression mediated by other types of viral vectors, such as those derived from herpes simplex virus (HSV) (Savard, N., et al., *J. Virol.* 71:4111–4117 (1997)), Semliki Forest virus (SFV) (Li, K. J. and H. Garoff, *Proc. Natl. Acad. Sci. USA* 93:11658–11663 (1996)), and adenovirus (Duisit, G., et al., *Human Gene Ther.* 10:189–200 (1999); Feng, M., et al., *Nature Biotechnol.* 15:866–870 (1997); Lin, X., *Gene Ther.* 5:1251–1258 (1998); Yoshida, Y., et al., *Biochem. Biophys. Res. Comm.* 232:379–382 (1997)). These systems utilize two or three different vectors to introduce the retroviral vector element and packaging functions, depending on whether the gag-pol and env genes are encoded in the same vector (Feng, M., et al., *Nature Biotechnol.* 15:866–870 (1997); Lin, X., *Gene Ther.* 5:1251–1258 (1998); Savard, N., et al., *J. Virol.* 71:4111–4117 (1997)), or the env gene is delivered by a separate vector (Duisit, G., et al., *Human Gene Ther.* 10:189–200 (1999); Li, K. J., and H. Garoff, supra; Lin, X., supra; Yoshida, Y., et al., *Biochem. Biophys. Res. Comm.* 232:379–382 (1997)). Although, one of these adenovirus/retrovirus chimeric systems has been shown to extend the duration of transgene expression in tumors in vivo when compared to a recombinant adenovirus vector (Feng, M., et al., *Nature Biotechnol.* 15:866–870 (1997)), all of these viral-based systems result in transient production of retrovirus vectors.

As discussed earlier, HSV amplicons are plasmid-based vectors that, in addition to a transgene of interest and corresponding expression elements, only need two non-coding HSV sequences, the origin of DNA replication (ori S) and a packaging signal ($\alpha$ sequence), to be packaged in HSV virions in the presence of helper functions (Spaete, R. R. and N. Frenkel, *Cell* 30:295–304 (1982)). These virions can infect a wide range of dividing and non-dividing cells, and with the development of the HSV helper virus-free packaging systems, discussed above, have essentially no toxicity. HSV virions package about 150 kb of DNA. The amplicon DNA is packaged as a concatamer approximately that size, containing multiple copies of the plasmid repeated in tandem, due to a rolling circle mode of viral DNA replication. This presents the advantages that a single virion can transduce a cell with multiple copies of a transgene and that these vectors can carry large genes and regulatory regions (for review, see, Fraefel, C., et al., *Gene Therapy for Neurological Disorders and Brain Tumors*, Humana Press, Totowa, N.J., pp. 63–82 (1998). However, one major limitation of HSV amplicon vectors has been the loss of amplicon DNA from the host cell nucleus over time, and therefore of gene expression. This is especially true in dividing cells (Johnston, K. M., et al., *Hum. Gene Ther.* 8:359–370 (1997)).

Recently, two different hybrid amplicon systems have been developed that incorporate elements from other viruses that serve to increase retention of the amplicon DNA and extend transgene expression: The first is an HSV/EBV hybrid amplicon, which includes two EBV elements in its backbone:(1) the latent origin of DNA replication (oriP); and (2) the gene encoding the Epstein-Barr nuclear antigen (EBNA-1), which supports nuclear replication of the amplicon DNA in dividing cells (Wang, S. and J. M. Vos, *J. Virol.* 70:8422–8430 (1996)). The second is an HSV/AAV hybrid amplicon which incorporates the AAV ITR element and rep gene. These elements have the potential to mediate replicative amplification and chromosomal integration of the transgene cassette (Johnston, K. M., et al., *Hum. Gene Ther.* 8:359–370 (1997)). This principle of incorporating these AAV elements to achieve chromosomal integration of transgenes with viruses that normally do not possess this property has also been used with baculovirus and adenovirus (Palombo, F., et al., *J. Virol.* 72:5025–5034 (1998); Recchia, A., et al., *Proc. Natl. Acad. Sci. USA* 96:2615–2620 (1999)).

Clearly, there is a need in the art for additional and more efficient hybrid amplicon vector systems that are capable of generating stable retrovirus packaging cell lines, in order to stably deliver a transgene, in vitro or in vivo, to a large number and type of dividing or non-dividing cells.

SUMMARY OF THE INVENTION

In the present invention, HSV amplicons, in combination with elements from other viruses, are utilized to generate retrovirus packaging cells. More specifically, the present invention relates to the development and characterization of a gene delivery system based on an HSV/EBV or an HSV/AAV hybrid amplicon vector, each of which have been modified to contain retroviral packaging functions and a retrovirus vector cassette. The ability of these hybrid amplicon vectors to induce retrovirus vector production was assessed in a number of different cells, as well as in vivo in a nude mouse model. High titer recombinant retrovirus vectors were obtained both by transfection and infection of different cell lines. These hybrid amplicon vectors can also mediate cumulative transgene delivery in cell populations starting from a small fraction of amplicon-infected cells.

Using current technology, the generation of packaging cell lines is a process which requires several rounds of transfection, selection, and screening. Due to its time consuming nature, most of the cell lines that have been generated have very limited biological interest beyond packaging recombinant retrovirus vectors. Most of the cells are derived from mouse fibroblasts and more recently human cell lines. The vector system of the present invention will be able to shift the burden of work from generating packaging cell lines per se, to using the biologic properties of different cell types for specific applications. Moreover, the generation of packaging cells in vivo will allow direct access to a variety of endogenous cells.

One example of how the vector systems of the present invention will improve the art is in the use of retroviral vectors for cancer gene therapy, which is currently in human clinical trials. The rationale behind these trials is that the retrovirus vectors generated by a packaging cell line, which is injected into a tumor, will infect neighboring dividing tumor cells, rendering them more sensitive to a prodrug, radiation, or conventional chemotherapy. In brain tumors, namely glioblastomas, the main tumor mass is frequently accessible to the neurosurgeon for removal. However, death in most cases results from tumor recurrences which develop close to the original tumor mass, as well as in other places in the central nervous system, sometimes as far away as the opposite hemisphere from where the initial tumor mass was located. This is due to the extraordinary ability that these tumor cells have to migrate and spread in the adult brain. Currently used packaging cell lines derived from rodent fibroblasts, which have been used for brain tumor therapy, remain at the injection site, and some studies have shown that encapsulation of the grafted cells can occur. This suggests that fibroblasts which are transplanted into the central nervous system do not display any migratory ability. Delivery of vector is further reduced as this procedure involves xenotransplantion of mouse cells into humans. These cells elicit an immune response which eventually leads to their elimination and hence cessation of vector delivery. It can be argued that the immune response to the packaging cells is limited, since most brain tumor patients undergo treatment with immune suppressants, the CNS is a somewhat immune-privileged site, and brain tumors themselves may also suppress the immune system. Even if these arguments have some biologic significance, the fact that the packaging cells lack the ability to migrate, limits the therapeutic strategy from the beginning, since it does not address one of the basic properties of brain tumors—invasiveness. By using the vector system of the present invention, where transforming cells into retrovirus packaging cells is simple, fast, and efficient, it will be possible to investigate and implement the biologic properties that these cells need to deliver genes to tumor cells efficiently in vivo.

One could go as far as proposing that tumor cells should themselves be transformed into packaging cells in cell culture, and implanted back into the tumor cavity. This ex vivo strategy of transforming cells into packaging cells according to the present invention has much broader applications than just tumor therapy, and could be used to transform other primary cells into packaging cells. For example, one could use the vector system of the present invention, which takes advantage of migratory and organ homing properties of different cells, for gene delivery to tissues or organs where cell proliferation occurs in the adult or during development.

The most exciting property of the vector system of the present invention, however, is the ability to transform cells into packaging cells in vivo. This can be achieved in a single transduction step, which can be accomplished using liposomes, electroporation, molecular conjugates and DNA guns, or any other method to introduce DNA into cells in vivo or by infection using the vector's ability to be packaged into HSV virions.

As discussed above, retrovirus vectors have been long recognized as useful tools for gene transfer in cell culture, but with limited applicability in vivo due to their characteristic low titers, i.e., infectious units/ml of virus stock, inability to transduce non-dividing cells, and finally their fragility, which precludes efficient concentration of viral stocks. However, retrovirus present a tremendous advantage in relation to other vectors with their ability to stably integrate into the host genome. For these reasons, retrovirus vectors have been used mostly in ex vivo protocols where target cells are grown in culture, and after being infected with the desired vector and selected, they are transplanted back into the individual. What the vector system of the present invention can accomplish is to transform cells in vivo into packaging cells which will deliver retrovirus vectors over an extended period of time, without being destroyed by the process of packaging, as occurs during production of most other vectors used for gene delivery.

While the development of vectors that can efficiently infect non-dividing cells and achieve very high titers has been accomplished by a series of vectors, including adenovirus, AAV, and HSV, there are still major hurdles that limit the therapeutic efficacy of those vectors. First, is the fact that the vectors that achieve the highest titers and infect non-dividing cells do not stably integrate into the genome and elicit strong immune responses from the host. Second, direct injection of the viral vector will only affect the organ or tissue in a very localized manner, not always enough to achieve a therapeutic effect. Several strategies have been developed to address this latter issue that make use of more generalized gene delivery protocols such as injection of vectors in the bloodstream, which in most cases, however, results in gene delivery to the liver. In the case of generalized gene delivery to the brain, several strategies have been tried such as the chemically induced temporary disruption of the blood brain barrier which allows vectors to cross it and infect cells in brain tumors or in the brain parenchyma. Although these strategies have been rather successful in gene marking experiments, the vectors used in those experiments have been unable to mediate stable gene expression for a variety of reasons that range from immune compromise of gene delivery to the episomal nature of those vectors.

Accordingly, the present invention overcomes the disadvantages of the prior art because the present hybrid amplicon vector systems take advantage of the migratory and organ or tissue homing properties of certain cells to deliver retrovirus vectors in situ by transforming those cells into retrovirus packaging cells. Furthermore, once the retrovirus vectors integrate into the genome of the target cells, this genetic element should be stable and transmitted to the progeny of those cells. Another property of this system is that it can be used both as an HSV-amplicon vector or as a plasmid to achieve the same goals.

Thus, the present invention provides hybrid amplicon vectors comprising genetic elements derived from several viruses: Herpes Simplex Virus (HSV), Epstein-Barr Virus (EBV) or Adeno-Associated Virus (AAV), and a retrovirus.

In one embodiment, the hybrid amplicon vector comprises elements from HSV, EBV, and a retrovirus. In a preferred embodiment, the hybrid amplicon vector comprises: (a) an HSV origin of replication (ori S); (b) an HSV packaging signal (pac); (c) an EBV origin of replication (ori P); (d) an expression cassette of the EBNA-1 protein of EBV; (e) gag, pol, and env genes of a retrovirus; and (f) a retroviral vector, containing at least one transgene of interest. Of course, other genetic elements may also be present in the amplicon portion of the construct, such as additional regulatory (i.e., promoter), therapeutic, reporter, or marker genes.

In a particularly preferred embodiment of the HSV/EBV/retrovirus vector embodiment, the hybrid vectors are HERE and HERA.

In another embodiment, the amplicon vector comprises elements from HSV, AAV, and a retrovirus. In a preferred embodiment, the hybrid amplicon vector comprises: (a) an HSV origin of replication (ori S); (b) an HSV packaging signal (pac); (c) an AAV rep gene; (d) an AAV ITR element; (e) gag, pol, and env genes of a retrovirus; and (f) a retroviral vector, containing at least one transgene of interest. Of course, other genetic elements may also be present in the amplicon portion of the construct, such as additional regulatory (i. e., promoter), therapeutic, reporter, or marker genes.

In a particularly preferred embodiment of the HSV/AAV/retrovirus vector embodiment, the hybrid vectors are HyRMOV Ampho and HyBPlacZ.

Both vector system embodiments are capable of generating retroviral packaging cells.

The retroviral vector will have at least one transgene inserted therein. The transgene(s) may be a reporter or marker gene, and/or a therapeutic gene. Representative examples of suitable reporter genes include: β-galactosidase, green fluorescent protein (GFP), galactokinase, alkaline phosphatase, chloramphenicol acetyltransferase, luciferase, and β-lactamase. Representative examples of suitable selectable marker genes include gene sequences capable of conferring host resistance to antibiotics (such as ampicillin, tetracycline, kanamycin, etc.), amino acid analogs, or genes permitting growth of bacteria on additional carbon sources or under otherwise impermissible culturing conditions. The therapeutic transgene sequence may be a gene sequence associated with diseases and disorders including, but not limited to, inherited metabolic disorders, including, lysosomal storage disease, Lesch-Nyhan syndrome, inherited neurological diseases, including, amyloid polyneuropathy, Alzheimer's Disease, Duchenne's muscular dystrophy, ALS, Parkinson's Disease and brain tumors, diseases of the blood, such as, sickle-cell anemia, clotting disorders and thalassemias, cystic fibrosis, diabetes, disorders of the liver and lung, heart and vascular disease, diseases associated with hormone deficiencies, movement disorders, pain, stroke, cancer, and HIV.

The invention further provides a method for expressing a transgene in a proliferating cell population, in vitro or in vivo using the hybrid vectors of the invention. Some exemplary in vivo applications for the gene delivery system of the invention include gene delivery to the central nervous system during neurogenesis and gliogenesis, gene delivery to the bone marrow for the correction of genetic disorders as well as to protect the bone marrow from infection (as in HIV-infected individuals or other immune deficient individuals), gene delivery to the developing liver, and gene delivery to the lung during development.

The invention also provides a method of treating diseases and disorders using the hybrid vectors of the invention. Non-limiting examples of the diseases and disorders that can be treated using the present hybrid vectors include: inherited metabolic disorders, including, lysosomal storage disease, Lesch-Nyhan syndrome, inherited neurological diseases, including, amyloid polyneuropathy, Alzheimer's Disease, Duchenne's muscular dystrophy, ALS, Parkinson's Disease, diseases of the blood, such as, sickle-cell anemia, clotting disorders and thalassemias, cystic fibrosis, diabetes, disorders of the liver and lung, heart and vascular disease, diseases associated with hormone deficiencies, movement disorders, pain, stroke, HIV, tumors, neoplasms, carcinomas, sarcomas, leukemias, lymphoma, astrocytomas, oligodendrogliomas, meningiomas, neurofibromas, ependymomas, Schwannomas, neurofibrosarcomas, and glioblastomas.

In one preferred embodiment, the invention provides a method of selectively killing neoplastic cells using the hybrid vectors of the invention.

The invention also provides a preferred embodiment of the foregoing vector wherein any of the above mentioned hybrid amplicon vectors are capable of generating retrovirus packaging cells in a single step. One or two hybrid amplicons can be used to deliver the retroviral vector components.

It is to be understood that both the foregoing general description and the following detailed description are exemplary and explanatory and are intended to provide further explanation of the invention as claimed.

BRIEF DESCRIPTION OF THE FIGURES

FIG. 1A is a schematic representation of the HSV/EBV/Retrovirus ("HER") hybrid amplicons which code for the Moloney murine leukemia virus (MoMLV) gag-pol and env genes. These genes are under the control of the CMV promoter and are followed by the bovine growth hormone polyadenylation signal (BGHpA). The HERE lacZ A1 and A7 amplicons code for the Ecotropic env gene, while the HERA lacZ B3 and B7 amplicons code for the Amphotropic env gene derived from the 4070A genome.

FIG. 1B is a schematic representation of the HER lacZ amplicons C1 and C5, which are missing the MoMLV gag-pol-env genes. Amplicon clones A7, B3, and C5 bear the retrovirus lacZ cassette in opposite orientation to the GPE cassette, whereas clones A1, B7, and C1 have it in the same orientation.

Abbreviations: LTR, long terminal repeat; ψ, retrovirus packaging signal; lacZ, E. coli beta-galactosidase; SV40, simian virus 40 promoter; α, HSV packaging signal; Col El, E. coli origin of plasmid replication; $Amp^R$ ampicillin resistance gene; RSV, Rous sarcoma virus promoter; EBNA-1 (del), Epstein-Barr nuclear associated antigen 1 with most of the internal Gly-Ala repetitive sequence deleted (Yates, J. L., et al., Nature 313:812–815 (1985)); oris P, EBV latent origin of replication which contains two elements, the family of repeats (FR) and dyad symmetry (DS) element; $ori_S$HSV origin of DNA replication; IE 4/5; HSV immediate/early 4/5 promoter; EGFP, enhanced green fluorescent protein gene; SV40pA, simian virus 40 polyadenylation signal.

Figure 2:
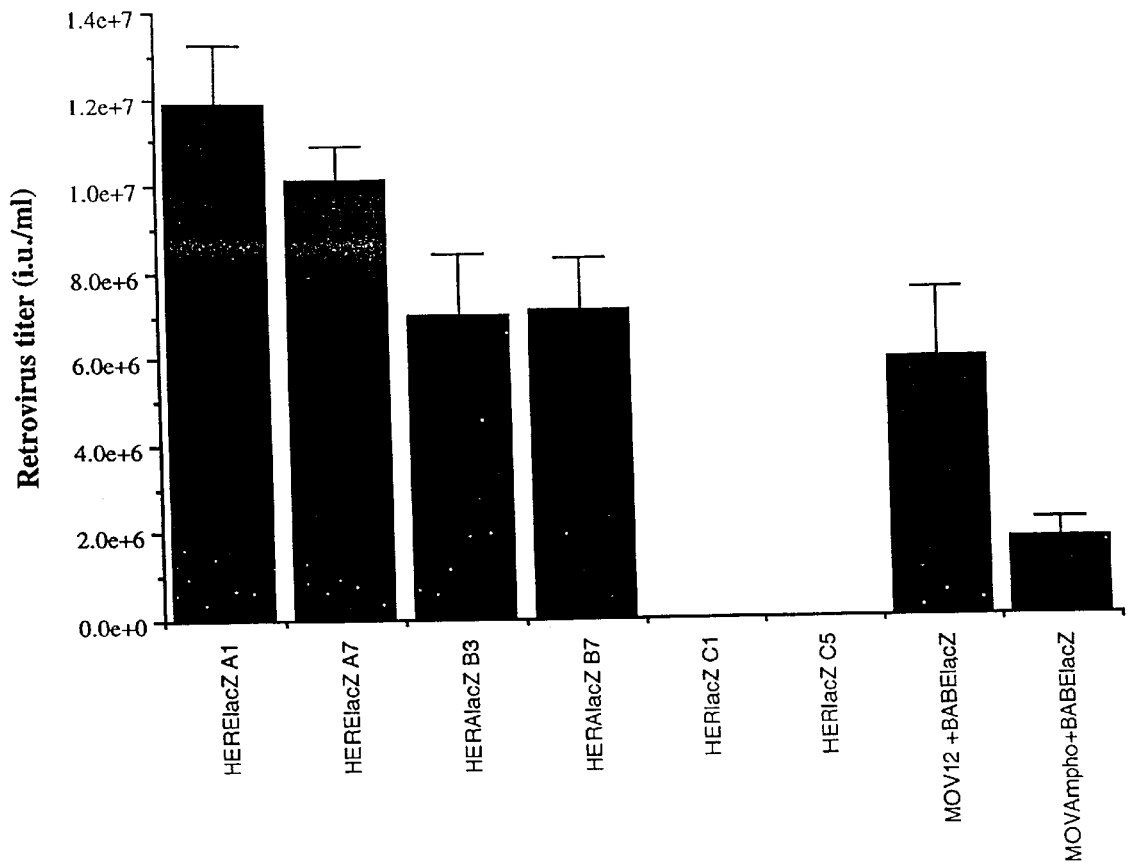

FIG. 2 is a bar graph depicting retrovirus production in 293T/17 cells after transfection with amplicon constructs. Two million cells were transfected by calcium phosphate co-precipitation with HERE lacZ A1 and A7 amplicons, HERA lacZ B3 and B7 amplicons, and HER lacZ C1 and C5 amplicons. Cells were also co-transfected with BABE lacZ and MOV12 plasmids, and BABE lacZ and MOV Ampho plasmids. Retrovirus titers assessed 48 hours post-transfection represent the average of two experiments repeated in triplicate and the error bars represent standard deviations.

FIGS. 3A and 3B depict retrovirus vector production in 293T/17 cells 48 hours after infection with amplicon vectors. FIG. 3A: To test if the orientation of the retrovirus vector cassette in relation to the CMV-GPE cassette had any effect on retrovirus titers, cells were infected at MOI of 2 with amplicon vectors HERE lacZ A1 (1), HERE lacZ A7 (2), HERA lacZ B3 (3), and HERA lacZ B7 (4), and 48 hours later the supernatants were harvested for titering. A neutralization experiment was performed to demonstrate that retrovirus production is dependent on amplicon transduction. HERA lacZ B7 amplicon vector stocks (MOI of 2) were incubated for 10 minutes with a rabbit anti-HSV-1 antibody (5), normal rabbit serum (6), and an unrelated rabbit antibody (7), before infecting 293T/17 cells. Media were harvested 48 hours later for titering.

FIG. 3B depicts the relation between multiplicity of infection and retrovirus titers generated 48 hours post-infection. Cells were infected at different MOIs with HERE lacZ A1 (open squares) and HERA lacZ B7 (solid diamonds). The relation between MOI and transduction efficiency was also evaluated (open triangles). When supernatants were harvested for retrovirus titering, cells were analyzed by FACS to determine the percentage of cells expressing GFP as a measure of the amplicon transduction efficiency.

FIGS. 4A, 4B, and 4C depict retrovirus production over time for J3T and Gli-36 cells infected with HERA lacZ B7 amplicon vector at different MOIs. One day prior to infection, $5 \times 10^5$ cells were seeded on 60 mm plates. In FIG. 4A, J3T cells were infected at MOI of 1 (open square), 2 (solid diamond) and 5 (solid square).

In FIG. 4B, Gli-36 cells were infected at MOI of 1 (open square ), 2 (solid diamond) and 5 (solid square). Media were harvested at 2, 5 and 8 days post-infection and used for retrovirus titering. At 2 and 5 days post-infection, cells were counted and replated at the same density as on day 0.

In FIG. 4C, the percentage of GFP-positive cells was determined at 2, 5 and 8 days post-infection for J3T (MOI 2-open squares; MOI 5-open circles) and Gli-36 cells (MOI 2-solid circle; MOI 5-solid triangle).

FIGS. 5A and 5B depict Western blot analyses of $Pr65^{gag}$ and gp70 expression in J3T and Gli-36 cells at 2 and 8 days post-infection with HERA lacZ B7 and HER lacZ C1 amplicon vectors at MOI of 2. FIG. 5A depicts Pr65gag expression; FIG. 5B depicts gp70 expression.

Lanes 1 and 4, lysates of naive J3T cells at 2 and 8 days; lanes 2 and 5, lysates of J3T cells at 2 and 8 days post-infection with HERA lacZ B7; lane 3 and 6, lysates of J3T cells at 2 and 8 days post-infection with HER lacZ C1; lanes 7 and 10, lysates of naive Gli-36 cells at 2 and 8 days; lanes 8 and 11, lysates of Gli-36 cells at 2 and 8 days post-infection with HERA lacZ B7; lanes 9 and 12, lysates of Gli-36 cells at 2 and 8 days post-infection with HER lacZ C1. Goat anti-p30 and anti-gp70 antibodies were used at 1:3000 dilution. Anti-goat IgG peroxidase conjugated was used as secondary antibody at 1:5000 dilution. Blots were developed with ECL reagents and exposed to film for 1 minute.

FIGS. 6A, 6B, and 6C depict beta-galactosidase activity in amplicon infected J3T and Gli-36 cell populations over time. In FIG. 6A, J3T (open squares) and Gli-36 cells (solid diamonds) were infected with HERA lacZ B7 amplicon vector at MOI of 2 and lacZ activity in the population was measured at different timepoints up to 1 month. LacZ activities at 48 hours for J3T and Gli-36 cells were 317.2 and 79.7 mU/mg protein, respectively.

In FIG. 6B, J3T (open squares) and Gli-36 cells ( solid diamonds ) were infected with HER lacZ C1 amplicon vector at MOI of 2 and lacZ activity in the population was assayed at different timepoints up to 1 month.

In FIG. 6C, Gli-36 cells were infected with HERA lacZ B7 amplicon vector at MOI 2 (open diamonds), 1 (solid square), 0.5 (solid diamonds) and 0.1 (open squares) and lacZ activity in the population was measured at different timepoints up to 15 days. LacZ activities at 48 hours post infection for MOIs of 2, 1, 0.5, and 0.1 were 147.5, 94.6, 62.3, and 9.6 mU/mg protein, respectively. LacZ activities for all experiments were represented as the percentage of lacZ activity at 48 hours. Results represent the average of two experiments repeated in triplicate for each cell line.

Figure 7:
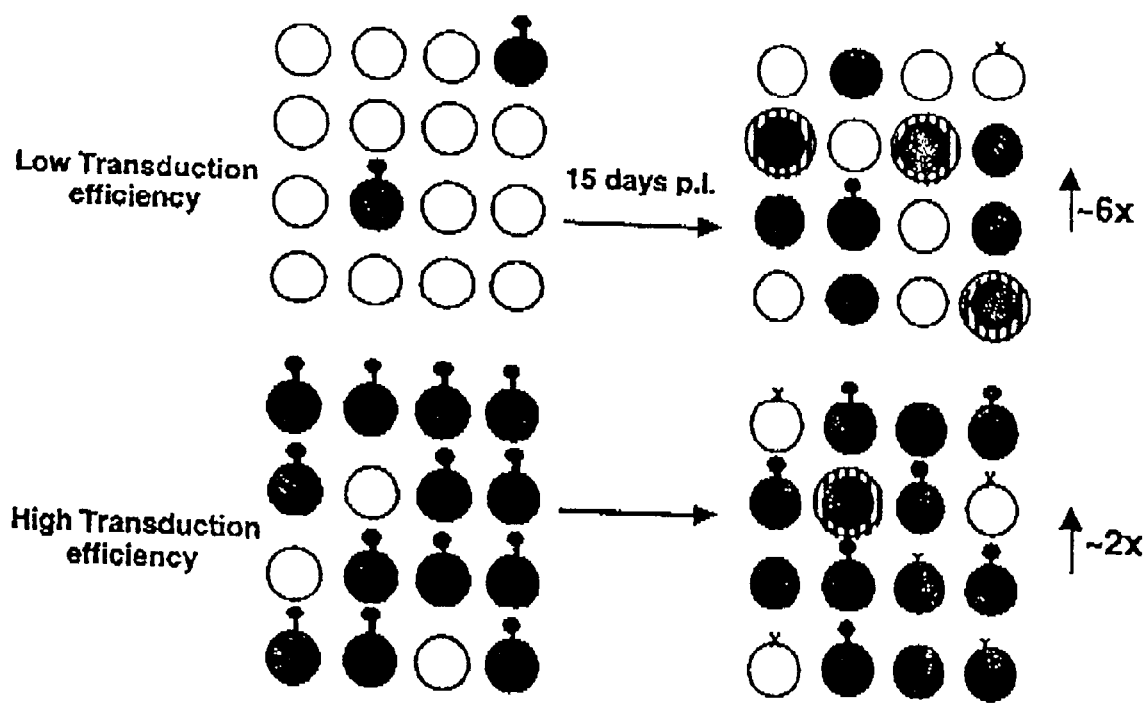

FIG. 7 depicts a model of cumulative increase in transgene expression in cell populations infected with the triple hybrid vector (also known as a "tribrid" vector). The hypothesized dynamics of transgene expression are shown for two different transduction efficiencies immediately after infection with the tribrid amplicon vector and 2 weeks later, assuming a dividing cell population. Right after infection, uninfected cells (indicated as open circles) do not express the lacZ transgene, and cells infected with the amplicon vector (filled circles with "lollipop") express lacZ and retroviral proteins, which interfere with their ability to be infected with retrovirus vectors. After 2 weeks, a number of parallel phenomena have occurred. Some initially uninfected cells are now infected once by a retrovirus vector (lacZ+, filled circles) or multiple times with retrovirus vectors (higher lacZ expression, filled circles with halo). Over the same period, some cells initially infected with the amplicon vector have lost the episomal amplicon and hence their ability to produce lacZ or retroviral proteins (open circle with x), while some of these have subsequently become infected by retrovirus vectors produced by amplicon infected cells that retain the episomal tribrid (lacZ+, filled circles with x). Therefore, at low transduction efficiency, when only a small fraction of cells are initially infected with the amplicon vector, there is a larger increase in the total lacZ activity of the population, as compared to populations with high levels of initial transduction. Eventually the episome tribrid is lost from all cells, and then the population should reach a steady state level of lacZ expression reflecting the number of successful infections with retrovirus vectors.

FIGS. 8A and 8B depict the HSV/AAV/Retrovirus hybrid amplicon constructs ("HAR") of the invention. FIG. 8A is a schematic representation of the HyRMOV Ampho hybrid amplicon which codes for Moloney murine leukemia virus (MoMLV) gag-pol and env genes (GPE). The gag-pol genes were derived from the MOVΨ vector (Mann, R., et al., *Cell* 33:153–159 (1983)), while the env gene was derived from the 4070A amphotropic genome (Chattopadhyay, S. K., et al., *J. Virol.* 39:777–791 (1981)). These genes are expressed under the control of the cytomegalovirus immediate-early promoter (CMV) and the bovine growth hormone polyadenylation signal (BGHpA). An expression cassette conferring G418 resistance (neo) is present, under the control of the simian virus 40 origin of replication/promoter (SV40) and polyadenylation signal (SV40pA). These two cassettes are flanked by adeno-associated virus (AAV) inverted terminal repeats (ITR). The AAV rep gene (Rep) is expressed under the control of its own regulatory region and an SV40polyA signal. The herpes simplex virus (HSV) origin of DNA replication ($ori_s$) and cleavage/packaging signal (pac) direct packaging of these plasmids in HSV virions.

FIG. 8B is a schematic representation of the HyBPlacZ hybrid amplicon. In this construct, the GPE and neo expression cassettes were replaced by a MoMLV derived retrovirus vector expressing the *E. coli* beta-galactosidase gene (lacZ).

Abbreviations: S.D., splicing donor; S.A., splicing acceptor; LTR, retroviral long terminal repeat; Ψ, retrovirus packaging signal; puro, puromycin resistance gene; Col E1, *E. coli* origin of plasmid replication; $AmP^R$, ampicillin resistance gene. Stipled bar represents the 1.2 kb lacZ probe used for Northern blot.

FIGS. 9A and 9B depict the effect of the Rep gene cassette on the activity of the downstream 5' LTR promoter. (FIG. 9A) Hybrid retrovirus vectors designed to test this effect: (a) HyBPlacZ; (b) HSHyBPlacZ #2.2; (c) HSHyBPlacZ #2.1; (d) HSTVBPlacZ #3.2; (e) HSTVBPlacZ #1.2; (f) HSRepTVBPlacZ #1.1; (g) HSRepTVBPlacZ #3.5.

(FIG. 9B) Human 293T/17 cells were co-transfected with the following retrovirus vector plasmids: TVBPlacZ (1,2); HyBPlacZ (3,4); HSHyBPlacZ #2.2 (5,6); HSHyBPlacZ #2.1 (7,8); HSTVBPlacZ #3.2 (9,10); HSTVBPlacZ #1.2 (11,12); HSRepTVBPlacZ #1.1 (13, 14); HSRepTVBPlacZ #3.5 (15, 16); and HSvec2 plasmid (1,3,5,7,9,11,13,15,17); and HSRepN1 plasmid which provides Rep in trans (2,4,6, 8,10,12,14,16,18). All samples were co-transfected with pcDNA3.1 luc expression plasmid encoding the firefly luciferase gene to normalize for transfection efficiency. Untransfected cells are shown in (19).

Two days post-transfection, lacZ and luciferase activities were determined for each sample. The activity of the LTR promoter in each vector for each experimental condition was expressed as a ratio between lacZ activity and luciferase activity (internal control for transfection efficiency) and compared to the average of ratios obtained for TVBP lacZ transfected cells (Relative LTR activity). Experiment was repeated twice in triplicate.

Figure 10:
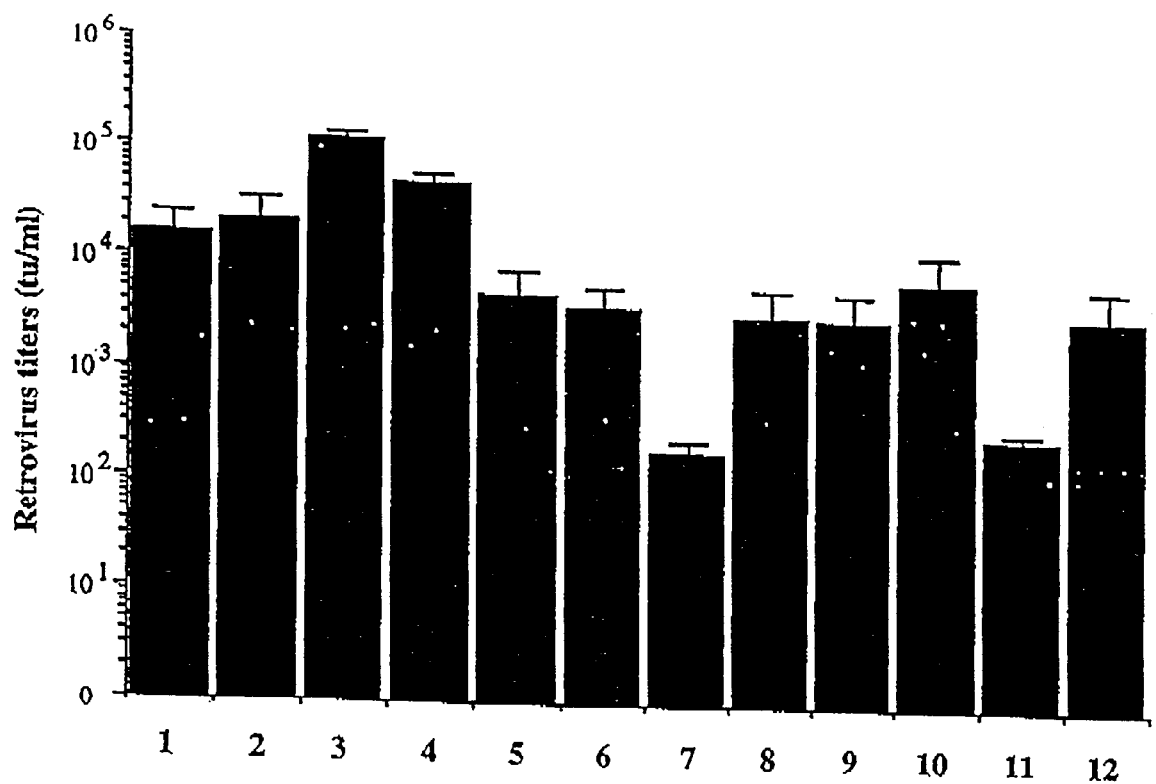

FIG. 10 is a bar graph depicting retrovirus titers after simultaneous infection with HSHyBPlacZ #2.2 and HyRMOV Ampho amplicon vectors. Cells were infected at the same MOI for each vector and two days later the medium was harvested for retrovirus titering. Infected cells were placed under double drug selection (G418+puromycin) and retrovirus titers were determined at 30 and 55 days post-infection. Gli-36 cells: (1) MOI 1, 48 hours; (2) MOI 5, 48 hours; (3) MOI 5, 30 days; (4) MOI 5, 55 days. J3T cells: (5) MOI 2, 48 hours; (6) MOI 2, 30 days; (7) MOI 2, 55 days; (8) MOI 5, 48 hours; (9) MOI 5, 30 days; (10) MOI 5, 55 days. 293T/17: (11) MOI 1, 48 hours; (12) MOI 5, 48 hours.

Figure 11:
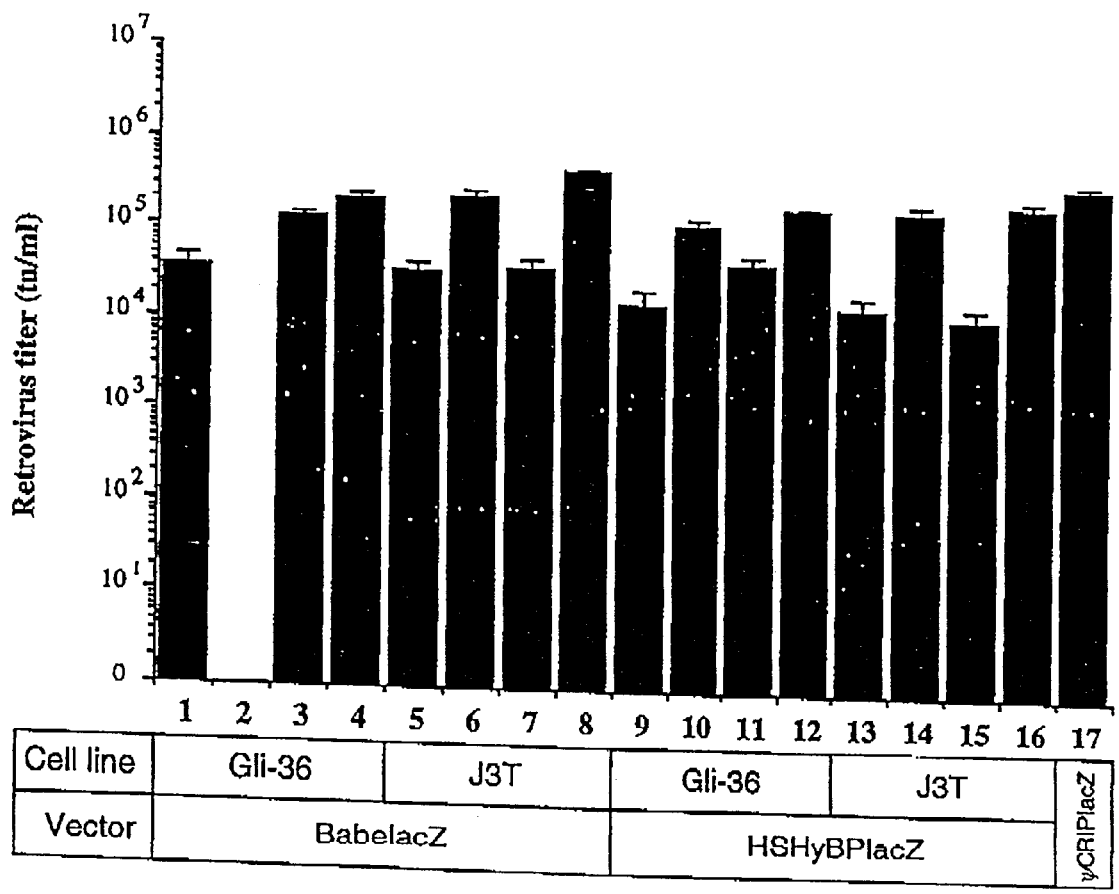

FIG. 11 depicts retrovirus titers produced by stable cell lines obtained by a double step strategy. Gli-36 and J3T cells were first infected with two different retrovirus vectors, BabelacZ and HSHyBPlacZ, and selected for a population 100% puromycin resistant. Cells were then infected with HyRMOV Ampho amplicon at different MOIs and selected in G418. Retrovirus titers were determined at 48 hours and 86 days post-infection. Gli-36 infected with BabelacZ vector: (1) MOI 1, 48 hours; (2) MOI 1, no long term G418 resistant population was obtained; (3) MOI 5, 48 hours; (4) MOI 5, 86 days. J3T cells infected with BabelacZ: (5) MOI 2, 48 hours; (6) MOI 2, 86 days; (7) MOI 5, 48 hours; (8) MOI 5, 86 days. Gli-36 cells infected with HSHyBPlacZ: (9) MOI 1, 48 hours; (10) MOI 1, 86 days; (11) MOI 5, 48 hours; (12) MOI 5, 86 days. J3T cells infected with HSHyBPlacZ: (13) MOI 2, 48 hours; (14) MOI 2, 86 days; (15) MOI 5, 48 hours; (16) MOI 5, 86 days. (17) ΨCRIPlacZ cells were plated at the same density as J3T and Gli-36 cells and 3 days later the supernatant was titered.

FIGS. 12A and 12B are Western blots depicting the expression of retroviral proteins in stable vector producer cell lines. FIG. 12A depicts expression of gag-pol gene products; FIG. 12B depicts gp70 expression.

Lane 1, lysates of naive Gli-36 cells; lane 2, lysates of naive J3T cells; lane 3, lysates of ΨCRIPlacZ cells; lanes 4 and 5, lysates of J3T and Gli-36 cells infected simultaneously with both hybrid amplicon vectors and double selected for 55 days post-infection, respectively; lanes 6 and 7, lysates of BabelacZ modified J3T cells infected at MOI of 2 and 5 with HyRMOV Ampho amplicon vector, respectively, after 86 days of selection; lanes 8 and 9, lysates of HSHyBPlacZ modified J3T cells infected at MOI of 2 and 5 with HyRMOV Ampho amplicon vector, respectively, after 86 days of selection; lane 10, lysates of BabelacZ modified Gli-36 infected at MOI 5 with HyRMOV Ampho amplicon vector, respectively, after 86 days of selection; lanes 11 and 12, lysates of HSHyBPlacZ modified Gli-36 cells, infected at MOI 1 and 5 HyRMOV Ampho amplicon vector, respectively, after 86 days of selection. Goat anti-p30 and anti-gp70 antibodies were used at 1:3000 dilution. Anti-goat IgG peroxidase conjugated was used as secondary antibody at 1:5000 dilution. Blots were developed with ECL reagents and exposed to film for 5 minutes.

Figure 13:
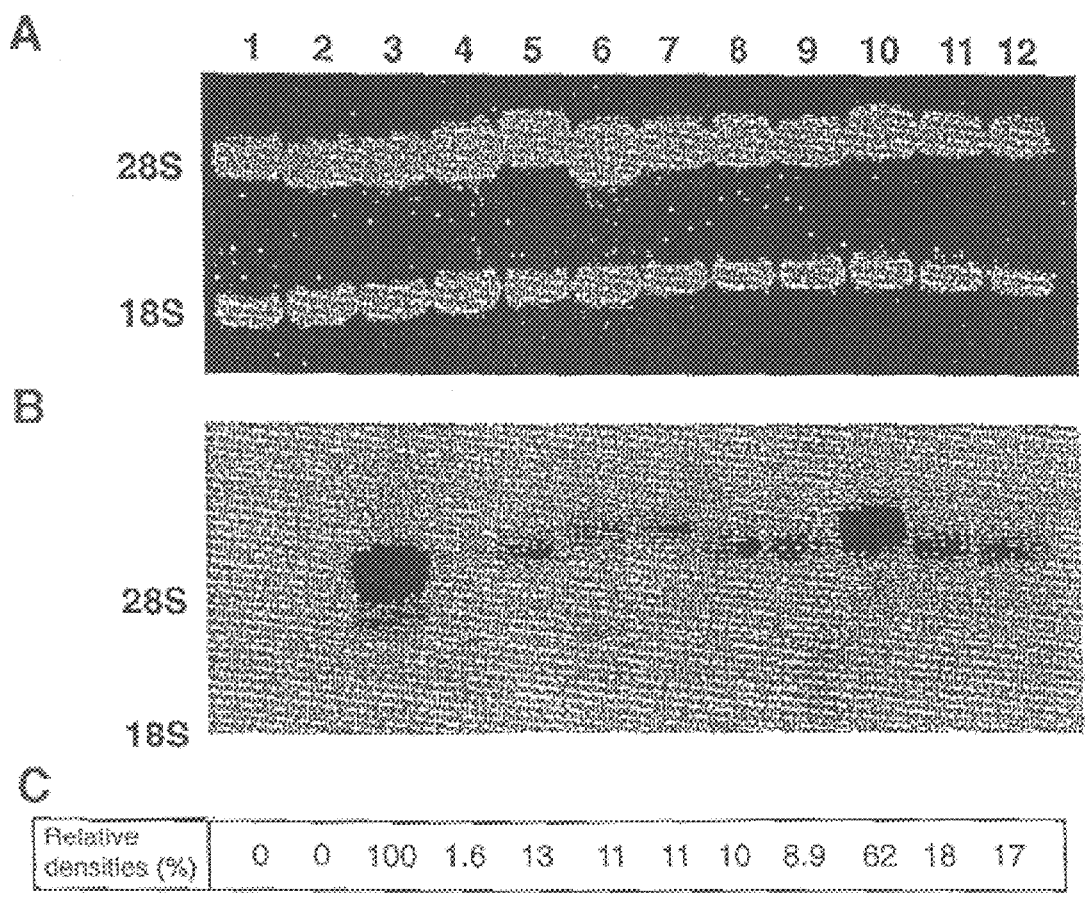

FIGS. 13A, 13B, and 13C depict levels of packageable vector RNA. Total RNA was extracted from cell lines using Trizo™ reagent: Lane 1, naive Gli-36 cells; lane 2, naive J3T cells; lane 3, ΨCRIPlacZ cells; lanes 4 and 5, J3T and Gli-36 cells infected simultaneously with both hybrid amplicon vectors and double selected for 55 days post-infection, respectively; lanes 6 and 7, BabelacZ retrovirus modified J3T cells infected at MOI of 2 and 5 with HyRMOV Ampho amplicon vector, respectively, after 86 days of selection; lanes 8 and 9, HSHyBPlacZ retrovirus modified J3T cells infected at MOI of 2 and 5 with HyRMOV Ampho amplicon vector, respectively, after 86 days of selection; lane 10, BabelacZ retrovirus modified Gli-36 infected at MOI 5 with HyRMOV Ampho amplicon vector, respectively, after 86 days of selection; lane 11 and 12, HSHyBPlacZ retrovirus modified Gli-36 cells, infected at MOI 1 and 5 HyRMOV Ampho amplicon vector, respectively, after 86 days of selection. In FIG. 13A, total RNA (20 µg) was separated by electrophoresis in a 1.1% agarose-formaldehyde gel at 4 V/cm for 3 hours.

In FIG. 13B, RNA was transferred to nitrocellulose and the blot was probed with a 1.2 kb lacZ DNA fragment labeled with $^{32}$P In FIG. 13C, relative band densities are shown. Films were scanned and the bands were analyzed for their integrated densities using the NIH Image 1.62 software and represented as a percentage of the most intense band (ΨCRIPlacZ sample—lane 3).

Abbreviations: 28S and 18S indicate the ribosomal RNAs of that size and in FIG. 13B their relative positions are also indicated.

Figure 14:
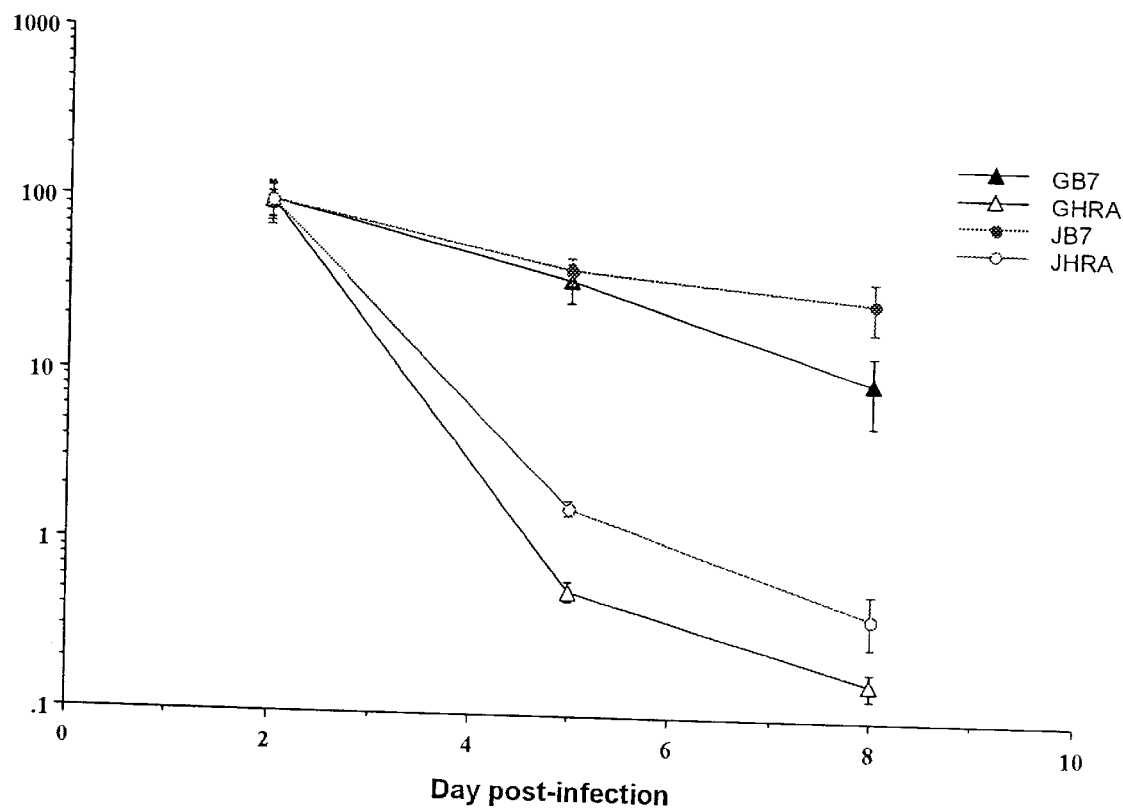
Figure 15:
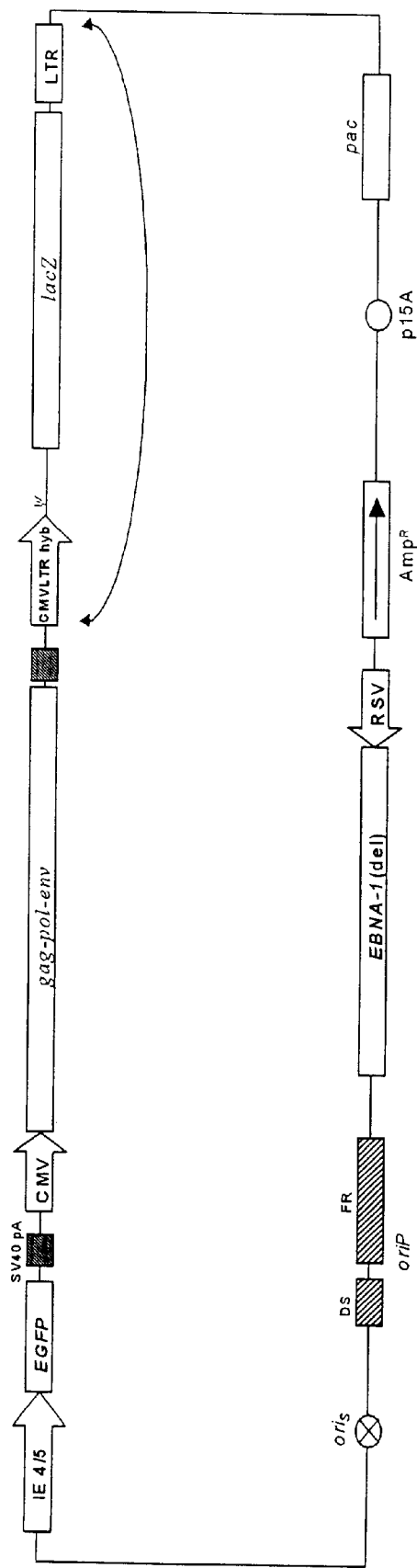

FIG. 14 is a graph depicting the effect of Epstein-Barr virus elements on the duration of retrovirus vector production by tumor cells. Human Gli-36 glioma cells (triangles) and J3T dog glioma cells (circles) were infected at MOI of 2 with the HSV/EBV/Retrovirus tribrid amplicon (B7; closed triangle and circle) and an HSV amplicon with identical structure but missing the EBV oriP and EBNA-1 gene (HRA; open triangle and circle). Retrovirus production was analyzed over a period of 8 days. Titers were normalized for vector titers at 3 days post-infection FIG. 15 depicts the structure of HERAC vectors. The retrovirus vector component was modified by replacing the 5' LTR with a CMV-LTR hybrid promoter. This modified retrovirus vector was inserted in the HER backbone in two different orientations (K16 and K19).

Figure 16:
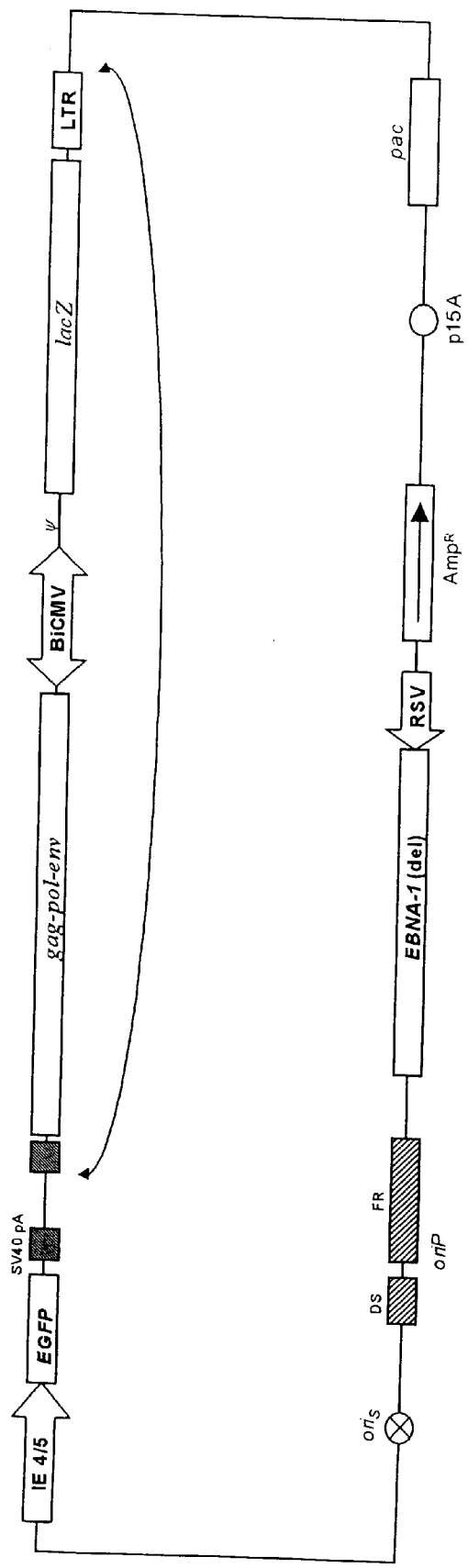

FIG. 16 depicts the structure of BiHERA vectors. Expression of the retrovirus structural genes and vector element were placed under the control of a bidirectional CMV promoter. This cassette was cloned in the HSV/EBV amplicon backbone in two different orientations (Clones Q4 and Q8).

Figure 17:
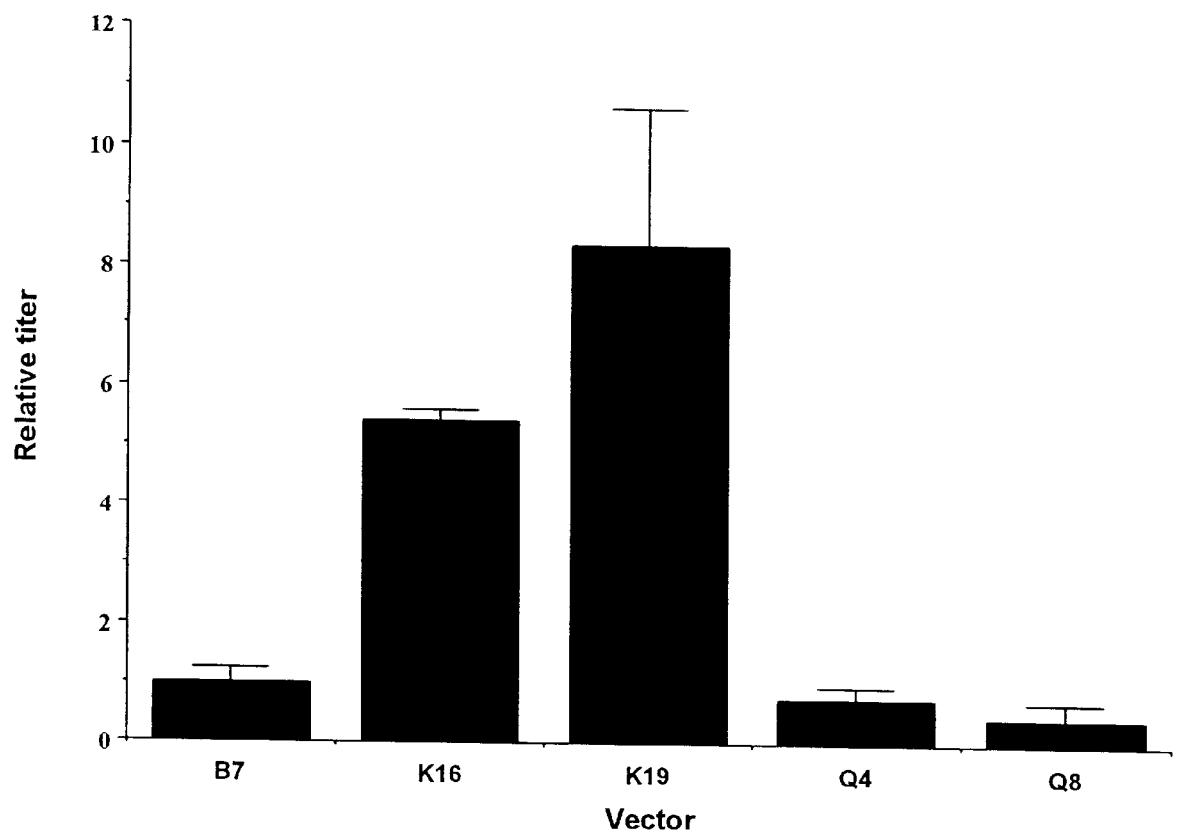

FIG. 17 is a bar graph depicting the relative retrovirus vector titers for new versions of the HERA tribrid vector. The retrovirus component of the HERA vector (B7) was modified to incorporate a hybrid CMV-LTR promoter at the 5'-end, and inserted in the HER backbone in two different orientations (HERAC K16, K19). A bidirectional cassette designed for expression of the retrovirus structural genes and vector component from the same promoter was also inserted in two directions in the hybrid HSV/EBV amplicon (BiHERA Q4, Q8). Retrovirus titers were determined at 48 hours post-transfection of 293T/17 cells.

Figure 18:
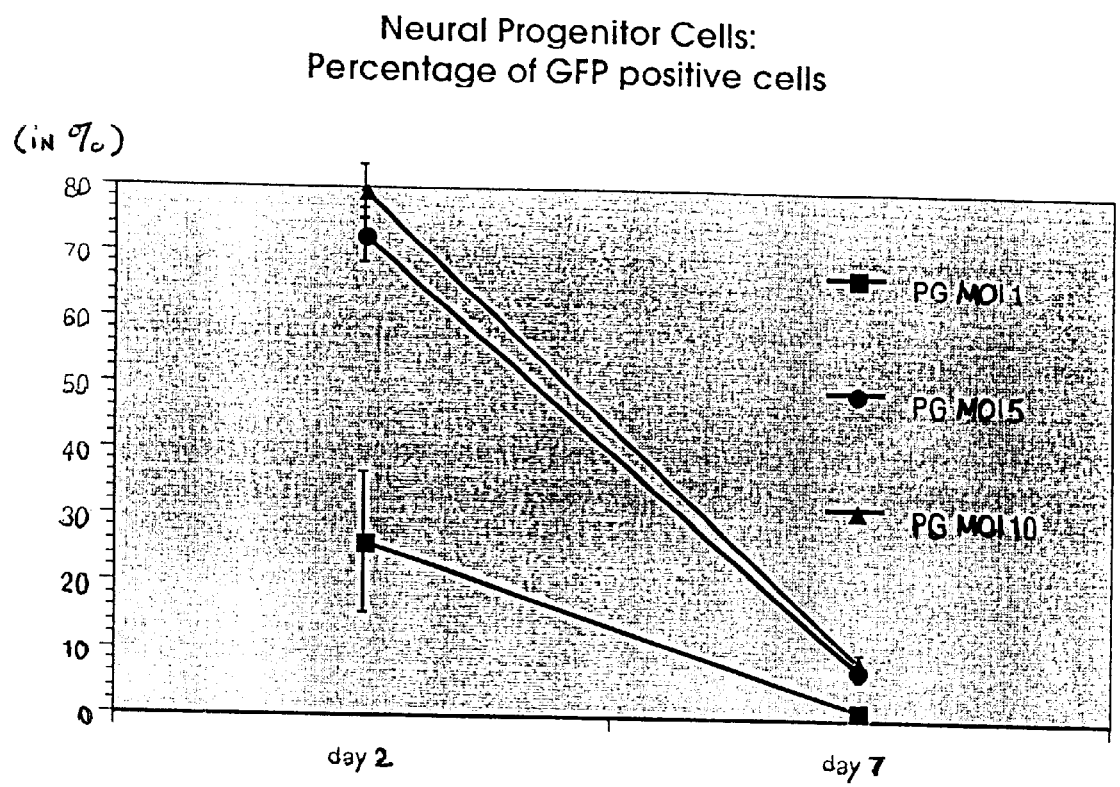

FIG. 18 is a graph depicting the percentage of green fluorescent protein (GFP)-positive cells measured by fluorescence-activated cell sorting (FACS) analysis at day 2 and day 7 following the infection of $5 \times 10^5$ human neural progenitor cells (H1) with the tribrid amplicon B7 at a MOI of 1, 5, and 10. The graph shows an expected loss of the amplicon DNA mediated GFP expression from cells over 5 days.

Figure 19:
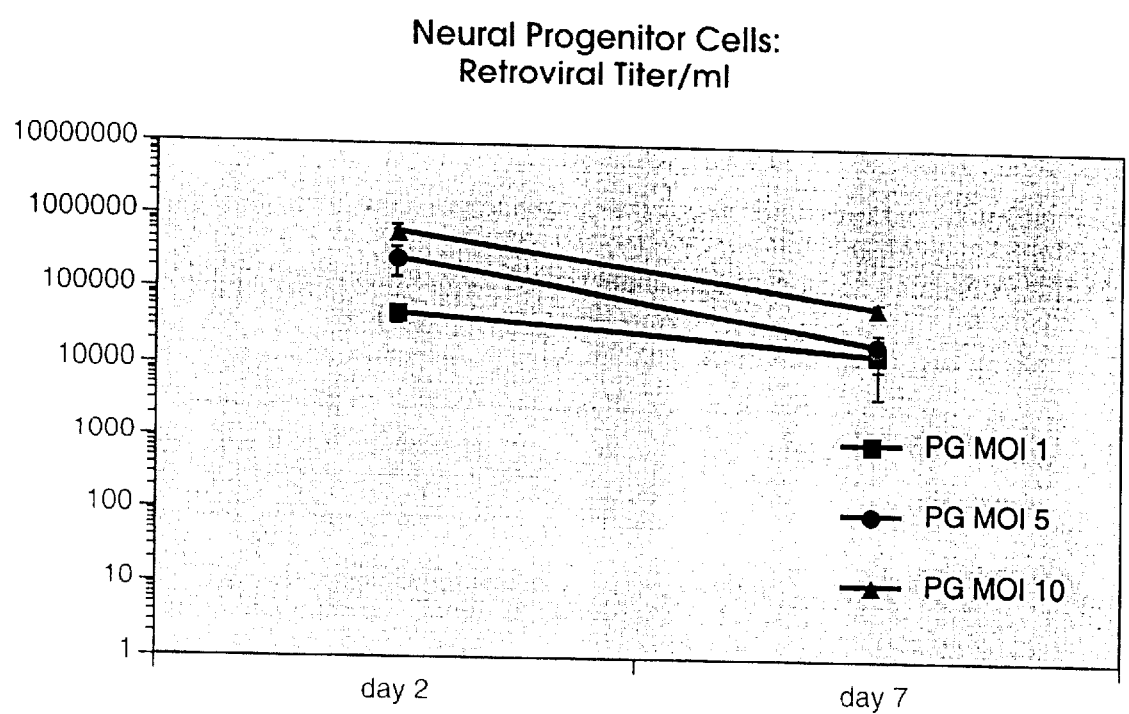

FIG. 19 is a graph depicting the high titer production of retrovirus vectors ($10^6$ tu/ml) by neural progenitor cells infected with the tribrid amplicon vector B7. At day 2 and day 7, NIH 3T3 cells were infected with supernatant from amplicon-infected HI cells. Forty-eight hours after infection, NIH 3T3 cells were stained with X-Gal solution and retroviral titers were determined. Although the retroviral titer decreased over time, it was still significant after 7 days ($10^5$ tu/ml) at MOI initial amplicon infection of 10.

FIGS. 20A–20E are photographs depicting dog glioma cells (J3TI) infected with the B7 or C1 hybrid amplicons at a MOI of 2. Twenty-four hours post-infection, the transduction efficiency was determined by FACS analysis (GFP positive cells). Subsequently B7-infected and non-infected glioma cells were mixed in a ratio of 5%/95%, 10%/90%, 20%/80% and 40%/60%. As a control, C1-infected cells were mixed with non-infected cells in a ratio of 40%/60%. Subsequently, $5 \times 10^6$ cells were injected subcutaneously into nude mice. The animals were sacrificed 10 days later (tumor volume ranged from 90–145 mm$^3$). Using a cryostat, the tumor was cut into 50 µm sections and stained with X-gal.

Figure 20A:
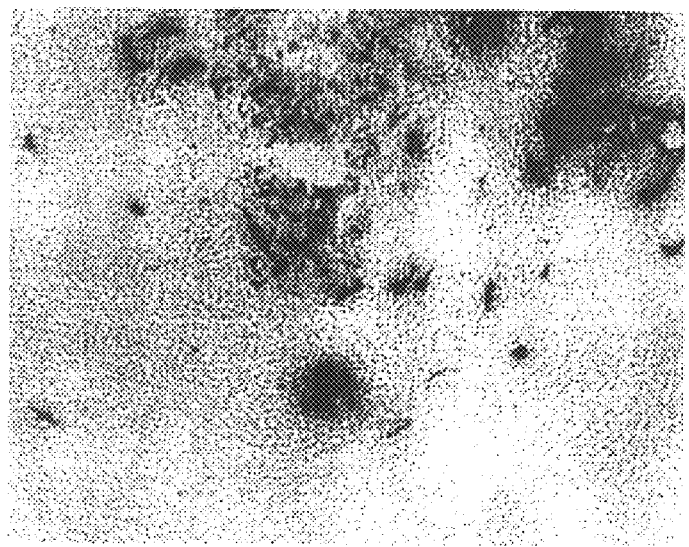

FIG. 20A is a photograph depicting tumor derived from a mixture of tribrid amplicon C1-infected J3T I cells with non-infected J3T I cells, in a ratio of 40%/60%. Only a few lacZ positive cells could be detected in the center of the tumor. The loss of transgene expression (40% to less than 10% of tumor) is expected as lacZ is carried only in the amplicon backbone, which is lost over time.

Figure 20B:
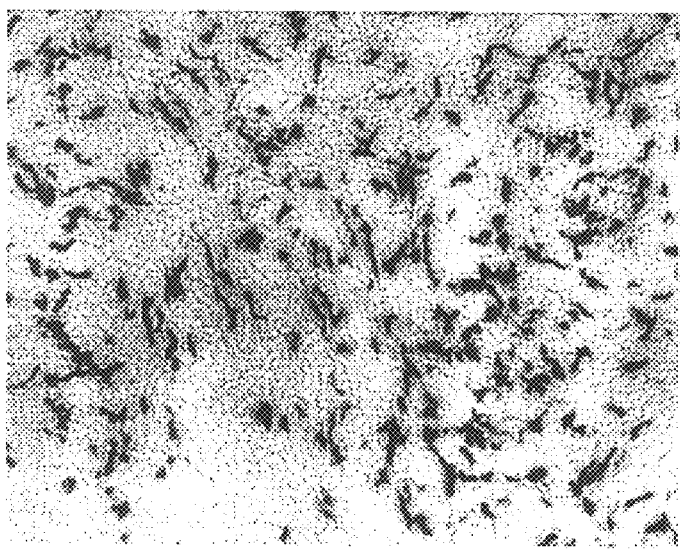

FIG. 20B is a photograph depicting tumor derived from a mixture of tribrid amplicon B7-infected J3T I cells with non-infected J3T I cells, in a ratio of 5%/95%. In contrast to the control C1 tumors (FIG. 20A), lac Z positive cells were abundant, and equally distributed throughout the tumor. Since even fewer lacZ-positive cells were initially injected here in comparison to the C1 experiment above (5%/95% vs. 40%/60%), the large number of lacZ cells observed in FIG. 20B indicated retrovirus mediated transfer of lacZ and transmission to daughter cells.

Figure 20C:
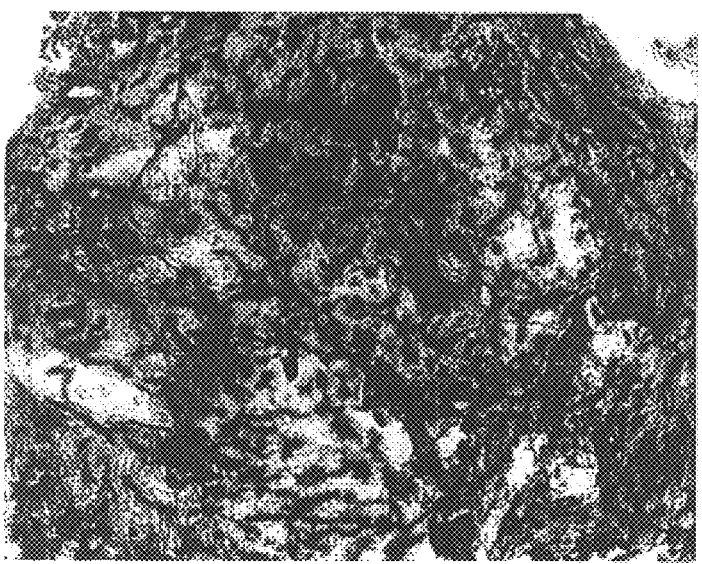

FIG. 20C is a photograph depicting tumor derived from a mixture of tribrid amplicon B7-infected J3T I cells with non-infected J3T I cells, in a ratio of 10%/90%. With the increased concentration of amplicon cells, the abundance of transgene positive cells increased dramatically. The inventors estimate that at least 50% of tumor cells are transgene positive with long-term expression.

Figure 20D:
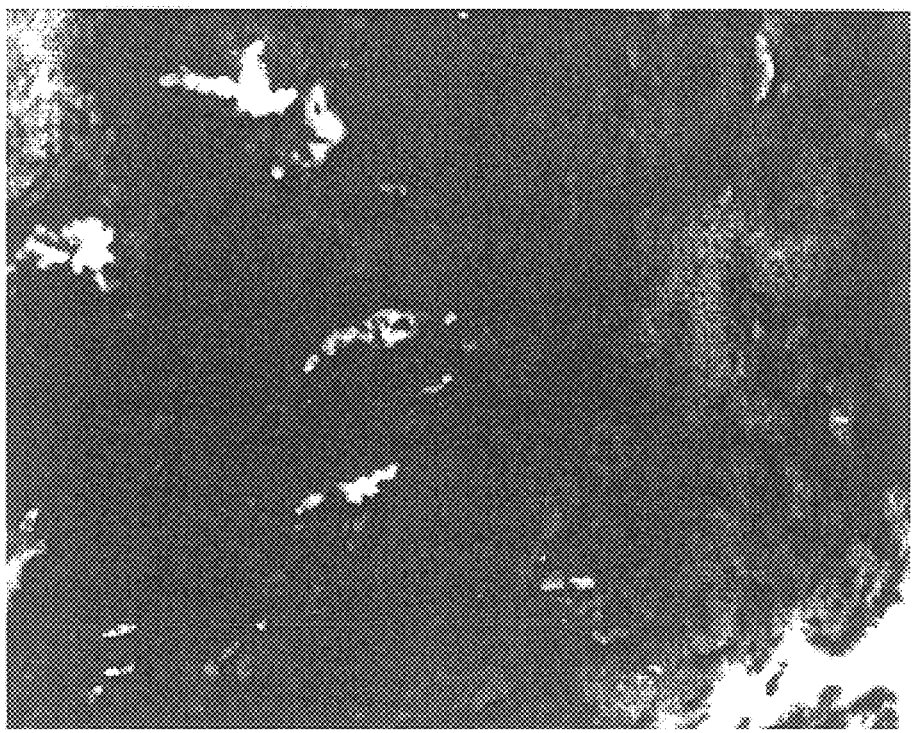

FIG. 20D is a photograph depicting tumor derived from a mixture of B7-infected J3T I cells with non-infected J3T I cells, in a ratio of 20%/80%. When 20% of the initial tumor population bears the retrovirus-producing amplicon, virtually the whole tumor becomes positive over 10 days of growth in vivo.

Figure 20E:
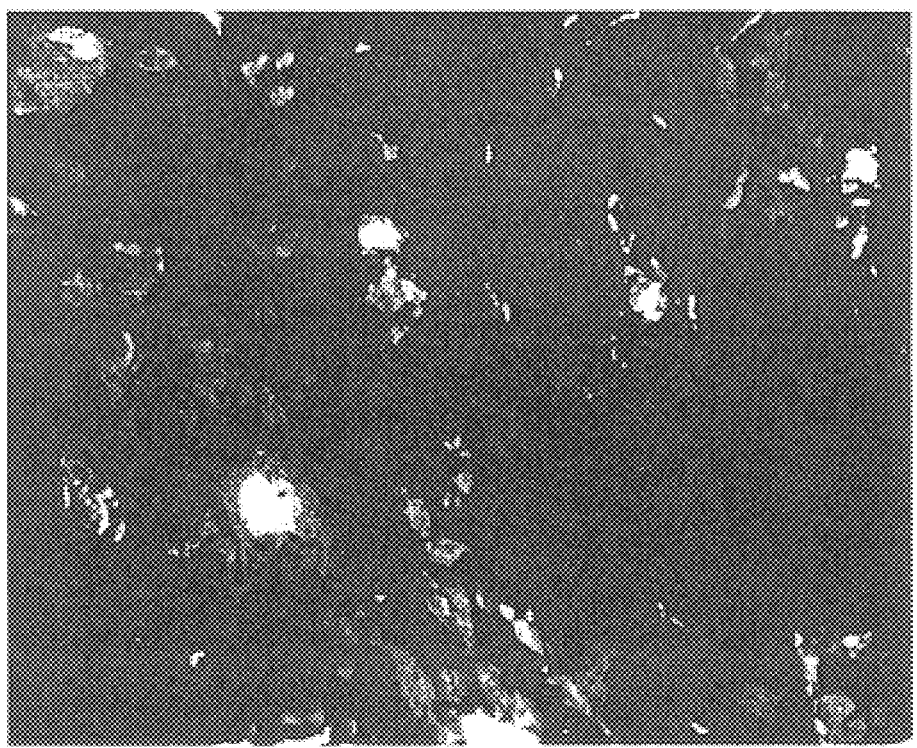

FIG. 20E is a photograph depicting tumor derived from a mixture of B7-infected J3T I cells with non-infected J3T I cells, in a ratio of 40%/60%. With the increasing percentage of cells bearing the retrovirus-producing amplicon vector, successive infections with the retrovirus vectors give multiple transgene copies per cell, and hence higher levels per cell of lacZ expression. Such an increased dose per cell could lead to increased therapeutic potential of the transgene.

Figure 21A:
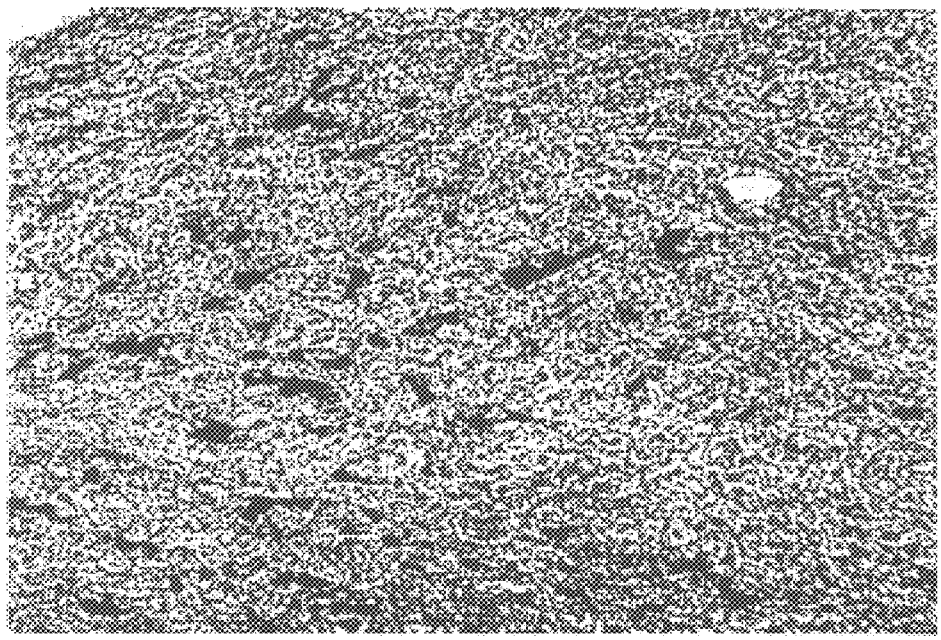
Figure 21B:
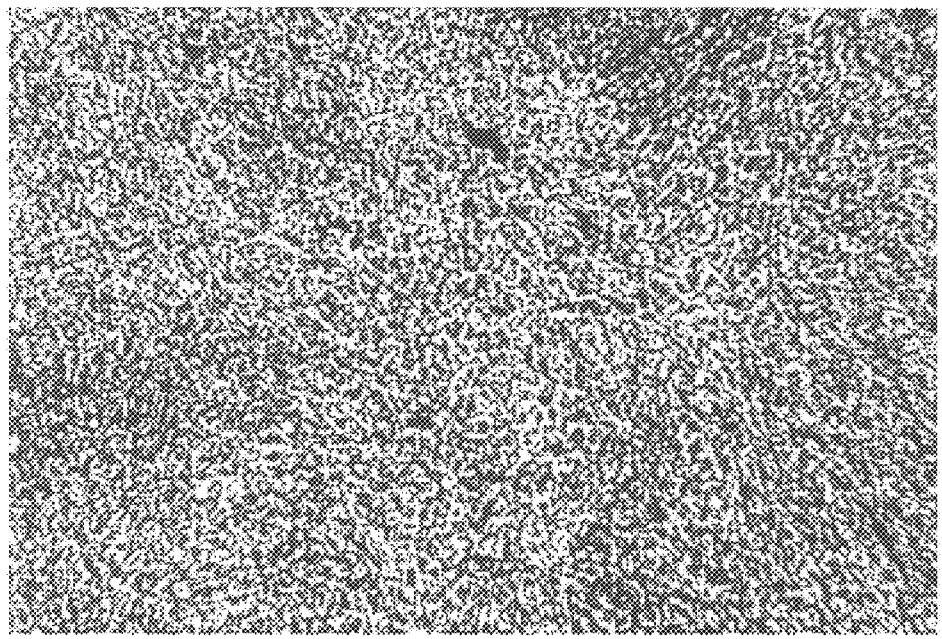

FIG. 21A–21B are photographs depicting the results of injecting tribrid amplicons B7 and C1 (control) into subcutaneous gliomas ($5 \times 10^6$ cells in 100 µl) established in the flanks of nude mice.

After the tumor reached a size of about 100 mm$^3$, either 10 ml of B7 (Tribrid Amplicon, Titer $3.14 \times 10^8$ tu/ml) or 10 µl of C1 (Control Amplicon, Titer $2.18 \times 10^8$ tu/ml) were infused into the tumor over a 10 minute period as a single injection. The animals were sacrificed 10 days later. Using a sliding microtome, the tumors were cut into 20 mm sections and stained with X-gal.

FIG. 21A is a photograph depicting tumor injection with B7 amplicons. Numerous lacZ positive cells are concentrated around the needle tract. In comparison to the control injection with C1 (FIG. 21B), this indicated successful secondary retroviral infection of tumor cells.

FIG. 21B is a photograph depicting tumor injection with the control C1 amplicons. Only a few lacZ positive cells are visible around the needle tract.

DETAILED DESCRIPTION OF THE PREFERRED EMBODIMENTS

The triple hybrid amplicon vector systems of the present invention were designed to combine the advantages of four different viruses that have previously been used for gene transfer and gene therapy: HSV, EBV or AAV, and retrovirus. Each of the amplicon vector systems of the invention are capable of converting both dividing and non-dividing cells into retrovirus packaging cells in one or two steps.

In a first embodiment of the invention, the hybrid amplicon vector comprises elements from HSV, EBV, and a retrovirus. In a preferred embodiment, the hybrid amplicon vector comprises: (a) an HSV origin of replication (ori S); (b) an HSV packaging signal (pac); (c) an EBV origin of replication (ori P); (d) an expression cassette of the EBNA-1 protein of EBV; (e) gag, pol, and env genes of a retrovirus; and (f) retroviral vector sequences, containing at least one transgene of interest.

Of course, other genetic elements may also be present in the amplicon portion of the construct, such as additional regulatory, therapeutic, reporter, or marker genes. That is, the hybrid amplicon packaging vector (HSV/EBV/retrovirus) can bear multiple transgenes both in the retrovirus vector element and in the amplicon backbone. Genes particularly suited for inclusion in the amplicon backbone, include: 1) marker genes to follow the fate of the packaging cells; 2) therapeutic genes to enhance the efficacy of those incorporated in the retrovirus vector or as an independent cache of additional therapeutic genes which would might be effective or best expressed over a limited period; 3) regulatory elements or genes, for example encoding drug/hormone inducible systems, such as the tetracycline transactivator and silencing proteins (Freundlieb, S., et al., *Methods Enzymol.* 283:159–173 (1997)) or dimerizing system (Amara, J. F., et al., *Proc. Natl. Acad. Sci. USA* 94:10618–10623 (1997)); and 4) genes for proteins which can reduce the immunogenicity of the packaging cell line. Examples of ways to reduce the immune response would be to incorporate in the amplicon certain immune-modulatory molecules, such as those that tumors use to evade the immune system, e.g., CD95 ligand, transforming growth factor-β, interleukin-10 (Hahne, M., et al., *Science* 274:1363–1366 (1996)).

HSV Elements for Determining Cell tropism and Copy Number:

The genetic elements in the HSV amplicon comprise at least: (1) the HSV origin of DNA replication (ori S); and (2) the virion packaging signal (pac). These elements permit the system to be packaged as an amplicon vector in HSV virions. The cell tropism of this system is then determined by the surface glycoproteins present in all HSV virions. In addition, as with all amplicons, they are able to enter and mediate gene expression both in dividing and non-dividing cells. This property is determined by the tegument and capsid proteins of HSV, which mediate transport to the nucleus and subsequent transfer of the encapsidated DNA into the nucleus.

Another property of this system, which also results from using HSV elements, is that like all amplicons, it is packaged in the virions as a concatamer with multiple copies of the amplicon. Since this amplicon is 20–30 kb and the HSV capsid always encapsulates 150 kb of DNA, each virion that carries this amplicon should deliver to cells at least five intact copies of this retrovirus packaging system. This means that each time a cell is infected, this corresponds to a multiplicity of infection of five.

EBV Elements for Improved Retention of the Packaging System, Leading to More Stable Expression of the Transgenes Encoded in the HybridAmplicon:

The elements from EBV comprise at least: (1) the EBV origin of DNA replication (ori P); and (2) the expression cassette of the EBNA-1 protein of EBV. One of the major problems in gene therapy, as mentioned before in the background section, is the retention of the genetic elements that are introduced by the various vectors. By "retention" of the genetic elements is intended the continued presence in transduced cells for more than four generations in dividing cells, and more than one month in non-dividing cells. Although HSV amplicon vectors can be very useful for gene transfer experiments, since they infect efficiently both dividing and non-dividing cells, and even more so after the advent of systems to package them without helper virus, they have a serious limitation which is their transient nature. Several systems have been devised to address this issue and the present system takes advantage of one of them: to combine HSV amplicons with the EBV oris P and EBNA-1 protein. This combination has been shown to result in a much longer retention time of the recombinant DNA to a point that stable gene expression is no longer out of place when referring to amplicons. The way these hybrids work is that after the amplicon DNA is transferred into the nucleus, it circularizes (which is typical for all amplicons), and then the EBNA-I protein and the oris P mediate replication and maintenance of the DNA in the cell nucleus.

Retroviral Elements for Spreading of the Transgene.

The genetic elements from retrovirus comprise at least: (1) the gag, pol, and env genes, which provide the retroviral packaging functions; and (2) retroviral vector sequences, which carry at least one transgene of interest and the psi packaging signal for incorporation in a retrovirus vector. By "spreading of the transgene" is intended the delivery to cells in the population not initially infected with the amplicon vector. The retroviral gag gene codes for core proteins, the pol gene codes for reverse transcriptase, and the env gene codes for the viral envelope protein.

In a particularly preferred embodiment, the retrovirus is Moloney Murine Leukemia Virus (MoMLV), which is a retrovirus that can only integrate genes into dividing cells. The ability of MoMLV to integrate only dividing cells may be an advantage in some situations, such as tumors, by restricting gene delivery to dividing cells. For many other applications, however, it reduces the spectrum of applications to developmental stages or organs and tissues where cell division takes place in the adult. Thus, to bypass this limitation, the present vector system can be modified to use lentivirus components (a subclass of retroviruses), in lieu of MoMLV components. Since lentiviral vectors are capable of infecting non-dividing cells as well as dividing cells, the use of lentiviral components in the vectors of the invention can therefore expand the applications of this gene delivery system.

The lentiviral components may be derived from the human immunodeficiency virus (HIV), with safety considerations being addressed by the elimination of some or all of the viral sequences non-essential for transduction. For a review of the use of lentiviruses as gene therapy vectors, see, Naldini, L., Curr. Opin. Biotechnol. 9:457–463 (1998); Kafri, T., et al., Nat. Genet. 17:314–317 (1997); and Naldini, L., et al., Science 272:263–267 (1996)).

Of course, elements from other retroviruses known to the skilled artisan can also be utilized in the hybrid vectors of the invention.

Due to its non-lytic manner of replication, retroviruses are the most suitable viruses to be part of a self-sustained in vivo gene delivery system. The retrovirus elements were all modified to reduce the overlapping sequences between the retrovirus gag, pol, and env genes, and the retrovirus vector, in order to avoid any recombination events that could generate wild-type virus. For this purpose, the gag, pol, and envelope cassette was modified to terminate at the TGA codon of the envelope gene. The 5' untranslated region of this cassette was kept intact so that the delicate balance of the splicing mechanism that originates the message that codes for the envelope gene was not affected. The retrovirus packaging signal is deleted in this cassette, which was derived from the MOVψ(–) vector (Mann, R., et al., Cell 33:153–159 (1983)). The retrovirus vector was also modified so that it only includes retrovirus sequences near the 3' LTR that are essential and do not overlap with the envelope gene. This way there are no sequences at the 3' end of the vector that overlap with any part of the expression cassette. The area around the packaging signal was also modified to minimize overlap with the gag-pol-env cassette. Most retrovirus nowadays not only include the packaging signal but they also extend into the 5' area of the gag region since it has been shown that it increases retrovirus titers. In the present system, this gag extension was deleted with no apparent effect on retrovirus titers when compared to the parental vector. This was done so that there are no overlapping sequences on both sides of the packaging signal which could mediate recombination. In this way, the homology between the gag-pol-env expression cassette and the retrovirus vector was reduced to a small 100 bp region at the 5' end.

Figure 1:
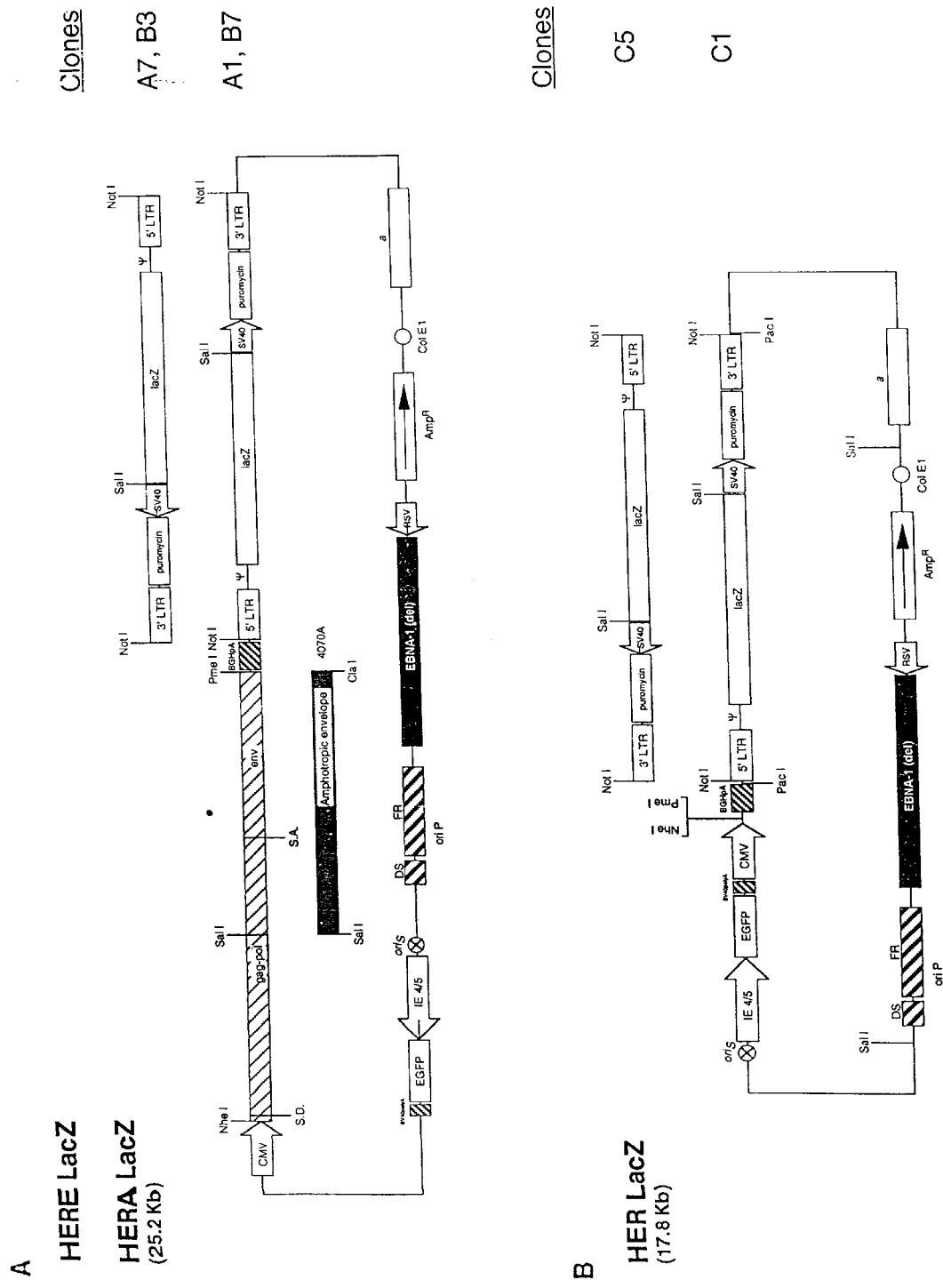
FIG. 1A and 1B depict the amplicon constructs of the invention that contain EBV elements.

In a particularly preferred embodiment of the HSV/EBV/ retrovirus vector embodiment, the hybrid vectors are HERE and HERA. These vectors are depicted in FIG. 1. As will be detailed in Example 1, the HERE system carries an ecotropic envelope (env) gene which can only efficiently infect rodent cells. The HERA system carries the amphotropic envelope gene derived from the 4070A MoMLV virus, and is able to infect a wide spectrum of mammalian cells.

In a second embodiment, the hybrid amplicon vector of the invention comprises elements from HSV, AAV, and a retrovirus. In a preferred embodiment, the hybrid amplicon vector comprises: (a) an HSV origin of replication (ori S); (b) an HSV packaging signal (pac); (c) an AAV rep gene; (d) an AAV ITR element; (e) gag, pol, and env genes of a retrovirus; and (f) retroviral vector sequences, containing at least one transgene of interest.

Of course, other genetic elements may also be present in the amplicon portion of the construct, such as additional regulatory (i.e., promoter), therapeutic, reporter, or marker genes. That is, the hybrid amplicon packaging vector (HSV/ AAV/retrovirus) can bear multiple transgenes both in the retrovirus vector element and in the amplicon backbone. Genes particularly suited for inclusion in the amplicon backbone, include: 1) marker genes to follow the fate of the packaging cells; 2) therapeutic genes to enhance the efficacy of those incorporated in the retrovirus vector or as an independent cache of additional therapeutic genes which would might be effective or best expressed over a limited period; 3) regulatory elements or genes, for example, encoding drug/hormone inducible systems, such as the tetracycline transactivator and silencing proteins (Freundlieb, S., et al., Methods Enzymol. 283:159–173 (1997)) or dimerizing system (Amara, J. F., et al., Proc. Natl. Acad. Sci. USA 94:10618–10623 (1997)); and 4) genes for proteins which can reduce the immunogenicity of the packaging cell line. Examples of ways to reduce the immune response would be to incorporate in the amplicon certain immune-modulatory molecules, such as those that tumors use to evade the immune system, e.g., CD95 ligand, transforming growth factor-β, interleukin-10 (Hahne, M., et al., Science 274:1363–1366 (1996)).

The genetic elements from HSV and the retrovirus were discussed above. In this embodiment, though, rather than using EBV elements, elements from AAV are utilized in the amplicon vector. Both EBV and AAV viruses have elements known to sustain or bind the DNA elements in the host cell nucleus. The EBV elements (ori P and EBNA-1) mediate episomal replication and chromosomal retention at mitosis; the AAV elements (ITRs and rep gene) mediate replicative amplification of ITR flanked elements and chromosomal integration.

AAV Elements for Improved Retention of the System, Leading to More Stable Expression of the Transgene.

The genetic elements from AAV comprise at least: (1) the terminal repeats, ITRs, which are sufficient for replication and packaging of AAV virions; and (2) the rep gene, which encodes Rep isozymes involved in replication and chromosomal integration of the ITR-flanked sequences. These elements have the potential to mediate transgene amplification and stabilization, as well as chromosomal integration of the transgene with viruses that normally do not possess this property. The ITRs plus the Rep isozymes are thought to mediate site-specific integration into human chromosome 19q as well as random integration; the ITRs alone can mediate random integration.

AAV has a broad host range and until recently, all human cells were thought to be injectable. The host range for integration is believed to be equally broad and includes non-human species. AAV is a single-stranded DNA parvovirus endogenous to the human population, making it a suitable gene therapy vector candidate. AAV is not associated with any disease, therefore making it safe for gene transfer applications (Cukor et al., The Parvoviruses, ed., K. I. Berns, Plenum, N.Y., pp. 33–36 (1984); Ostrove, J. M., et al., *Virology* 113: 521–533 (1981)). AAV integrates into the host genome upon infection so that transgenes can be expressed indefinitely (Kotin, R. M., et al., *Proc. Natl. Acad. Sci. USA* 87: 2211–2215 (1990); Samulski, R. J., et al., *EMBO J.* 10: 3941–3950 (1991)). Integration of AAV into the cellular genome is independent of cell replication which is particularly important since AAV can thus transfer genes into quiescent cells (Lebkowski, J. S., et al., *Mol. Cell. Biol.* 8:3988–3996 (1988)).

In a particularly preferred embodiment of the HSV/AAV/retrovirus vector embodiment, the hybrid vectors are HyR-MOV Ampho and HyBPlacZ. These vectors are depicted in FIGS. 8A and 8B, respectively.

The inserted transgene in the retroviral vector of either triple hybrid amplicon vector may be a reporter or marker gene, and/or a therapeutic gene. A "triple hybrid amplicon vector", as used herein, is a nucleic acid molecule (preferably DNA) in which a gene sequence, or a transgene, is fused to a subset of viral sequences from (1) Herpes Simplex Virus (HSV); (2) Epstein-Barr Virus (EBV) or Adeno-Associated Virus (AAV); and (3) retrovirus, such that the amplicon vector is capable of generating retrovirus packaging cells. The term "retrovirus packaging cells," as used herein, refers to mammalian cells which are capable of producing retrovirus vectors.

The term "transgene," as used herein, is intended to refer to a gene sequence, and is a nucleic acid molecule. Such transgenes, or gene sequences, may be derived form a variety of sources including DNA, cDNA, synthetic DNA, RNA, or combinations thereof. Such transgenes may comprise genomic DNA, which may or may not include naturally occurring introns. Moreover, such genomic DNA may be obtained in association with promoter regions or poly A sequences. The transgenes of the present invention are preferably genomic DNA or cDNA. Genomic DNA or cDNA may be obtained by means well known in the art. One or more transgenes may be present in the vector constructs of the invention.

The transgene may be any gene sequence whose expression produces a gene product that is to be expressed in a cell. The gene product may affect the physiology of the host cell, and/or may be therapeutic. Examples of gene sequences that can be used as therapeutic trangenes, include, but are not limited to, a gene sequence associated with diseases and disorders such as inherited metabolic disorders, including, lysosomal storage disease, Lesch-Nyhan syndrome, inherited neurological diseases, including, amyloid polyneuropathy, Alzheimer's Disease, Duchenne's muscular dystrophy, ALS, Parkinson's Disease and brain tumors, diseases of the blood, such as, sickle-cell anemia, clotting disorders and thalassemias, cystic fibrosis, diabetes, disorders of the liver and lung, heart and vascular disease, diseases associated with hormone deficiencies, movement disorders, pain, stroke, HIV and cancer.

For disease and disorders listed above that are considered deficiency state diseases, gene therapy could be used to bring a normal gene into affected tissues for replacement therapy, as well as to create animal models for the disease using antisense mutations.

Thus, the invention also provides for a hybrid amplicon vector wherein the inserted transgene sequence is a gene sequence associated with diseases and disorders. Non-limiting examples of such diseases and disorders are listed above.

The term "transgene cassette," as used herein, is intended to refer to a transgene operably linked to a promoter or other regulatory sequence sufficient to direct transcription of the transgene. Suitable promoters include, for example, a human CMV IEI promoter or an SV40 promoter, or mammalian or prokaryotic promoters well known to those skilled in the art. The transgene cassette may also optionally have termination signals, processing signals, or introns. It is of course possible to use as a transgene a gene sequence that already possesses a promoter, initiation sequence, introns, processing sequence or termination sequence in the transgene cassette.

Alternatively to using one or more therapeutic trangenes, or in addition to using one or more therapeutic transgenes in the vectors of the invention, the vectors may also contain one or more non-therapeutic transgenes, such as reporter genes or selectable marker genes.

A "reporter gene," as used herein, is any gene sequence which, when expressed, results in the production of a protein whose presence or activity can be easily monitored. Examples of suitable reporter genes can include the gene for β-galactosidase, green fluorescent protein, galactokinase, alkaline phosphatase, chloramphenicol acetyltransferase, luciferase, and β-lactamase.

A "selectable marker gene," as used herein, is any gene sequence capable of expressing a protein whose presence permits selective propagation of a cell which contains it. Examples of selectable markers include gene sequence capable of conferring host resistance to antibiotics (such as ampicillin, tetracycline, kanamycin, etc.), amino acid analogs, or permitting growth of bacteria on additional carbon sources or under otherwise impermissible culturing conditions.

The term "host cell" is intended to refer to any cell that can be infected with the hybrid amplicon vectors of the present invention. Mammalian cells are preferred host cells.

The term "operably linked" is intended to describe a linkage between a gene sequence and a promoter or other regulatory or processing sequence such that the transcription of the gene sequence is capable of being directed by an operably linked promoter sequence, the translation of the gene sequence is capable of being directed by an operably linked translational regulatory sequence and the post-translational processing of the gene sequence is capable of being directed by an operably linked processing sequence.

The invention further provides a method for expressing a transgene in a proliferating cell population, in vitro or in vivo, using the hybrid vectors of the invention. Some exemplary in vivo applications for the gene delivery system of the invention include gene delivery to the central nervous system during neurogenesis and gliogenesis, gene delivery to the bone marrow for the correction of genetic disorders as well as to protect the bone marrow from infection (as in HIV-infected individuals or other immune deficient individuals), gene delivery to the developing liver, and gene delivery to the lung during development.

The invention also provides a method of treating diseases and disorders using the hybrid vectors of the invention.

Non-limiting examples of the diseases and disorders that can be treated using the present hybrid vectors include: inherited metabolic disorders, including, lysosomal storage disease, Lesch-Nyhan syndrome, inherited neurological diseases, including, amyloid polyneuropathy, Alzheimer's Disease, Duchenne's muscular dystrophy, ALS, Parkinson's Disease, diseases of the blood, such as, sickle-cell anemia, clotting disorders and thalassemias, cystic fibrosis, diabetes, disorders of the liver and lung, heart and vascular disease, diseases associated with hormone deficiencies, movement disorders, pain, stroke, HIV, tumors, neoplasms, carcinomas, sarcomas, leukemias, lymphoma, astrocytomas, oligodendrogliomas, meningiomas, neurofibromas, ependymomas, Schwannomas, neurofibrosarcomas, and glioblastomas.

In yet another embodiment, the invention provides a method of selectively killing neoplastic cells using the hybrid vectors of the invention. Gene therapy can be used to introduce a gene into the tumor cells that expresses a protein which is toxic or can trigger a toxic effect against tumor cells. Genes for transfer into the neoplastic cells by the hybrid vectors are selected from those which target host cell usually by expression of a gene product in the host neoplastic cells. "Gene product" broadly refers to proteins encoded by the particular gene. For the purposes of the invention, gene product also includes transcription products of the gene, particularly for use as antisense RNA. Genes are selected whose gene products serve to identify host cells, slow down or temporarily stimulate host cell growth in order to render the host cell more sensitive to chemotherapeutic agents and/or whose products target the host cell for cell death. Cell death can be accomplished by contacting the host cells, containing the gene product, with a subsequent treatment, either physical or chemical treatment. Alternatively, the gene products themselves may serve to kill the host cells or slow down cell growth. The host cells targeted by the present hybrid vectors are those cells into which the hybrid vector infects and expresses the desired gene product and thus can constitute neoplastic cells infected by the hybrid vectors.

Useful gene products comprise: tumor suppressor genes, which encode transcription factors which suppress cell growth, such as the Rb gene for retinoblastoma or the p53 gene in colon cancer (Huang, H. J., et al., *Science* 242: 1563–1566 (1988); Baker, S. J., et al., *Science* 249: 912–915 (1990)); toxic proteins that are released by cells, such as a fusion protein comprising a toxin coupled to EGF ligand (Heimbrook, D. C., et al., *Proc. Natl. Acad. Sci. USA* 87: 4697–4701 (1990)); products which themselves trigger apoptosis or are capable of selective cell killing or growth inhibition, such as anti-sense nucleic acid for essential cell proteins, and replication proteins which serve to render the host cells incapable of further cell growth and division (Rosenberg, U. B., et al., *Nature* 313: 703–706 (1985); Preiss, A, et al., *Nature* 313:27–32 (1985); McGarry, T. J., et al., *Proc. Natl. Acad. Sci USA* 83: 399–403(1986)); prodrug activating genes such as HSV thymidine kinase (TK) (Kramm, C. M., et al., *Brain Pathology* 5:345–381 (1995); Ezzeddine, Z. D., et al., *New Biol.* 3:608–614 (1991)), cytosine deaminase (CD) (Mullen, C. A., et al., *Proc. Natl. Acad. Sci. USA* 89: 33–37 (1992); Huber, B. E., et al., *Cancer Res.* 53:4619–4626(1993); Mullen, C. A., et al., *Cancer Res.* 54:1503–1506 (1994)), or cytochrome P450 (Chen, L. and Waxman, D. J., *Cancer Research* 55:581–589 (1995); Wei, M. X., et al., *Hum. Gene Ther.* 5:969–978 (1994)); and genes encoding proteins that block angiogenesis (O'Reilly, M., et al., *Cell* 88:277–285(1997)).

For example, a triple hybrid amplicon vector which incorporates the HSV-1 thymidine kinase gene offers such a conditional killing mechanism for dividing cells. The thymidine kinase enzyme can convert certain nucleoside analogues, such as, acyclovir, ganciclovir, and FIAU. These drugs are converted to nucleotide-like precursors and incorporated into the DNA of the replicating cells, thus disrupting the integrity of the genome and ultimately leading to cell death. (See, Boviatsis, E. J., et al., *Cancer Res.* 54:5745–5751 (1994). Thus, the hybrid vector administered in combination with a less toxic drug could be highly effective treatment for tumors.

In addition, the hybrid vector can also incorporate the gene for cytochrome P450. The cytochrome P450 gene offers a conditional killing mechanism independent of the cell cycle of the tumor cell. This gene is used to sensitize neoplastic cells to the cytotoxic effects of a chemotherapeutic agent that is activated by one or more cytochrome P450 genes. The term "cytochrome P450 gene," as used herein, means a mammalian cytochrome P450 gene such as, P450, 2B1, P450 2B6, P450 2A6, P450 2C8, P450 2C9, P450 2C11, or P4503A4. Each of these genes has been linked to activation of the anticancer drugs cyclophosphamide, oxazaphophorine or ifosphamide (Clarke, L., et at., *Cancer Res.* 49:2344–2350 (1989); Chang, TKH, et al., *Cancer Res.* 53:5629–5637 (1993); Weber, G. F., et al., *Biochemical Pharmacology* 45:1685–1694 (1993), and the cDNA sequences of these genes have also been published (Nelson, D. R., et al., *DNA and Cell Biology* 12:1–51 (1993) and references cited therein; Yamano, S., et al., *Biochem.* 29:1322–1329 (1990); Yamano, S., et al., *Biochem.* 28:7340–7348(1989). Persons of ordinary skill in the art will be able to utilize the method and vectors of the present invention with numerous other anticancer drugs that are activated by members of the cytochrome P450 family of enzymes that are homologous to the aforementioned cytochromes.

In a preferred embodiment for selectively killing neoplastic cells, the cytochrome P450 2B1 gene is utilized to sensitize central nervous tumor cells to the cytotoxic effects of cyclophosphamide (CPA). Expression of cytochrome P450 2B1 gene in C6 glioma cells was found to lead to tumor cell destruction following CPA treatment in culture, in subcutaneous tumors in athymic mice, in MCF-7 human breast carcinoma cells and in experimental brain tumors in mice. The P450 2B1 gene has been successfully utilized to sensitize tumors cells such as 9 L gliosarcoma cells to oxazaphosphorine treatment.

In another embodiment, more than one prodrug-activating gene may be inserted in the hybrid amplicon vector systems of the invention, in order to achieve synergistic effects. For example, the HSV-TK gene coupled with the bacterial cytosine deaminase(CD) gene may be used together, as may the HSV-TK gene with a cytochrome P450 gene. Other combinations of prodrug-activating genes, known to those skilled in the art, may also be used in the vectors and methods of the invention. An overview on prodrug-activating genes (also called "suicide genes") for cancer gene therapy may be found in Freeman, S. M., et al., *Semin. Oncol.* 23:31–45 (1996).

The hybrid vector can be administered to the tumors in a mammal by multiple routes, including, e.g., direct injection into the tumor mass, through the blood vessels, via cerebrospinal fluid, or via an infected packaging cell.

The gene product may also encode a chemical or protein which renders the host cells radiosensitive and thus more susceptible to killing by radiation. Thus, upon subsequent subjection to radiation, the host cells are selectively killed.

Thus, the following types of cancers and tumors can be treated using the present hybrid vectors: neoplasms, carcinomas, sarcomas, leukemias, lymphoma, and the like. Of particular interest are central nervous system tumors which include astrocytomas, oligodendrogliomas, meningiomas, neurofibromas, ependymomas, Schwannomas, neurofibrosarcomas, glioblastomas, etc.

Thus, the invention further provides a method for expressing a transgene in a cell, which comprises:
(a) introducing an HSV/EBV/retrovirus hybrid amplicon vector into the cell; and
(b) permitting the vector to express the transgene in the cell.

In another embodiment, the invention provides a method for expressing a transgene in a cell, which comprises:
(a) introducing an HSV/AAV/retrovirus hybrid amplicon vector into the cell; and
(b) permitting the vector to express the transgene in the cell.

The invention also provides a method of selectively killing neoplastic cells comprising:
(a) infecting said neoplastic cells with a HSV/EBV/retrovirus hybrid amplicon vector or HSV/AAV/retrovirus hybrid amplicon vector expressing thymidine kinase, wherein expression of the thymidine kinase gene product renders said tumor cells sensitive to ganciclovir or acyclovir;
(b) administering an effective amount of ganciclovir or acyclovir; and
(c) selectively killing said tumor cells.

The invention also provides the foregoing method, wherein the HSV/EBV/retrovirus or HSV/AAV/retrovirus hybrid amplicon vector additionally expresses a second prodrug-activating gene, in addition to HSV-TK.

The invention further provides for a method of selectively killing neoplastic cells comprising:
(a) infecting said neoplastic cells with a HSV/EBV/retrovirus hybrid amplicon vector or HSV/AAV/retrovirus hybrid amplicon vector expressing cytochrome P450, wherein expression of the cytochrome P450 gene product renders said tumor cells sensitive to a chemotherapeutic agent;
(b) administering to the patient an effective amount of a chemotherapeutic agent that is activated by the cytochrome P450 enzyme; and
(c) selectively killing said tumor cells. In a preferred embodiment, the chemotherapeutic agent is cyclophosphamide or ifosphamide.

The invention also provides the foregoing method, wherein the HSV/EBV/retrovirus or HSV/AAV/retrovirus hybrid amplicon vector additionally expresses a second prodrug-activating gene, in addition to cytochrome P450.

The invention also provides a preferred embodiment of the foregoing vector wherein any of the above mentioned hybrid amplicon vectors are capable of generating retrovirus packaging cells in a single step. According to the invention, one or two hybrid amplicons can be used to deliver the retroviral vector components.

The present invention is further illustrated by the following examples. These examples are provided to aid in the understanding of the invention and are not construed as a limitation thereof.

EXAMPLE 1

Construction and Characterization of HSV/EBV Hybrid Amplicons

Materials and Methods

Cells: NIH 3T3 cells (CRL 1658) were obtained from the American Type Culture Collection (ATCC) (Manassas, Va.). 293T/17 cells (Pear, W. S., et al., *Proc. Natl. Acad. Sci. USA* 90:8392–8396 (1993)) constitutively express the SV40 large T antigen and clone 17 was specifically selected for its high transfectability. These cells were provided by Dr. David Baltimore at MIT, Cambridge, Mass. Phoenix-E cells were obtained from the ATCC. African green monkey kidney 2—2 cells (Smith, I. L., et al., *Virol.* 186:74–86 (1992)) were provided by Dr. Rozanne Sandri-Goldin(University ofCalifornia, Irvine, Calif.). The SNB-19humanglioma cell line (Gross, J. L., et al., *Cancer Res.* 48:291–296 (1988)) was obtained from the ATCC. T98 were obtained from Dr. F. S. Prado at MGH, Boston, Mass. U87.ΔEGFR (Nagane, M., et al., *Cancer Res.* 56:5079–5086 (1996)), was provided by Dr. Webster Cavenee at the University of California, San Diego. Gli-36-human primary glioma was provided by Dr. David N. Louis (MGH, Charlestown, Mass.). J3T dog glioma cell line (Berens, M. E., et al., *In Vitro Cell Dev. Biol. Anim.* 29A:310–318 (1993)) was provided by Dr. Michael E. Berens (Barrow Neurological Institute, Phoenix, Ariz.). The 9L rat gliosarcoma cell line (Weizsaecker, M., et al., *J. Neurol.* 224:183–192 (1981)) was obtained from the Brain Tumor Research Center (University of California, San Francisco). CNS-1 rat glioma cells (Kruse, C. A., et al., *J. Neurooncol.* 22:191–200 (1994)) were obtained from Drs. Kruse and Hickey (University of Colorado).

NIH 3T3 cells were grown in Dulbecco's modified Eagle's medium (DMEM) supplemented with 10% calf serum (Sigma, St. Louis, Mo.). 293T/17, Phoenix-E, SNB19, T98, U87.ΔEGFR, Gli-36, J3T, 9L, CNS-1 and 2—2 cells were grown in DMEM with 10% fetal bovine serum (Sigma). All medium was supplemented with 100 U/ml penicillin and 0.1 mg/ml streptomycin (Sigma). 2—2 and U87.ΔEGFR cells growth medium was further supplemented with 0.5 mg/ml G418 (GIBCO BRL, Gaithersburg, Md.). Cells were grown at 37° C. and 5% $CO_2$ in a humidified atmosphere.

Plasmids: All DNA sequences amplified by PCR were cloned in pCR2.1 vector using the TA cloning kit (Invitrogen, Carlsbad, Calif.) and sequenced.

1. Construction of gag-pol-env (GPE) Expression Cassette Primers used:
MOV-1: GCTAGCCCTCTTGCAGTTGCATCCGAC (SEQ ID NO:1)
Nhe I
MOV-2: AGGAGCAACTGGCGATAGTGGAC (SEQ ID NO:2)
ENVP3: TCTAGACTATGGCTCGTACTC (SEQ ID NO:3)
Xba I
ENVP4: CTGTTTAACAGATCCCCTTGG (SEQ ID NO:4)

The pMOVΨ⁻ plasmid (Mann, R., et al., *Cell* 33:153–159 (1983)), was used as a template for all PCR reactions. Primers ENV-P3 and ENV-P4 were used to amplify a 209 bp fragment which was cloned in pCR2.1 generating the plasmid, TVENVP34. A 6114 bp Xho I-Cla I fragment from pMOVΨ⁻ was then cloned into TVENVP34 generating the plasmid, TVMOV. A 6226 bp Xho I-Eco RI fragment from this plasmid was then cloned in pcDNA3. INeo(−) (Invitrogen) generating the plasmid, pcDNA3.1MOV. Primers MOV-1 and MOV-2 were used to amplify a 1237 bp fragment from pMOVΨ and the PCR product was cloned and sequenced. The 1161 bp Nhe I-Xho I fragment derived from this plasmid was then cloned in pcDNA3.MOV generating pcDNA3.1MOV 12.

To construct the amphotropic version, the 4070A amphotropic genome (Chattopadhyay, S. K., et al., *J. Virol.* 39:777–791 (1981)), was digested with Sal I and Cla I and the resulting 3936 bp fragment, containing the amphotropic envelope gene, was cloned into TVMOV, generating the plasmid TVMOV Ampho. The 6081 bp Xho I to Cla I fragment was cloned in pcDNA3.1MOV12 generating pcDNA3.1MOV Ampho.

2. Construction of Retrovirus Vector with Minimal Overlap with GPE Cassette

Primers used:

BAB-1:
  GCGGCCGCTGATCATTCCGCGCACATTTCCCCGA AAAG
  Not I (SEQ ID NO:5)
BAB-2:
  GTCGACAGATCTCAGCAGACAAGACGCGCGGCT TCGG
  Sal I Bgl II (SEQ ID NO:6)
BAB-4:
  ATGCATGCGGCCGCTGATCAAAATGAAAGACCCC CGCTGAC
  Nsi I Not I (SEQ ID NO:7)
BAB-5:
  ATCGATGTCGACATTAATGTCTCCAGAAAAAGGG GGGAATGAAAG
  Cla I Sal I (SEQ ID NO:8)

The retrovirus vector elements were derived from the vector pBabe Puro (Morgenstern, J. P., and J. Land, *Nucleic Acid Res.* 18:3587–3596 (1990)). BAB-1 and BAB-2 primers were used to amplify a 933 bp fragment spanning the 5' LTR and the packaging signal. This PCR product was cloned into pCR2.1, originating the plasmid TVBAB 12. BAB-4 and BAB-5 primers were used to amplify a 654 bp fragment spanning the 3' LTR which was cloned in pCR2.1 generating the plasmid TVBAB45. The Nsi I to Sal I fragment from this plasmid containing the BAB45 sequence was cloned in TVBAB 12 generating the plasmid TVB. The 1075 bp Sal I to Nhe I fragment from pBabe Puro containing the SV40 early promoter and puromycin selection marker gene were cloned in TVB generating the plasmid TVBP. The *Escherichia coli* lac Z gene was cloned in the Bgl II site of this plasmid.

3. Construction of HERE/HERA Vectors

The Nhe I to Pme I fragments from pcDNA3.1IMOV 12 and pcDNA3. 1MOV Ampho encompassing the coding sequences for the retrovirus proteins were cloned in the M12Y HSV/EBV hybrid amplicon generating the vectors pHERE and pHERA, respectively. The retrovirus vector element was derived from the TVBPlacZ plasmid after digestion with Not I and cloned into the unique Not I site of pHERE and pHERA.

Transfections and vector titer determination; Retrovirus packaging. 293T/17 and Phoenix-E cells were transfected essentially as described (Pear et al., *Proc. Natl. Acad. Sci. USA* 90:8392–8396 (1993)). The day before transfection, $2 \times 10^6$ 293T/17 cells were plated in 4 ml of medium on 60 mm dishes. The following day, the medium was replaced with medium containing 25 μM chloroquine (Sigma) 5 to 10 minutes before adding the DNA/calcium phosphate co-precipitates. 15 μg of each plasmid were mixed with 62 μl of 2 M $CaCl_2$ (Sigma) and water to a final volume of 500 μl. This solution was added to 500 μl of HEPES-buffered saline (HBS) (50 mM HEPES, 10 mM KCl, 12 mM dextrose, 280 mM NaCl, 1.5 mM $Na_2HPO_4$—final pH 7.05) and mixed by vigorous bubbling for 1 minute. The resulting suspension was immediately added to the cells and the plate gently rocked to achieve a uniform distribution of the precipitates. Cells were returned to the 37° C. incubator for 8 hours. The medium containing chloroquine was then replaced with 4 ml of growth medium. The following day, the medium was changed to 3 ml of fresh medium and the cells were incubated at 37° C. for 24 hours before harvesting.

Retrovirus titer determination. For all retrovirus titers determined in this study, the media from retrovirus vector producing cells was centrifuged at 500×g for 5 minutes and supernatants were stored at −80° C. One day prior to infection, NIH 3T3 cells were plated in 12 well dishes at a density of $5 \times 10^4$ cells/well. Cells were infected in a total volume of 0.5 ml containing different volumes of supernatant in the presence of 4 μg/ml polybrene (Sigma). Each vector stock was titered in triplicate. One day later, the total volume was brought up to 1 ml with fresh medium and incubated for 24 hours before fixation in 4% paraformaldehyde (Sigma) in phosphate-buffered saline (PBS)(Sigma) for 5 to 7 minutes at room temperature. Cells were washed twice with PBS and stained with X-Gal (5-bromo-4-chloro-indolyl-β-D-galactopyranoside, Fisher, Pa.) solution (1 mg/ml X-gal, 2 mM $MgCl_2$, 5 mM $K_4Fe(CN)_6$, 5 mM $K_3Fe(CN)_6$ in PBS) overnight. Positive cells were counted using a Argus-20 image processor (Hamamatsu Photonics, Hamamatsu City, Japan) at 100× magnification. Three fields per well were counted and the vector titer was determined by calculating the total number of blue cells/well divided by the total volume of supernatant used and expressed as transducing units/ml (tu/ml).

Amplicon packaging. Plasmids were packaged as HSV amplicons using the helper virus-free packaging system developed by Fraefel et al., *J. Virol.* 70:7190–7197 (1996). For this purpose, 2—2 cells were transfected using lipofectamine (GIBCO-BRL) with a mixture of plasmid to be packaged and a set of 5 cosmids which spans the entire HSV genome (Cunningham, C. and A. J. Davison, *Virol.* 197:116–124 (1993)) with the packaging sequences (pac) deleted (Fraefel, C., et al., *J. Virol.* 70:7190–7197 (1996)). Amplicon stocks were harvested 60 hours later and purified by brief centrifugation at 1000×g for 10 minutes. Amplicon titers (transducing units per ml; tu/ml) were determined by infecting 293T/17 cells and counting GFP positive cells at 100× magnification 18 hours post-infection.

Retrovirus production after infection with amplicons. Retrovirus production in 293T17 cells. One day prior to infection, $2 \times 10^6$ cells were plated on 60 mm dishes. Cells were infected at different multiplicities of infection (MOI-number of transducing units per cell) in a maximum volume of 3 ml. The following day, the medium was replaced with 3 ml of fresh medium and the cells incubated for 24 hours before harvesting the medium for retrovirus titering. Each MOI was repeated in triplicate. Retrovirus titers were determined as above.

Amplicon neutralization experiment. For this purpose, 293T/17 cells were plated as before. On the day of infection, the appropriate number of transducing units to achieve an MOI of 2 were diluted in growth medium to a final volume of 3 ml. Diluted amplicon vector stocks were incubated for 10 minutes at room temperature with the following antibodies and serum to final dilution of 1:50: rabbit anti-HSV type I polyclonal antibody (#B0114, DAKO, Glostrup, Denmark), normal rabbit serum (Vector, Burlingame, Calif.); rabbit antilacZ antibody (#55975, ICN Pharmaceuticals, Costa Mesa, Calif.), as an unrelated rabbit antibody, and PBS as a control. Besides this incubation period, the experiment was repeated as before. Each experimental condition was repeated in triplicate.

Retrovirus production in glioma cells. One day prior to infection, $5 \times 10^5$ cells were plated on 60 mm plates. The following day, cells were infected at different MOI, as above, prior to harvesting the supernatant for retrovirus titering. Each MOI was repeated in triplicate. Retrovirus titers were determined as above. For retrovirus production kinetics, on the day of harvesting, the total number of cells per plate was determined using a cell counter (Coulter, Miami, Fla.), and $5 \times 10^5$ cells were replated on 60 mm plates. Two days later, medium was replaced with 3 ml of fresh medium and the following day the supernatant was harvested for titering. The same process was repeated at each time point.

Stability of transgene expression. One day prior to infection, J3T and Gli-36 cells were plated in 6 well dishes at a density of $1 \times 10^5$ cells per well. The following day, cells were infected with amplicon vectors at MOI of 2 in a total volume of 1 ml in growth medium and returned to the 37° C. incubator for 24 hours after which the medium was replaced by 1.5 ml fresh medium. Cells were kept in 6 well dishes until day 4 after which they were transferred to 60 mm plates. Cells were then split 1:5 every three days. The experiment was repeated twice in triplicate for each cell line.

Beta-galactosidase activity measurement. Cells were harvested at different timepoints, in cell lysis buffer (Promega, Madison, Wis.) and stored at −80° C. Total amount of protein for all samples was determined using the Coomassie plus protein assay reagent (Pierce, Rockford, Ill.) and a bovine serum albumin (BSA) standard (Bio-Rad, Hercules, Calif.). Beta-galactosidase activity in each sample was measured using a beta-galactosidase assay kit (Promega). Samples and standards were incubated for 30 minutes at 37° C.

Western Blot. Cells were lysed in a buffer containing 50 mM Tris (pH 8.0), 150 mM NaCl, 0.5% NP-40 and a cocktail of protease inhibitors (Boeringer-Mannheim, Indianapolis, Ind.). Protein concentrations were determined as above. An equal amount of total cell protein (60 $\mu$g) was denatured and separated by electrophoresis on 10% polyacrylamide gels with SDS. Rainbow markers (Amersham Life Sciences, Arlington Heights, Ill.) were used as molecular weight markers. Proteins were transferred to nitrocellulose membrane (BioRad Trans-Blot Transfer Medium Pure 0.45 $\mu$m) in transfer buffer (25 mM Tris, 192 mM Glycine, pH 8.3) using a BioRad Transblot Cell for 3 hours at 0.5 mA at 4° C. Membranes were stained with 0.2% Ponceau S (Sigma) to ensure equal loading of samples and proper transfer. After staining, the membranes were blocked overnight in 10% non-fat dry milk powder in TBST (150 mM NaCl, 50 mM Tris, pH7.9, 0.05% Tween 20). The following day, membranes were washed twice for 15 minutes and twice for 5 minutes in TBST and then incubated for 1 hour at room temperature with 1:3000 dilution of the primary antibodies in 2% non-fat dry milk powder in TBST. Anti-p30 and anti-p70 antibodies were developed in goat against Rauscher murine virus p30 (CA protein) and p69/71 (SU protein) proteins, respectively (Quality Biotech Inc). The membranes were washed as before and incubated for 30 minutes with a 1:5000 dilution of anti-goat IgG peroxidase conjugated secondary antibody (Santa Cruz Biotechnology, Santa Cruz, Calif.) in TBST with 5% milk. After washing as before, the blots were developed using ECL reagents (Amersham Life Sciences). Membranes were then exposed to film for 30 seconds up to 30 minutes. Films were scanned and the bands were analyzed for their integrated densities using the NIH Image 1.62 software.

Fluorescent activated cell sorting (FACS) analysis. Cells were trypsinized and centrifuged for 5 minutes at 500×g. After resuspension in PBS, cells were analyzed for the percentage of GFP positive cells using a FacsCalibur analyzer (BectonDickinson, Franklin Lakes, N.J.).

Results

Construction of HERE and HERA amplicons. The vector design takes advantage of the host range and retention properties of an HSV/EBV hybrid amplicon to develop a single vector system which enables cells to produce recombinant retrovirus vectors after transduction. Retrovirus genes, gag-pol and env (GPE), and retroviral vector sequences were cloned into an HSV/EBV hybrid amplicon (FIG. 1). This amplicon has in its backbone the EBV origin of replication (Oris P) and a mutant version of the Epstein-Barr nuclear associated antigen 1 (EBNA-1) coding region (Yates, J. L., et al., Nature 313:812–815 (1985)) under the control of the Rous sarcoma virus (RSV) promoter. In addition it carries the cDNA for an enhanced green fluorescent protein gene (EGFP; Clontech, Palo Alto, Calif.) under the control of the HSV immediate early gene 4/5 promoter (IE4/5), and an HSV origin of replication (ori$_s$) and packaging signal ($\alpha$). GFP expression can be used to follow the fate of the amplicon vector backbone. Ecotropic and amphotropic retrovirus GPE expression cassettes were cloned between the immediate/early cytomegalovirus (CMV) promoter and the bovine growth hormone (BGH) polyadenylation signal, generating the HSV/EBV/Retrovirus hybrid vectors, HERE and HERA, which code for the ecotropic (E) and the amphotropic (A) envelopes, respectively. Retrovirus vector sequences encoding lacZ were cloned downstream from the GPE expression unit in two different orientations to evaluate potential interference between the CMV and 5' LTR (long terminal repeat) promoters (FIG. 1A). Vectors HERE lacZ A1 and HERA lacZ B7 have the 5' LTR promoter placed so that transcription from this promoter occurs in the same direction as the CMV-GPE cassette with vectors HERE lacZ A7 and HERA lacZ B3 in the opposite orientation. Two control vectors were also constructed in which the retrovirus vector sequences were cloned in the hybrid amplicon without the gag-pol-env genes, generating the vectors HER lacZ C1 and HER lacZ C5 with the same and opposite orientations relative to the CMV promoter, respectively (FIG. 1B).

A major concern in developing retrovirus packaging cell lines is the risk of recombination events generating replication competent retroviruses. To minimize potential for recombination events taking place in this new amplicon packaging system, the MoMLV gag-pol-env genes and vector elements were modified to reduce overlap between them. The gag-pol-env genes derived from the plasmid MOV$\Psi^-$ have a 350 bp deletion that removes the retrovirus packaging signal (Mann, R., et al., Cell 33:153–159 (1983)). In addition, the promoter elements were removed from the 5' LTR, leaving the 5' untranslated region intact to avoid altering the splicing mechanism that generates the message encoding the envelope glycoproteins (SU protein-gp70 and TM protein—p15E). The 3' end was modified to remove all non-coding sequences after the stop codon of the env gene. Two different gag-pol-env (GPE) cassettes were constructed, one conferring an ecotropic (MOV12), and another an amphotropic (MOV Ampho) host range. These cassettes were cloned into pcDNA3.1 Neo(−) vector under the control of the CMV promoter, flanked at the 3' end with the BGH polyadenylation signal (BGHpolyA).

The retrovirus vector component of this amplicon vector was derived from the retrovirus vector, BabePuro. To reduce the overlap with the GPE cassettes, the packaging signal was reduced to its minimal sequence, removing the gag gene region, which in some constructs has been shown to increase the efficiency of packaging (Bender, M. A., et al., J. Virol. 61:1639–1646 (1987); Morgenstern, J. P. and H. Land, Nucleic Acids Research 18:3587–3596 (1990)). The 3' end of the vector contains the 3' LTR and the 35 bp sequence that separates the stop codon of the env gene from the 3' LTR and thus it has no sequence overlap with the modified retrovirus genes. With these two sequence alterations, the homology between the vector element and the GPE cassette was reduced to 164 bp at the 5' end.

Testing the re-designed retrovirus elements for production of recombinant retrovirus vectors. To determine the efficiency of the MOV12 and MOV Ampho constructs to produce retroviruses, human 293T/17 cells were co-transfected with these plasmids and a lacz-encoding retroviral vector plasmid, BabePuro lacZ. Transfection efficiencies of 80–90% were obtained, as evaluated by X-gal staining. Two days post-transfection, lacZ-(+) retrovirus vectors in the medium were titered on NIH3T3 cells.

Co-transfections of the pcDNA3.1MOV12 plasmid produced titers of $5.9 \times 10^6 \pm 1.6 \times 10^6$ tu/ml (titer±standard deviation), while the plasmid pcDNA3.1MOV Ampho generated retrovirus titers of $1.8 \times 10^6 \pm 4.5 \times 10^5$ tu/ml. By comparison, co-transfection of the original MOV-$\Psi^-$ plasmid (ecotropic) with BabePuro lacZ plasmid yielded titers of $1.3 \times 10^6 \pm 2.9 \times 10^5$ tu/ml in 293T/17 cells. Phoenix-E cells, derived from 293 cells, are an established packaging cell line for transient production of retrovirus vectors with ecotropic host range. Transfection of these cells with BabePuro lacZ plasmid resulted in retrovirus titers of $1.2 \times 10^6 \pm 3.3 \times 10^5$ tu/ml. These results indicate that the GPE expression cassettes generated in this study are fully functional and at least as efficient as the original MOV-$\Psi^-$ plasmid or an established packaging cell line in generating retrovirus vectors.

The effect of deleting the gag gene region from the extended packaging signal on vector titers was also assessed. Co-transfection of the gag-deleted vector, TVBPlacZ, with pcDNA3.1MOV12 into 293T/17 cells resulted in the production of $7.1 \times 10^6 \pm 6.0 \times 10^5$ tu/ml, while a similar vector, TVBPgaglacZ, where the gag region was retained resulted in similar retrovirus titers of $8.2 \times 10^6 \pm 3.9 \times 10^5$ tu/ml. Previous studies have reported that inclusion of the gag region in retroviral constructs resulted in a 10 fold increase in retroviral titers (Bender, M. A., et al., *J. Virol.* 61:1639–1646 (1987); Morgenstern, J. P. and H. Land, *Nucleic. Acids Res.* 18:3587–3596 (1990)). One possible explanation for the difference with our findings is that our vectors were tested by transient co-transfections of 293T/17 cells, while others were tested in stable retrovirus producer cell clones. In similar transient cotransfection experiments in 293 cells, Naviaux et al. have estimated that each transfected cell receives about 100 plasmid copies (Naivaux, R. K., et al., *J. Virol.* 70:5701–5705 (1996)). It is possible that in our experiments, the lower efficiency of packaging of the gag(-) vector is compensated by a very large pool of packageable vector RNAs due to the large number of expression units present. Alternatively, it could be a construct specific effect since other reports have also shown that deletion of this gag region from some retrovirus vectors has little or no effect on viral titers (Kim, S. H., et al., *J. Virol.* 72:994–1004 (1998)).

Testing the HERE and HERA amplicons and amplicon vectors for retrovirus vector production. The HERE and HERAlacZ amplicons were transfected into 293T/17 cells. Two days post-transfection, the supernatants were harvested and titered for retrovirus vector production on NIH 3T3 cells (FIG. 2). HERElacZ and HERAlacZ amplicons generated retrovirus stocks with average titers of $1 \times 10^7$ and $7 \times 10^6$ tu/ml, respectively, about 2-fold higher than having the GPE cassette and the retrovirus vector in two different plasmids with the same promoters and polyadenylation signals (above). No significant difference in titers resulted from the two orientations of the retrovirus vector cassette. The presence of both retrovirus elements in one construct means that all transfected cells receive equimolar amounts of both elements and their rates of loss are the same. No retrovirus vectors were generated when constructs HERlacZ C1 or C5 were tranfected into 293T/17 cells, demonstrating that these cells can not provide retroviral functions necessary for packaging.

The HERE, HERA, and HERlacZ amplicons were packaged in HSV virion particles in 2.2 cells using the helper virus-free packaging system developed by Fraefel, C., et al., *J. Virol.* 70:7190–7197 (1996)). Typical amplicon vector titers assessed on 293T/17 cells varied between $2 \times 10^6$ and $1 \times 10^7$ tu/ml HERE and HERAlacZ amplicon vectors were used to infect naive 293T/17 cells at a multiplicity of infection (MOI) of 2. The transduction efficiency was about 50%, measured as the percentage of GFP-positive cells at 48 hours post-infection by FACS analysis. At this time, the supernatants were harvested and titered on NIH3T3 cells (FIG. 3A). The HERElacZ amplicon vectors yielded retrovirus titers of $4.2 \times 10^5 \pm 6.2 \times 10^4$ tu/ml for HERElacZ A1 and $3.7 \times 10^5 \pm 4.7 \times 10^4$ tu/ml for HERElacZ A7, about 2-fold higher than those obtained for the HERAlacZ amplicon vectors (HERA lacZ B3: $1.7 \times 10^5 \pm 4.3 \times 10^4$ tu/ml;. HERElacZ B7: $1.8 \times 10^5 \pm 2.5 \times 10^4$ tu/ml), with no significant difference between the two orientations in either set.

A neutralization experiment was performed to determine whether production of retrovirus vectors was exclusively dependent on transduction of 293T/17 by the amplicon vector. For this purpose, HERAlacZ B7 amplicon vector stocks were treated with a rabbit antibody directed against HSV-1 envelope glycoproteins, normal rabbit serum or an unrelated rabbit antibody. Treatment of the amplicon stocks with the anti-HSV-1 antibody reduced the transduction efficiency of the amplicon vector from 50% to 0.2% and resulting retrovirus vector titers decreased by more than 10,000 fold to less than 10 tu/ml. Treatment of amplicon vector stocks with normal rabbit serum or an unrelated rabbit antibody did not have any effect on transduction efficiency or retrovirus titers (FIG. 3A). Thus, retrovirus vectors produced after infection of 293T/17 cells with amplicon vectors are not the result of transfer of retrovirus packaging functions from 2—2 cells, but through amplicon transduction.

HERElacZ Al and HERAlacZ B7 amplicon vectors were used to analyze the relation between MOI and resulting retrovirus titers 48 hours post-infection of 293T/17 cells (FIG. 3B). There was a linear relationship between MOI and retrovirus titers, up to MOI of 5 (HERElacZ A1 amplicon: $y=1.2 \times 10^5 + 1.4 \times 10^5$ x, $R^2 = 0.99$; HERAlacZ B7 amplicon: $y=1.4 \times 10^4 + 8.0 \times 10^4$ x, $R^2 = 0.99$). Maximal retrovirus titers of $1.0 \times 10^6 \pm 2 \times 10^5$ tu/ml and $4.9 \times 10^5 \pm 10 \times 10^5$ tu/ml were achieved at MOI of 10 for HERE and HERAlacZ amplicon vectors, respectively. For both types of amplicon vectors, the transduction efficiency was 18% at MOI of 0.5 and reached a maximum of 81% at MOI of 10 (FIG. 3B).

Retrovirus production in Gliomas. A number of glioma lines derived from humans (T98, U87.ΔEFGR, SNB-19, Gli-36), rat (9L, CNS-1) and dog (J3T) tumors were tested for their ability to produce retroviruses upon infection with the HERAlac Z B7 amplicon vector at MOI of 2. Two days after infection, the medium was harvested to determine retrovirus titers, and the transduction efficiency for each glioma line was also evaluated (Table 1).

TABLE 1

Transduction efficiency and production of retrovirus vectors by glioma lines two days after infection with HERA lacZ B7 amplicon vector

| Cell line | Species | % GFP cells[a] | Retrovirus titer (tu/ml)[b] |
|---|---|---|---|
| Gli-36 | Human | 80–90 | $1.0$–$1.2 \times 10^5$ |
| SNB-19 | Human | 15–21 | 400–1000 |
| T98 | Human | 8–13 | <10 |
| U87.ΔEGFR | Human | 5–8 | 200–300 |
| 9L | rat | ND | <10 |
| CNS-1 | rat | 7–9 | <30 |
| J3T | dog | 20–25 | $6$–$8 \times 10^4$ |

[a]Cells were infected with HERA lacZ B7 amplicon vector at MOI of 2. Two days post-infection, the percentage of GFP positive cells was determined by FACS analysis. Abbreviation: ND, Not determined.
[b]Media were harvested to determine retrovirus titers 2 days post-infection. Titers are an average of two experiments repeated in triplicate.

For three human glioma lines, Gli-36, SNB-19 and U87.ΔEGFR, retrovirus titers $1.0$–$1.2 \times 10^5$, 400–1000 and 200–300 tu/ml, respectively, were roughly proportional to transduction efficiencies of 80–90% for Gli-36, 15–21% for SNB-19 and 5–8% for U87.ΔEGFR cells. T98 was an exception to this trend, with less than 10 tu/ml detectable in the supernatant, while the percentage of transduced cells was 13%. The rodent glioma models, 9L and CNS-1, showed low infectability with the amplicon vector and very low production of retrovirus vectors. The dog glioma line J3T generated retroviral titers of $6$–$8 \times 10^4$ tu/ml with 20–25% transduced cells.

Gli-36 and J3T glioma cells, which yielded the highest retroviral titers, were chosen to analyze the kinetics of retrovirus production. One day after plating, cells were infected at different MOIs with HERA lacZ B7 amplicon vector and two days later the supernatants were harvested for titering retrovirus vectors. Cells were then passaged at the same density as on day 0 and this procedure was repeated on day 5 and 8 post-infection. Production of retrovirus vectors overtime was different between these two cell lines. J3T cells showed an increase in retroviral titer between day 2 and day 5 followed by a decay between day 5 and day 8 (FIG. 4A). Although at two days post-infection there was no difference in titers between different MOIs, at later timepoints there was a direct correlation between MOI and retrovirus titers. Maximum retroviral titers of $1.6 \times 10^5$ tu/ml were obtained for MOI of 5 at day 5 post-infection. Titers decreased to $8.0 \times 10^4$ tu/ml by day 8 for the same MOI. In contrast, Gli-36 cells showed maximal retroviral production of $1.0$–$1.2 \times 10^5$ tu/ml at 48 hours post-infection and a decrease thereafter to titers of $2.0$–$3.0 \times 10^4$ tu/ml at 8 days. No significant differences were observed with increasing MOIs for Gli36 (FIG. 4B).

The retention of amplicon sequences over time in infected J3T and Gli-36 cells was determined for MOI of 2 and 5 by evaluating the percentage of GFP-positive cells by FACS analysis. For J3T cells infected at MOI of 2 and 5, the percentage of GFP-positive cells decreased overtime from 22% and 44%, respectively, at day 2 to 8.1% and 19.9% at day 5, and 2.4% and 8.9% at day 8 (FIG. 4C). For Gli-36 cells infected at MOI of 2 and 5, the percentage of amplicon transduced cells decreased from 80.2% and 92%, respectively, at 2 days to 69.4% and 83.4% at day 5 and 31.8% and 44.3% at day 8 (FIG. 4C).

The ratio of retrovirus particles produced/producer cell can be used as a measure to estimate the efficiency of a packaging cell line. To calculate this ratio, the assumption was made that all GFP-positive cells produced retrovirus vectors. Taking into account the total number of GFP-positive cells and retrovirus titers for each timepoint, for Gli-36 cells infected at MOI of 2 or 5, this packaging ratio was between 0.13 and 0.15 retroviral particles/producer cell at 48 hours, decreasing at later timepoints to about 0.04 to 0.05. For J3T cells infected at MOI of 2, this ratio was 0.5 at day 2, 0.94 at day 5, and 1.2 at day 8 post-infection, while for MOI of 5, the ratio remained the same at 0.5 from day 2 to day 8.

J3T and Gli-36 cells also grew at different rates during the course of the experiment. Gli-36 cells increased in average 6 fold for each 3 day time interval and MOI analyzed, corresponding to a generation time of 29 hours, similar to uninfected cells under the same culture conditions. For the last two time intervals, J3T cells showed an average generation time of 24 hours for all three MOIs tested, similar to uninfected cells. However, for the first time interval, from the day of plating until day 2 post-infection, the generation times appeared to be longer and dependent on MOI. For MOIs of 1 and 2, the doubling time was 36 hours, while for MOI of 5 it was 48 hours, possibly indicating some initial vector toxicity. The rate of loss of GFP expressing J3T cells infected at MOI of 2 and 5 between day 2 and day 8 post-infection was 13.5% and 12.1% per generation, respectively, while for Gli-36 cells infected at the same MOIs, the rates of loss were 12% and 10.4% per generation, respectively.

Although the amplicon infection efficiency of Gli-36 cells was about 4-fold Is higher than for J3T, maximal retrovirus titers produced were similar and the ratio of the number of retroviral vectors/producer cell decreased with time for Gli-36 cells. To determine whether relative production of retrovirus virion proteins was responsible, expression of Gag-Pol and gp70 (surface protein, SU) retrovirus proteins was analyzed in infected cells over time. Total proteins were extracted at day 2 and day 8 post-infection from cells infected at MOI of 2 with HERAlacZ B7 and HERlacZ Cl amplicon vectors, and naive cells, and analyzed by western blot using antibodies capable of recognizing the Mo-MLV capsid protein p30(CA) (FIG. 5A) and gp70 (FIG. 5B). For J3T (FIG. 5A, lanes 2 and 5) and Gli-36 (FIG. 5A, lanes 8 and 11), cells infected with the HERAlacZ B7 amplicon vector, it was possible to detect the $Pr65^{gag}$ precursor protein, as well as the mature p30(CA) capsid protein with the anti-p30 antibody. Other immunereactive polypeptides were also detected which could be partially cleaved forms of the $Pr65^{gag}$ precursor. The bands corresponding to the precursor $Pr65^{gag}$ and p30(CA) were analyzed for their densities to compare the levels of these proteins for each cell line at different timepoints. For J3T cells, there was a 12 fold decrease in the amount of $Pr65^{gag}$ precursor protein between day 2 and day 8 post-infection. Levels of p30(CA) remained the same over this time period. For Gli-36 cells there was a decrease of 1.8 fold for the $Pr65^{gag}$ precursor while p30(CA) remained at the same level. Comparison between the two cell lines showed that $Pr65^{gag}$ was 2.2 fold more abundant in Gli-36 cells than in J3T cells at 48 hours post-infection, while this difference increased to 16 fold at 8 days. Expression of gp70 (SU) (FIG. 5B) remained the same for J3T cells over time (FIG. 5B, lanes 2 and 5), while for Gli-36 cells it decreased by 1.6 fold (FIG. 5B, lanes 8 and 11). Expression in Gli-36 cells was 16 fold higher than in J3T cells at 48 hours post-infection. These results indicate that there is no positive correlation between retrovirus titers and expression levels of virion proteins.

Stability of transgene expression. Stability of amplicon-mediated gene expression in cells transduced by these HERA hybrid amplicon vectors was analyzed above by the percentage of GFP-positive cells, retrovirus vector titers, and expression of retrovirus proteins over time. The question remaining was whether the presence of the retroviral elements, the gag-pol-env cassette and retrovirus vector, have any effect on retention of the transgene (lacZ) carried by the retrovirus vector, i.e., whether retrovirus vectors produced by amplicon transduced cells were able to infect and confer stable transgene expression on other cells in the population. To address this issue, J3T and Gli-36 cells were infected with the HERAlacZ B7 amplicon at MOI of 2 and lacZ activity was measured in the total population at different times post-infection up to 1 month (FIG. 6A). Since these amplicons have all the functions necessary for packaging retroviruses, it is likely that the amplicon vector stocks themselves contain some retrovirus vectors carrying the lacZ gene, which are produced during packaging of the amplicons in HSV virions and could stably infect cells contributing for total lacZ activity in the population. To compensate for this factor, lacZ activities in cultures were expressed as a percentage of the activity at 48 hours post-infection. The relative lacZ activity for J3T cells, where 22% of cells were initially transduced, increased with time reaching a maximum increase of 5 fold at three weeks and maintaining a constant level out to 4 weeks. Gli-36 cells, with 80% transduction with amplicon vector at 48 hours, reached a maximum of 2 fold at 7 days and then remained stable (FIG. 6A). In addition to this difference in relative transgene expression over time, lacZ activity in J3T cells was three to four-fold higher than in Gli-36 cells at 48 hours post-infection. To assess the contribution of the amplicon vector itself to total lacZ expression over time, cells were infected at MOI of 2 with the HER lacZ C1 amplicon, which does not code for any retrovirus proteins. For both cell types, lacZ activity reached a maximum at 4 days post-infection and then decreased with time being undetectable by day 15 to 21 (FIG. 6B).

Since there was a greater increase in lacZ activity over time in J3T cells versus Gli36 cells for a 4-fold lower initial transduction efficiency, experiments were designed to evaluate whether the increase in lacZ activity in a population of Gli-36 cells was dependent on the initial percentage of amplicon infected cells. Gli-36 cells were infected with HERAlacZ B7 amplicon vector at MOI of 0.1, 0.5, 1 and 2 achieving a range of transduction efficiencies (% of GFP-positive cells) at 2 days post-infection of 16.6, 49.3, 65.9, and 80.2%, respectively. An inverse correlation between increase in lacZ activity and MOI was observed over 2 weeks (FIG. 6C). For the population infected at an MOI of 0.1, lacZ activity increased by 7 fold, while for MOI of 2, lacZ activity increased only by about 2 fold. Absolute lacZ activity levels were 15 fold higher for MOI of 2 than for MOI of 0.1 at 48 hours post-infection, while at 2 weeks, this difference decreased to 3.5 fold. Thus, the increase in lacZ activity approximately reflected the initial percentage of infected cells, being 7-fold for Gli-36 at 16.6% transduced and 5-fold for J3T at 22%.

Discussion

The development and characterization of a hybrid amplicon vector system capable of single step conversion of cells to retrovirus vector producer cells is described in this Example. Transduction of several cell types with this vector system resulted in the efficient production of retrovirus vectors. For the same cell line, retrovirus titers were dependent on the extent of amplicon transduction, but different cell lines displayed different capacities for retrovirus production. Infection of a population of dividing cells with this system results in continuing increase in transgene activity until a stable, steady state level is reached.

Several vector systems have been developed which can induce cells to transiently produce replication-deficient retrovirus vectors after transduction. Some systems use transfection to introduce components of the vector system into cells (Li, K. J. and H. Garoff, *Proc. Natl. Acad. Sci. USA* 93:11658–11663 (1996); Naviaux, R. K., et al., *J. Virol.* 70:5701–5705 (1996); Noguiez-Hellin, P., et al., *Proc. Natl. Acad. Sci. USA* 93:4175–4180 (1996)). This process is efficient in culture, but inefficient in vivo.

Others have used combinations of viral vectors to achieve the same result. In a two step approach, cells are first infected with a retrovirus vector and then with an HSV amplicon vector coding for the gag-pol and env genes (Savard, N., et al., *J. Virol.* 71:4111–4117 (1997)), or with an adenovirus vector carrying these genes in the same (Lin, X., *Gene Ther.* 5:1251–1258 (1998)); or separate vectors (Id.); Yoshida, Y., *Biochem. Biophys. Res. Comm.* 232:379–382 (1997)). Retrovirus genes and vector element can both be delivered by adenoviral vectors (Duisit, G., et al., *Human Gene Ther.* 10:189–200 (1999); Feng, M., et al., *Nature Biotech.* 15:866–870 (1997)). Some of these adenovirus based systems can generate relatively high retrovirus titers ($10^5$–$10^6$ cfu/ml) in cultured cells (Duisit, G., et al., *Human Gene Ther.* 10:189–200 (1999); Yoshida, Y., *Biochem. Biophys. Res. Comm.* 232:379–382 (1997)). Although systems that employ different vectors to deliver the elements necessary for retrovirus production have a low potential to generate replication competent retroviruses (RCR), output titers depend on the efficiency of co-transduction. The more different vectors that are needed, the lower the probability that all will infect the same cell to allow retrovirus vector production. Adenovirus vectors can be produced at very high titers (>$10^{10}$ pfu/ml) and can achieve remarkable gene transfer efficiencies in some circumstances in vivo. However, in some applications, such as gene transfer to malignant human gliomas, their transduction efficiency has been reported to be only 30–35% in certain areas, with an overall efficiency below 11% (Puumalainen, A. M., et al., *Human Gene Ther.* 9:1769–1774 (1998)). At this level of transduction, the probability that 2 or 3 vectors will infect the same cell is low, and therefore the ability to convert cells in situ into retrovirus packaging cells would be compromised. However, Feng et al. demonstrated that in a tumor model in vivo, a retrovirus production system based on two adenoviral vectors was capable of increasing transgene retention as compared to a conventional adenovirus vector (Feng, M., et al., *Nature Biotech.* 15:866–870 (1997)). The present invention demonstrates that the principle can work, but conceptually the process should be more efficient if a single adenovirus vector contained all necessary elements to generate retrovirus vectors. Although the size limitation of conventional adenovirus vectors precludes the construction of such vector, "gutless" adenovirus vectors could easily accommodate all the components.

The hybrid amplicon vector system described in this Example has several advantages over existing vector systems for generating retroviral vectors: (1) all elements necessary for production of replication-deficient retrovirus vectors are present or can be placed in the same construct. In theory, the conversion efficiency per transduced cell is 100%, independently of whether amplicon DNA is introduced into cells by transfection or infection; (2) not only do HSV virions have a wide host range, stability and high infectability, but due to their large DNA capacity and the mode of viral DNA replication, each amplicon vector carries multiple copies of the amplicon plasmid. This means that for each transduction event, multiple copies of the transgenes are delivered to the cell nucleus. This may account for the high retroviral titers obtained with this system; (3) presence of the EBV elements, oriP and the EBNA-1 gene, which mediate episomal replication and retention of amplicon DNA in dividing cells, increases the duration of retrovirus production; and (4) HSV amplicons have a large transgene capacity (theoretically up to 150 kb) which will allow the inclusion of other elements to improve the efficiency of retrovirus vector production.

The efficiency of gene delivery mediated by this hybrid amplicon vector system is dependent on a number of factors, including infectability with HSV and retrovirus virions, capacity to produce retrovirus vectors and retention of amplicon elements. Infectability of target cells by HSV virions is a primary determinant of the levels of retrovirus vectors produced by a cell population, while the transduction efficiency by retrovirus vectors is ultimately responsible for long term transgene retention. In this study, infection of a variety of cell lines with the same number of hybrid amplicon virions resulted in a large spectrum of transduction efficiencies (Table 1). This could result from different levels of promoter activity in different cell lines or an intrinsic property of each cell line. Entry of both types of virus is dependent on the expression levels of certain cell surface receptors (Kurre, P., et al., *J. Virol.* 73:495–500 (1999); Montgomery, R. I., et al., *Cell* 87:427–436 (1996)). Since manipulation of these levels in vivo is not an alternative, optimization can only be accomplished by modifying the virions to increase the variety of cell surface receptors which can be used to enter cells.

For HSV virions, this could be achieved by using helper functions from different strains of HSV and/or modifying the virion envelope to enhance binding of the vector to receptors abundant on the target cells (Laquerre, S., et al., *J. Virol.* 72:9683–9697 (1998)). For retrovirus vectors, a broader host range can be achieved by pseudotyping the virions with vesicular stomatitis virus envelope glycoprotein (VSV-G) (Burns, J. C., et al., *Proc. Natl. Acad. Sci. USA* 90:8033–8037 (1993)). However, expression of this protein can be toxic and thus limit the length of time that transduced cells can produce vectors. An alternative would be to use other envelope genes that have different host ranges and no toxicity associated with their expression, such as the gibbon ape leukemia virus (GALV) envelope glycoprotein or envelope genes which are modified to target specific cell types (Kasahara, N., et al., *Science* 266:1373–1376 (1994)).

Another factor that affects the gene delivery efficiency of this system is the ability of the amplicon-infected cells to produce retrovirus. In the present Example, infection of different cell lines with the HERAlacZ amplicon resulted in a wide range of retrovirus titers that did not always correlate with cell infectability, since different cell lines with comparable transduction efficiencies produced very different retrovirus vector titers (Table 1). Some studies have suggested that cells have an intrinsic maximal capacity to generate retrovirus, which is dependent on cellular factors that are not yet understood (Cosset, F. L., et al., *J. Virol.* 69:7430–7436 (1995); Duisit, G., et al., *Human Gene Ther.* 10:189–200 (1999)). Production of retrovirus vectors showed different patterns for the two glioma lines analyzed with respect to the number of retrovirus vector particles produced/amplicon-transduced cell. For J3T cells, this ratio was about 10-fold higher than for Gli-36 cells, suggesting that the former produce retrovirus vectors much more efficiently than the latter.

Several hypothesis can be advanced to explain the difference in retrovirus vector production among cell lines: limiting amounts of packageable RNA, low expression of retroviral protein(s) or premature processing of retrovirus precursor proteins. The amount of packageable retrovirus vector RNA can be estimated from the level of lacZ activity per GFP-positive cell early in the course of infection (48 hours), when most lacZ activity is attributable to amplicon infected cells and not to subsequently retrovirus infected cells. At this early time point, lacZ activity/GFP-positive cell is 15 fold higher in J3T than in Gli-36 cells indicating that the level of vector RNA generated from the 5' LTR promoter is lower in Gli-36 than in J3T cells. Possible explanations are that the MoMLV LTR promoter is intrinsically weaker in Gli-36 cells, due to low or absent levels of some transcription factors necessary for efficient promoter activation or that the activity of the LTR promoter in Gli-36 cells is inhibited to a greater extent than in J3T cells by the upstream CMV promoter via a deficient transcription termination mechanism mediated by the BGHpolyA sequence.

Although the expression levels of retrovirus proteins could also be a limiting factor in some cells, this does not appear to be a factor in Gli-36 and J3T cells as Pr65$^{gag}$ and gp70 levels are higher in Gli-36 than J3T cells by about the same magnitude as the percentage of transduced cells, which is the inverse of their retrovirus vector production efficiencies. In fact, it has been shown that overexpression of the HIV-1 Gag-Pol polyprotein can lead to intracellular activation of the viral protease, mainly resulting in the production of capsid and matrix proteins, with inhibition of assembly and budding of virus-like particles (Karacostas, V., et al., *Virol.* 193:661–671 (1993)). The presence of processed MoMLV virion proteins, e.g., p30(CA) has also been reported following infection with adenoviral vectors (Duisit, G., et al., *Human Gene Ther.* 10:189–200 (1999); Lin, X., *Gene Ther.* 5:1251–1258 (1998)) or Semliki Forest virus-derived expression vectors (Li, K. J. and H. Garoff, *Proc. Natl. Acad. Sci. USA* 93:11658–11663 (1996)). The presence of mature virion proteins, such as p30(CA), suggests that the viral protease is being prematurely activated and may result, by comparison with HIV, in inhibition of virion formation. Thus, the cellular ratio of Pr65$^{gag}$ and p30(CA) may be a useful indicator for the efficiency of virion assembly and retrovirus production. Based on the density of the bands on the western blot in this study, the ratio of Pr65$^{gag}$/p30(CA) for Gli-36 cells decreased from 0.9 to 0.5 between day 2 and day 8 while for J3T cells, it decreased from 35 to 1.6 for the same period of time. Although these values could serve as a basis to explain the difference between Gli36 and J3T cells, the fact that for J3T cells the retrovirus production efficiency ratio (vectors/GFP$^+$cell) increases between day 2 and day 8 suggests that there might be no correlation between the two ratios, Pr65$^{gag}$/p30(CA) and vectors produced/GFP$^+$ cell, at least for the same cell line.

However, since it has not been determined which premature virion proteins are responsible for the inhibitory effect on HIV virion assembly, the presence of this same effect for MoMLV assembly can not be ruled out. It is possible that different levels of premature processing may play an important role in determining maximum retrovirus output in different cell types. It will then be necessary to understand the cellular factors that regulate this processing before any improvements can be made to increase retroviral production from certain cell types. Alternatively, if the main cause of different retrovirus production capacities among different cells is related to promoter activity, several changes in vector design can be made to increase its efficiency in a broader spectrum of cells: (1) substitution of the Mo-MLV 5' LTR by chimeric LTR promoters which can yield higher retrovirus vector titers (Kim, S. H., et al., *J. Virol.* 72:994–1004 (1998); Naviaux, R. K., et al., *J. Virol.* 70:5701–5705 (1996)); (2) increase in the distance between the GPE expression cassette and the retrovirus vector sequences to reduce the chance of transcriptional interference between the two promoters; (3) introduction of additional transcription termination sequences to reduce promoter interference; and (4) construction of a large library of HERA amplicon vectors with different promoter combinations to identify the most efficient configuration for a particular cell type.

In this Example, it was evident that transgenes carried in the amplicon backbone decreased in expression with time after infection in these populations of dividing cells. This was true for both GFP and retrovirus proteins as well as retrovirus vector production. Since expression of those transgenes was mediated by different promoters, the most likely explanation for this decline is loss of amplicon DNA as has been observed by others for HSV/EBV amplicon vectors (Wang, S. and J. M. Vos, *J. Virol.* 70:8422–8430 (1996)). In the absence of drug selection for amplicon retention, both Gli-36 and J3T cells lost 10–12% of GFP-positive cells per generation. Other studies have shown that without drug selection, plasmids carrying the EBV oriP element and EBNA-1 gene are lost from human cells at rates between 1 and 5%/generation (Yates, J. L., et al., *Nature* 313:812–815 (1985)). The apparently faster rate of loss in the present study could be due to a number of factors: (1) rate was measured as loss of transgene expression and could include promoter inactivation as well as loss of amplicon DNA; (2) the mutant EBNA-1 gene used, which has most of the GlyAla repeats deleted (to reduce toxicity), has been shown to be less effective than full length versions in episome replication and maintenance (Wendelburg, B. J., et al., *Gene Ther.* 5:1389–1399 (1998)); (3) the presence in the amplicon vector of multiple origins of DNA replication (both oriP and oriS) might interfere with the efficiency of DNA replication; (4) the concatemeric nature of the amplicon episome and its size (150 kb) may be conducive to a high frequency of deletional recombination events disrupting transgene expression; and/or (5) expression of some of the genes present in this triple hybrid amplicon (tribrid) could increase the generation time of transduced cells and thus select against them.

Figure 6:
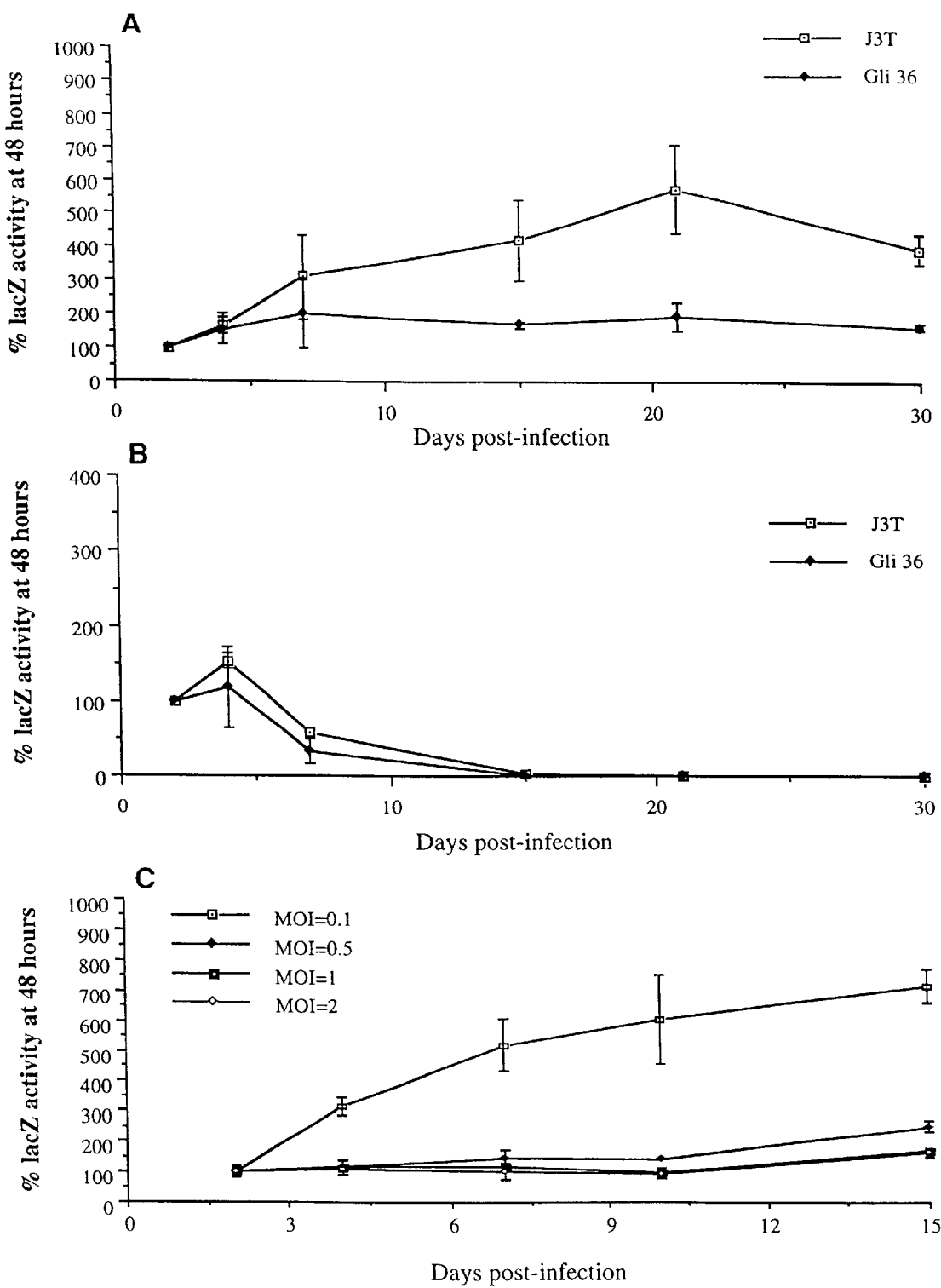

This tribrid vector system provides a means to stably deliver a transgene to a large percentage of cells in a dividing population starting with transduction of a small percentage of cells. For both J3T and Gli-36 populations, when 20% of cells were initially transduced, activity levels of a retrovirally encoded transgene (lacZ) rose 5 to 6-fold over time, despite the decline in amplicon-mediated transgene expression (FIG. 6). Shortly after infection of a dividing cell population with the amplicon vector, two different cell genotypes are present while a third one arises later.

The first genotype, amplicon-transduced cells, express GFP and LacZ encoded by the episomal amplicon, and produce retrovirus vectors carrying the lacZ gene, while at the same time they are themselves resistant to infection by those same retrovirus vectors due to the presence of the envelope proteins on the cell surface (Coffin, J. M., in B. N. Fields et al., (ed.) *Fields Virology*, Raven Publishers, Philadelphia (1996)). Since the size of the HERAlacZ amplicon is 25 kb, and amplicon plasmids are packaged in HSV virions as tandem repeats up to a size of approximately 150 kb, each episome carries 6 copies of each transgene.

The second genotype, represents uninfected cells which do not express any transgenes, but are susceptible to infection by retrovirus vectors produced by amplicon-transduced cells. With time, a third cell type appears in the population which expresses lacZ from retrovirus vector sequences stably integrated in their genome, and is receptive to multiple retroviral infections. Due to the episomal nature of the amplicon and the absence of any selection pressure for retention, the first population decreases in representation over time, and therefore overall retrovirus vector production also declines. Cells which lose the amplicon also lose expression of lacZ and retroviral proteins but become susceptible to retroviral infection, depending on the half-life of gp70 on the cell surface.

The third cell type becomes more prominent with time, until it is the sole contributor to lacZ activity in the population, and essentially no more retrovirus vectors are produced. Total lacZ activity in the population at any time is the sum of lacZ expressed from the episomes (6 copies/episome x number of episomes per cell) and from the retrovirus vectors stably integrated in the cell genome (1 copy/infection x number of infections). Absolute levels of lacZ activity will depend on the relative activity of the LTR promoter in the context of the episome or at different sites of integration in different cell types. Gli-36 and J3T populations infected at an MOI of 2 with the HERAlacZ amplicon vector displayed two different profiles of lacZ activity over time, with large (6x) and small (2x) increases, respectively. The main reason for this difference appears to be the percentage of cells initially transduced as when this was normalized to about 20% (MOI=2 for J3T and MOI=0.1 for Gli-36) both populations increased lacZ activity by about 6 fold over 2 weeks post amplicon infection (FIG. 6). The behavior of cell populations in accumulating transgene activity could be described by the following model (FIG. 7). At low initial levels of amplicon transduction, the number of transduced cells and levels of lacZ activity are low in the early post infection period. At the same time, there is a large pool of cells which are susceptible to retrovirus infection and hence able to achieve stable lacZ activity. In contrast, at high initial levels of transduction, lacZ activity is high in the early period post-infection but the percentage of retrovirus injectable cells is small and increases only as retrovirus titers are declining, thus achieving only a modest increase in lacZ activity. Interestingly, for both Gli-36 and J3T cells, expression levels of gp70 declined slower (FIG. 5) than retrovirus titers (FIG. 4) suggesting that cells which have lost their ability to produce retrovirus might still not be susceptible to retrovirus infection due to the continuing presence of envelope protein on the cell surface. This model would explain why lowering the percentage of amplicon transduced cells (lower MOIs) results in a higher increase in lacZ activity in the population over time (FIG. 6C).

The HERA triple hybrid gene delivery system of the present invention could be used in vivo to directly modify specific cell populations, which by their position, migratory or tissue/organ targeting properties, could secondarily deliver retrovirus vectors to progenitor/stem cells or to a larger population of dividing cells, resulting in expanded spatial distribution of transgene expression. Several applications for this gene delivery amplification mechanism include tumor therapy and genetic modification of the developing central nervous system, hematopoietic system, lung epithelium, and other proliferating cell populations. Although the more extensive use of this gene delivery amplification mechanism in the adult is limited by the fact that the retrovirus components in this tribrid system are derived from MoMLV, which can only infect dividing cells, this could be surpassed by replacing those components with lentivirus elements, thus allowing for production of retroviral vectors that can infect both dividing and non-dividing cells.

The vector system of the invention may also be used for two modalities of therapeutic gene delivery to tumors. In one mode, the retrovirus producer cells would be derived from the tumor cells themselves and thus presumably share the same growth and migratory patterns; in the other mode, normal cells with migratory or tumor targeting properties could be used as gene delivery vehicles, e.g., neuronal progenitor cells (Aboody-Guterman, K. S., "Neural stem cells migrate throughout and express foreign genes within experimental gliomas—a potential gene therapy approach to brain tumors" (submitted for publication, 1999), endothelial cells (Lal, B., et al., *Proc. Natl. Acad. Sci. USA* 91:9695–9699 (1994)), and tumor infiltrating lymphocytes (Kasid, A., et al., *Proc. Natl. Acad Sci. USA* 87:473–477 (1990)). Several studies have shown that packaging cell lines currently in use, which are derived from mouse fibroblasts, do not display migratory properties in the context of brain tumors (Ram, Z., et al., *Nature Med.* 3:1354–1361 (1997); Tamiya, T., et al., *Gene Ther.* 2:531–538 (1995); Tamura, M., et al., *Human Gene Ther.* 8:381–391 (1997)). This presents several restrictions to effective gene delivery. The packaging cells tend to form clusters around the injection site, and given the limited diffusion of retroviruses through cell layers, only those packaging cells close to the cluster surface release retrovirus vectors which can infect tumor cells. As a result, the number of vector particles that reach tumor cells is much lower than what would be expected from the number of packaging cells implanted. Furthermore, these retrovirus vectors have a relatively short half-life and can only infect dividing cells. In experimental brain tumor models, which have high mitotic indexes, these small 'clusters' of gene delivery can be effective in therapeutic strategies. However, in human glioblastomas (GBM), where it is estimated that only 1–8% of the cells are actively dividing (Yoshii, Y., et al., *J. Neurosurg.* 65:659–663 (1986)), the probability of a packaging cell being close to a dividing cell is extremely low. Furthermore, one of the major challenges for therapy of human GBM is the invasive nature of these cells, which migrate extensively along a limited number of routes in the CNS (Pederson, P. -H., et al., *Cancer Res.* 53:5158–5165 (1993); Yamada, M., et al., *J. Neurosci. Res.* 38:415–423 (1994)). Tamura et al. have shown that if the same type of glioma cells are implanted in the tumor mass, they tend to migrate along the same routes as the initial tumor cells and eventually reach them (Tamura, M., et al., *Human Gene Ther.* 8:381–391 (1997)). Using tumor cells themselves as retrovirus producers could possibly bypass the current restrictions to gene delivery by retrovirus vectors by spreading vector production over larger areas.

Although some tissues, like the CNS, are relatively immune privileged sites, an immune response to expressed retroviral proteins or transgene products would limit the survival of amplicon-derived packaging cells. Possible ways to reduce the immune response would be to incorporate in the amplicon certain immune-modulatory molecules, such as those that tumors use to evade the immune system, e.g., CD95 ligand, transforming growth factor-β, interleukin-10 (Hahne, M., et al., *Science* 274:1363–1366 (1996)). The main advantage of this triple hybrid amplicon gene delivery system is that it should mediate retrovirus vector production in situ after direct injection of amplicon vector stocks into the tumor mass, without the need for any tissue culture manipulation or implantation of exogenous cells.

This transgene delivery amplification mechanism could also be used to expand the range of gene delivery in the developing CNS. Several studies performed with replication competent retrovirus vectors during development have shown that transgenes can be delivered to a large number of cells throughout the entire CNS (Fekete, D. M. and C. L. Cepko, *Mol. Cell Biol.* 13:2604–2613 (1993)). However, RCRs carry with them not only the transgene of interest but also a high risk of insertional oncogenesis. The HERA system of the present invention could be used in a similar, but safer, manner to achieve widespread gene delivery in the CNS. Genetic modification of cells in the subventricular zone would create two amplifying effects: first, production of retrovirus vector in that area could result in genetic modification of neuronal progenitors that would later migrate out into the brain and differentiate into neurons. Second, amplicon-transduced cells could themselves migrate to other regions of the brain where they can come in close contact with populations of dividing glia during gliogenesis. Such spatial expansion mechanisms would be useful for gene delivery in disease states where the entire CNS is involved and can be corrected by diffusible factors, as is the case for some lysosomal storage disorders.

This same principle can be used for genetic modification of the hematopoietic system. This could be achieved by transducing CD34-positive cells in culture followed by re-implantation and migration of these cells to the bone marrow where they would come in close contact with dividing hematopoietic stem cells. Alternatively, similar to what was attempted with fibroblast-derived packaging cells (Nelson, D. M., et al., *Human Gene Ther.* 8:747–754 (1997)), the amplicon vector could be directly injected into the bone marrow. These strategies could be used for gene delivery to normal bone marrow, and also in the context of leukemia. Since bone marrow stem cells divide very slowly, it is possible that retrovirus vectors produced in situ would preferentially infect leukemic cells. As a safety mechanism, cells could be transduced with prodrug activating enzymes that result in the production of metabolites whose cytotoxic effects are cell cycle dependent, such as the HSV-tk/ganciclovir system.

The principle of the primary producer cells being in close proximity to secondary target cells might also prove useful to attain stable gene delivery to the lung. Adenovirus vectors and liposomes are capable of transducing the lung epithelium with varying degrees of efficiency. Due to the non-integrative nature of these delivery modalities and the turnover of cells in the lung epithelium, these strategies only achieve transient expression of transgenes. Repeated administration of some of these agents results in strong inflammatory immune responses. An alternative approach using integrating vectors, such as lentivirus vectors (Goldman, M. J., et al., *Human Gene Ther.* 8:2261–2268 (1997)), would also require repeated administration of the viral vector due to turnover of transduced cells. Since 95% of the epithelial surface is occupied by type I pneumocytes (terminally differentiated) and only 3% by type 11 pneumocytes (stem cells), direct vector will most likely transduce type I cells. Furthermore, in some disease states, such as cystic fibrosis, the rate of replacement seems to be accelerated (Leigh, M. W., et al., *Am. J. Resp. Cell Mol. Biol.* 12:605–612 (1995)). Since type I cells are derived from type II cells, the latter dividing cells are the appropriate targets to achieve stable genetic modification of the lung epithelium. In theory, infection of the lung epithelium with HERA amplicons should convert type I cells into retrovirus producer cells, which can deliver vectors to type II cells in the vicinity when they divide and they, in turn, would give rise to genetically modified type I cells.

This novel triple hybrid amplicon delivery system provides a means to extend retrovirus gene delivery to larger numbers of cells over a wider distribution in the body, as compared to current retrovirus producer cells. It also potentially allows the direct conversion of endogenous cells to packaging cells and thus should have wide application in methods of gene therapy.

EXAMPLE 2

Construction and Characterization of HSV/AAV Hybrid Amplicons

Materials and Methods

Cells: NIH 3T3 cells, 2—2 cells, Gli-36 human primary glioma cells, and J3T dog glioma cells were obtained as described in Example 1. Naive Mus dunni cells (MD), Mus dunni cells expressing lacZ (MDZ) (Dranoff, G., et al., *Proc Natl Acad Sci USA* 90:3539–3543 (1993)), and ΨCRIPlacZ (Danos, O., and Mulligan, R. C., *Proc. Natl. Acad. Sci. USA* 85:6460–6464 (1988)) were kindly provided by Dr. Richard Mulligan (Harvard Medical School, Boston, Mass.). NIH 3T3 and ΨCRIPlacZ cells were grown in Dulbecco's modified Eagle's medium (DMEM) supplemented with 10% calf serum (Sigma, St. Louis, Mo.). 293T/17, Gli-36, J3T, and 2—2 cells were grown in DMEM with 10% fetal bovine serum (Sigma). MD and MDZ cells were grown in DMEM/F12 and 5% fetal bovine serum. All medium was supplemented with 100 U/ml penicillin and 0.1 mg/ml streptomycin (Sigma). 2—2 cells growth medium was further supplemented with 0.5 mg/ml G418 (GIBCO BRL, Gaithersburg, Md.). Cells were grown at 37° C. and 5% $CO_2$ in a humidified atmosphere. Transduced J3T and Gli-36 cells were selected in growth medium supplemented with 1 mg/ml G418 and/or 1 g/ml puromycin (Sigma).

Plasmids:. Construction of HyRMOV Ampho. The retrovirus gag-poland env genes (GPE) were obtained from pcDNA3.1MOV Ampho, which is described in Example 1. Briefly, the GPE cassette was modified to remove all noncoding regions after the stop codon of the envelope gene and promoter regions from the 5' LTR. The gag-pol genes were derived from the plasmid pMOVΨ−, which has a 350 bp deletion that removes the retroviral packaging signal (Mann, R., et al., *Cell* 33:153–159 (1983)), while the env gene was derived from the 4070A amphotropic genome (Chattopadhyay, S. K., et al., *J. Virol.* 39:777–791 (1981)). The GPE cassette was removed by digestion with Nhe I and Pme I and the resulting 7390 bp fragment was cloned into the same restriction sites in HyRGFP (Costantini, L. C., et al., "Gene Transfer to the Nigrostriatal system by Hybrid HSV/AAV Amplicon Vectors", submitted *Human Gene Therapy* (1999)), resulting in the removal of the GFP gene, originating the plasmid, HyRMOV Ampho.

Construction of retrovirus vector hybrids. The retrovirus vector element was derived from the plasmid TVBPlacZ, which is described in Example 1. This plasmid was constructed from the retrovirus vector Babepuro (Morgenstern, J. P., and Land., H., *Nucleic Acids Res.* 18:3587–3596 (1990)), obtained from Dr. Jay Morgenstern, by removing the gag gene region present in this vector, shortening the retrovirus packaging signal to its minimal sequence. Thus, the sequence homology between the retrovirus vector and the GPE cassette was reduced to 164 bp at the 5' end. The retrovirus element carrying the lacZ gene was removed from TVBPlacZ by digestion with Not I and cloned into the Bgl II site in pITR (Fraefel, C., et al., *Mol Med.* 3:813–825 (1997) by blunt-end ligation, originating the plasmid, pITRBPlacZ. This plasmid was in turn digested with Not I and the resulting fragment, carrying the retrovirus element flanked by the AAV ITRs, was cloned into the Not I site of the plasmid HSRepN I (Id.) generating the plasmid, HyB-PlacZ. This fragment derived from pITRBPlacZ was also cloned into the Not I site of the plasmid HSvec2 (similar structure to HSRepN 1, but missing the Rep expression cassette) (Id.) originating the plasmids, HSHyBPlacZ #2.2 and HSHyBPlacZ #2.1. The Not I fragment derived from TVBPlacZ was also cloned into HSvec2, generating the plasmids, HSTVBPlacZ #3.2 and HSTVBPlacZ #1.2; and into HSRepN1, originating the plasmids, HSRepTVBPlacZ #1.1 and HSRepTVBPlacZ #3.5. The plasmid pcDNA3.1 luc was constructed by removing the firefly luciferase gene from the pGem®-luc vector (Promega, Madison, Wis.) with Bam HI and Xho I and cloning into the same sites of pcDNA3.1 Neo (Invitrogen, Carlsbad, Calif.).

Transfections and vector titer determination. Retrovirus packaging. 293T/17 were transfected by DNA/calcium phosphate co-precipitation essentially as described in Example 1, using $2 \times 10^6$ cells per 60 mm dish and 15 μg of each plasmid. Supernatants were isolated for retrovirus titering 48 hours post-transfection.

Retrovirus titer determination. For all retrovirus titers determined in this example, the media from retrovirus vector producing cells was centrifuged at 500×g for 5 minutes before use. Titers were determined by infecting NIH3T3 cells overnight with different dilutions of retrovirus stocks in the presence of 4 μg/ml polybrene (Sigma). Two days later, cells were fixed in 4% paraformaldehyde in phosphate buffered saline (PBS) and stained with X-gal (5-bromo-4-chloro-indolyl-β-D-galactopyranoside, Fisher, Pa.) solution (1 mg/ml X-gal, 2 mM $MgCl_2$, 5 mM $K_4Fe(CN)_6$, 5 mM $K_3Fe(CN)_6$ in PBS, pH 7.4) overnight. Positive cells (blue cells) were counted using an Argus-20 image processor (Hamamatsu Photonics, Hamamatsu City, Japan) at 100× magnification. Three fields per well were counted and the vector titer was determined by calculating the total number of blue cells/well divided by the total volume of supernatant used and expressed as transducing units/ml (tu/ml).

Helper virus assay. Retroviral stocks were assayed for replication competent retrovirus by a lacZ mobilization assay via Mus dunni cells as previously described in Example 1. To determine the sensitivity of the assay, titered wild type 4070A virus amphotropic virus stocks, obtained from Dr. Richard Mulligan, were used and the assay was shown to be able to detect one particle of 4070A virus per ml of infectious medium. All retrovirus stocks produced in the present Example were negative for RCR by this assay.

Amplicon packaging. Plasmids were packaged as HSV amplicons using the helper virus-free packaging system developed by Fraefel et al., discussed above. For this purpose, 2—2 cells were transfected using lipofectamine (GIBCO BRL) with a mixture of plasmid to be packaged and a set of 5 linearized cosmids. Amplicon stocks were harvested 60 hours later by scraping the, cells into the medium, followed by two freeze/thaw cycles, and purification by centrifugation at 1000×g for 10 minutes. Amplicon titers were determined in triplicate by infecting $3 \times 10^5$ 293T/17 cells/well in 24 well plates with different dilutions. For amplicons carrying lacZ, cells were fixed and stained with X-gal at 18 to 24 hours post-infection. The total number of positive cells (blue cells) per well was determined by counting 3 random fields/well at 100× magnification. Titers were calculated using that number and amplicon stock dilution, and were expressed as transducing units per ml (tu/ml). For HyRMOV Ampho amplicon, cells were fixed with 4% paraformaldehyde at 37° C. for 30 minutes at 18 to 24 hours post-infection.

Transduced cells were detected by immunocytochemistry using a goat antibody developed against Rauscher murine virus p30 (Quality Biotech Inc.), which cross-reacts with the MoMLV p30(CA) protein. After thorough washing with PBS, cells were treated with 0.1 % NP-40 in PBS for 20 minutes followed by blocking solution (1.2% $H_2O_2$ and 10% rabbit serum (Vector Laboratories, Burlingame, Calif.) in PBS) for 45 minutes. Cells were incubated with primary antibody (1:750 dilution in PBS+1%BSA) for 1 hour. A rabbit biotinylated anti-goat IgG (Vector Laboratories) was used as a secondary antibody (1 hour with 1:200 dilution in PBS+1% BSA) followed by incubation for 30 minutes with a mix of A and B reagents from a Vectastain ABS kit (Vector Laboratories) prepared according to manufacturer's instructions. Detection was performed for 2 to 5 minutes in DAB solution prepared by dissolving SIGMAFAST™ DAB tablets (Cat. #: D-4168, Sigma) in $H_2O$ (0.7 mg/ml 3,3'-diaminobenzidine [DAB], 10 mg/ml Urea hydrogen peroxide, and 60 mM Tris buffer). All incubations were performed at room temperature and between each step, cells were washed 4 times with PBS. Total number of positive cells (brown cells) per well was determined and amplicon titers were calculated as above.

Effect of the Rep expression cassette on activity of downstream LTR promoter. Transfections. Human 293T/17 cells ($3 \times 10^5$ cells/per well in 24 well dishes) were transfected overnight with 0.2 µg of each plasmid and lipofectamine PLUS (4 µl PLUS reagent, 1 µl lipofectamine, in 25 µl Opti-MEM I-GIBCO BRL) in 0.2 ml growth medium.

Beta-galactosidase and luciferase activity measurements. Two days post-transfection, cells were washed twice with PBS and lysed in 300 µl of 1× Reporter lysis buffer (Promega) for 15 minutes at room temperature. The lysate was centrifuged at 17,000×g for 2 minutes at 4° C. and the supernatant was used to measure beta-galactosidase and luciferase activities. LacZ activity in each sample (10 µl of lysate) was measured using a beta-glactosidase assay kit (Promega). Samples and standards were incubated for 30 minutes at 37° C. To measure luciferase activity, 100 µl of lysate was mixed with 370 µl of luciferase buffer (25 mM glycylglycine, 15 mM $MgSO_4$, 4 mM EGTA-pH 7.8) containing 2 mM ATP, 1 mM dithiothreitol, and 15 mM potassium phosphate (pH 7.8), and assayed using a 1251 luminometer in integral mode (Wallac, Gaithersburg, Md.) in the presence of 0.2 mM D-Luciferin (Sigma) in luciferase buffer. The activity of the LTR promoter in each vector for each experimental condition was expressed as a ratio between lacZ activity and luciferase activity (internal control for transfection efficiency), and compared to the average of ratios obtained for TVBPlacZ transfected cells (Relative LTR activity). This experiment was repeated twice in triplicate.

Infections. Retrovirus vectors. Retrovirus vector stocks were produced by co-transfection of 293T/17 cells with retrovirus vector plasmids and pcDNA3.1MOV Ampho. J3T and Gli-36 cells were infected overnight in the presence of 4 µg/ml polybrene and 2 days later placed in selective growth medium containing 1 µg/ml puromycin.

Amplicon vectors. Cells ($5 \times 10^5$ cells/60 mm plate) were infected with amplicon stocks at different MOIs in a total volume of 3 ml. The following day, medium was replaced with fresh growth medium and incubated for 24 hours before harvesting the supernatant for retrovirus titering. Transduced Gli-36 and J3T cells were then selected in growth medium containing 1 mg/ml G418 and 1 µg/ml puromycin.

Production of retrovirus by stable packaging cells. Cells were plated at the same density as for amplicon infection and 24 hour supernatants were harvested 3 days later for retrovirus titering. At the same time that medium was harvested for retrovirus titering, the total number of cells in the plates were counted using a cell counter (Coulter, Miami, Fla.).

Western blot. Cells were lysed in a buffer containing 50 mM Tris (pH 8.0), 150 mM NaCl, 1% NP-40 and Complete™-Mini cocktail of protease inhibitors (Boeringer-Mannheim, Indianapolis, Ind.). Protein concentrations were determined using a Coomassie plus protein assay reagent (Pierce, Rockford, Ill.) and a bovine serum albumin (BSA) standard (Bio-Rad, Hercules, Calif.). An equal amount of total cells protein (60 µg) was denatured and separated by electrophoresis on 10% polyacrylamide gels with SDS. Rainbow markers (Amersham Life Sciences, Arlington Heights, Ill.) were used as molecular weight markers. Proteins were transferred to nitrocellulose membrane (BioRad Trans-Blot Transfer Medium Pure 0.45 µm) in transfer buffer (25 mM Tris, 192 mM Glycine, pH 8.3) using a BioRad Transblot Cells for 3 hours at 0.5 mA at 4° C. Membranes were stained with 0.2% Ponceau S (Sigma) to ensure equal loading of samples and proper transfer. After staining, the membranes were blocked overnight in 10% non-fat dry milk powder in TBST (150 mM NaCl, 50 mM Tris, pH7.9, 0.05% Tween 20).

The following day, membranes were washed twice for 15 minutes and twice for 5 minutes in TBST and then incubated for 1 hour at room temperature with 1:3000 dilution of the primary antibodies in 2% non-fat dry milk powder in TBST. Anti-p30 and anti-p70 antibodies were developed in goat against Rauscher murine virus p30 (Ca protein) and p69/71 (SU protein) proteins, respectively (Quality Biotech Inc.). The membranes were washed as before and incubated for 30 minutes with a 1:5000 dilution of anti-goat IgG peroxidase conjugated secondary antibody (Santa Cruz Biotechnology, Santa Cruz, Calif.) in TBST with 5% milk. After washing as before, the blots were developed using ECL reagents (Amersham Life Sciences). Membranes were then exposed to film for 30 seconds up to 30 minutes. Films were scanned and the bands were analyzed for their integrated densities using the NIH Image 1.62 software.

Northern Blot. Total cellular RNA was isolated with Trizol® reagent (GIBCO BRL) according to manufacturer's instructions. Twenty µg of total RNA were denatured at 65° C. for 10 minutes in MOPS buffer (20 mM Na.MOPS, 8 mM NaAc, 1 mM EDTA, pH 7.0) 6% formaldehyde and 50% formamide (v/v) (Fisher) and separated by electrophoresis at 4 V/cm for 3 hours in a 1.1 % agarose gel with 6% formaldehyde (Fisher) in MOPS buffer. RNA was transferred by capillarity to nitrocellulose (Protran™, Schleicher & Schuell, Keene N.H.) overnight with 20×SSC (3M NaCl, 0.3 M sodium citrate, pH 7.0). The blot was UV cross-linked with a Stratalinker (Strategene, La Jolla, Calif.) in automatic mode. The membrane was prehybridized for 4 hours at 42° C. in hybridization solution (0.75 M NaCl, 50 mM $NaH_2PO_4$, 5 mM EDTA, pH 7.4, 10× Denhardt's solution, 100 µg/ml freshly denatured sheared salmon sperm DNA, 50% formamide (v/v) and 2% SDS). The probe (30 ng–1.2 kb fragment of lacZ gene from Sac I site to stop codon) was labeled with $^{32}P$ using a DECAprime™ kit (Ambion, Austin, Tex.) with a final specific activity of $1.8 \times 10^9$ cpm/µg and purified with MicroSpin™ S-300 HR columns (Pharmacia, Piscataway, N.J.). The blot was hybridized with the probe overnight at 42° C. in fresh hybridization solution. The next day, the membrane was washed twice at room temperature for 30 minutes in 2×SSC and 0.1% SDS, followed by two washes at 42° C. for 30 minutes in 0.1×SSC and 0.1% SDS. The membrane was exposed to film at −80° C. in a cassette with intensifying screens (Fisher).

Results

Figure 8:
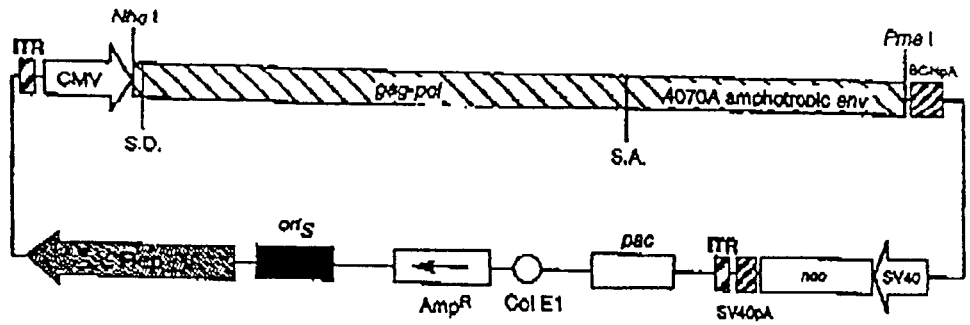
Figure 8:
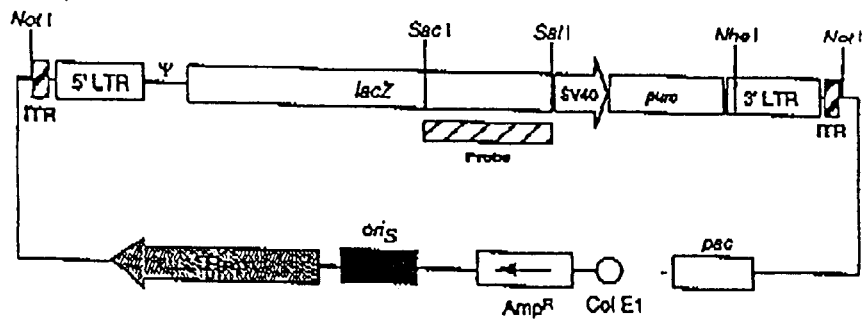

Construction of HSV/AA/Retrovirus (HAR) hybrid amplicons and effect of Rep expression cassette on downstream promoters. Modified retrovirus gag-pol and env genes and vector elements were cloned in a HSV/AAV hybrid amplicon, generating the amplicon plasmids, HyRMOV Ampho and HyBPlacZ, respectively (FIG. 8). Co-transfection of these plasmids into 293 T/17 cells originated retrovirus titers of $4.1 \times 10^5 \pm 1.6 \times 10^5$ tu/ml (±standard deviation). Transfections where one of these plasmids, carrying the Rep expression cassette, was present resulted in a 10-fold decrease in retrovirus titers when compared to co-transfection with the plasmids from where the retroviral elements were derived, pcDNA3.1MOV Ampho and TVBPlacZ (Table 2).

TABLE 2

Generation of recombinant retrovirus vectors by transfection of 293T/17 cells with hybrid amplicon plasmids

| Plasmids[a] | Titer ± SD (tu/ml)[b] |
|---|---|
| HyBPlacZ + HyRMOV Ampho | $4.1 \times 10^5 \pm 1.6 \times 10^5$* |
| TVBPlacZ + pcDNA3.1MOV Ampho | $4.7 \times 10^6 \pm 4.6 \times 10^5$* |
| HyBPlacZ + pcDNA3.1MOV Ampho | $3.0 \times 10^5 \pm 2.2 \times 10^5$* |
| TVBPlacZ + HyRMOV Ampho | $5.8 \times 10^5 \pm 3.3 \times 10^5$* |
| HSHyBPlacZ #2.2 + pcDNA3.1MOV Ampho | $6.2 \times 10^6 \pm 1.1 \times 10^6$* |
| HSHyBPlacZ #2.2 + HyRMOV Ampho | $4.8 \times 10^5 \pm 2.7 \times 10^5$* |

[a]Cells were co-transfected with 15 μg of each plasmid by DNA/calcium phosphate co-precipitation.
[b]Two days post-transfection, the medium was harvested and titered for LacZ(+) retroviruses by infecting NIH3T3 cells. Presence of the Rep expression cassette resulted in a significant decrease in retrovirus titers for both HyRMOV Ampho and HyBPlacZ hybrid amplicons.
*$P < 0.001$ (Student's t-test).
Abbreviations: SD—standard deviation.

Figure 9:
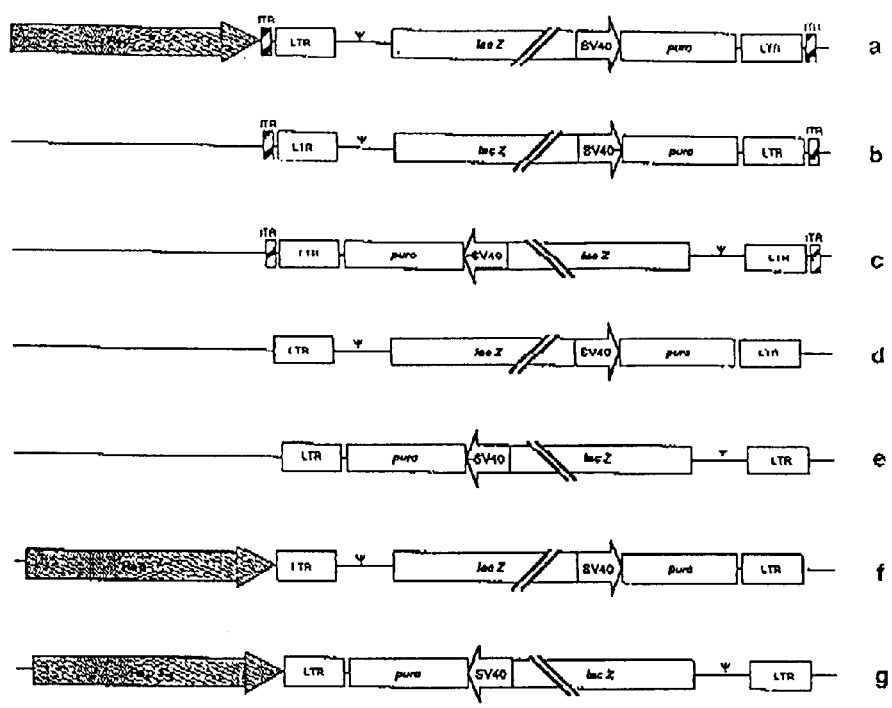
Figure 9:
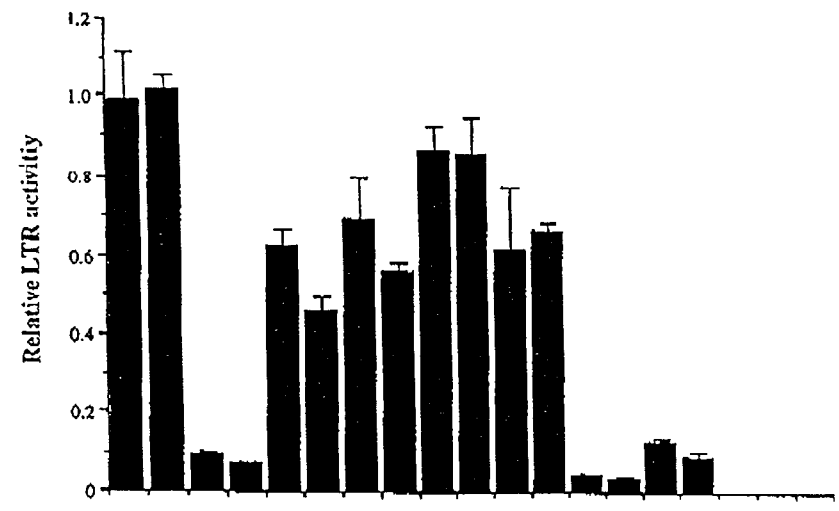

Since the four Rep proteins derived from the rep gene, have been shown to repress the activity of their own promoters and other heterologous promoters (Horer, M., et al., *J. Virol.* 69:5485–5496 (1995)), the effect of the Rep expression cassette on gene expression directed by these amplicons was examined (FIG. 9). A series of amplicons based on HyBPlacZ (FIGS. 8 and 9A-a) were constructed where: Rep expression cassette was removed, leaving the AAV inverted terminal repeat (ITR) elements (FIG. 9A—b,c—HSHyBPlacZ #2.2, HSHyBPlacZ #2.1); Rep expression cassette and ITRs were removed (FIG. 9A—d, e—HSTVBPlacZ #3.2, HSTVBPlacZ #1.2); ITR elements were removed leaving the Rep expression cassette (FIG. 9A—f, g—HSRepTVBPlacZ #1.1, HsRepTVBPlacZ #3.5). These plasmids were co-transfected into 293T/17 cells with pHSvec2 and pcDNA3.1luc (FIG. 9B—3, 5, 7, 9, 11, 13, 15) or pHSRep and pcDNA3.1luc (FIG. 9B—4, 6, 8, 10, 12, 14, 16). TVBPlacZ was also co-transfected with the same combinations of plasmids (FIG. 9B 1, 2). Activity of the LTR promoter in each vector was expressed as the ratio between lacZ and luciferase activities to normalize for transfection efficiency. These ratios were all compared to the average activity of the LTR promoter in TVBPlacZ—relative LTR activity (FIG. 9B). For amplicons where the Rep expression cassette is present, HyBPlacZ (a), HSRepTVBPlacZ #1.1 (f), and HSRepTVBPlacZ #3.5 (g), relative LTR activities were below 15% (FIG. 9B—2, 3, 13, 14, 15, and 16). Presence of Rep in trans resulted in small decreases in promoter activity for these amplicons (FIG. 9B—4, 14, 16). Amplicons where the ITR elements were present, HSHyBPlacZ #2.2 (b), HSHyBPlacZ #2.1 (c), showed relative promoter activities of 65 and 70%, respectively, and presence of Rep in trans had no effect on promoter activity (FIG. 9B—9, 10, 11, 12). The HSHyBPlacZ #2.2 hybrid amplicon plasmid was chosen for further experiments since it has the AAV ITR elements and the activity of the LTR promoter is not severely compromised. To assess its efficiency, the plasmid was co-transfected into 293T/17 cells with pcDNA3.1MOV and HyRMOV Ampho, resulting in retrovirus titers of $6.2 \times 10^6 \pm 1.1 \times 10^6$ tu/ml and $4.8 \times 10^5 \pm 2.7 \times 10^5$ tu/ml, respectively, comparable to titers obtained with TVBPlacZ (Table 2).

Figure 3:
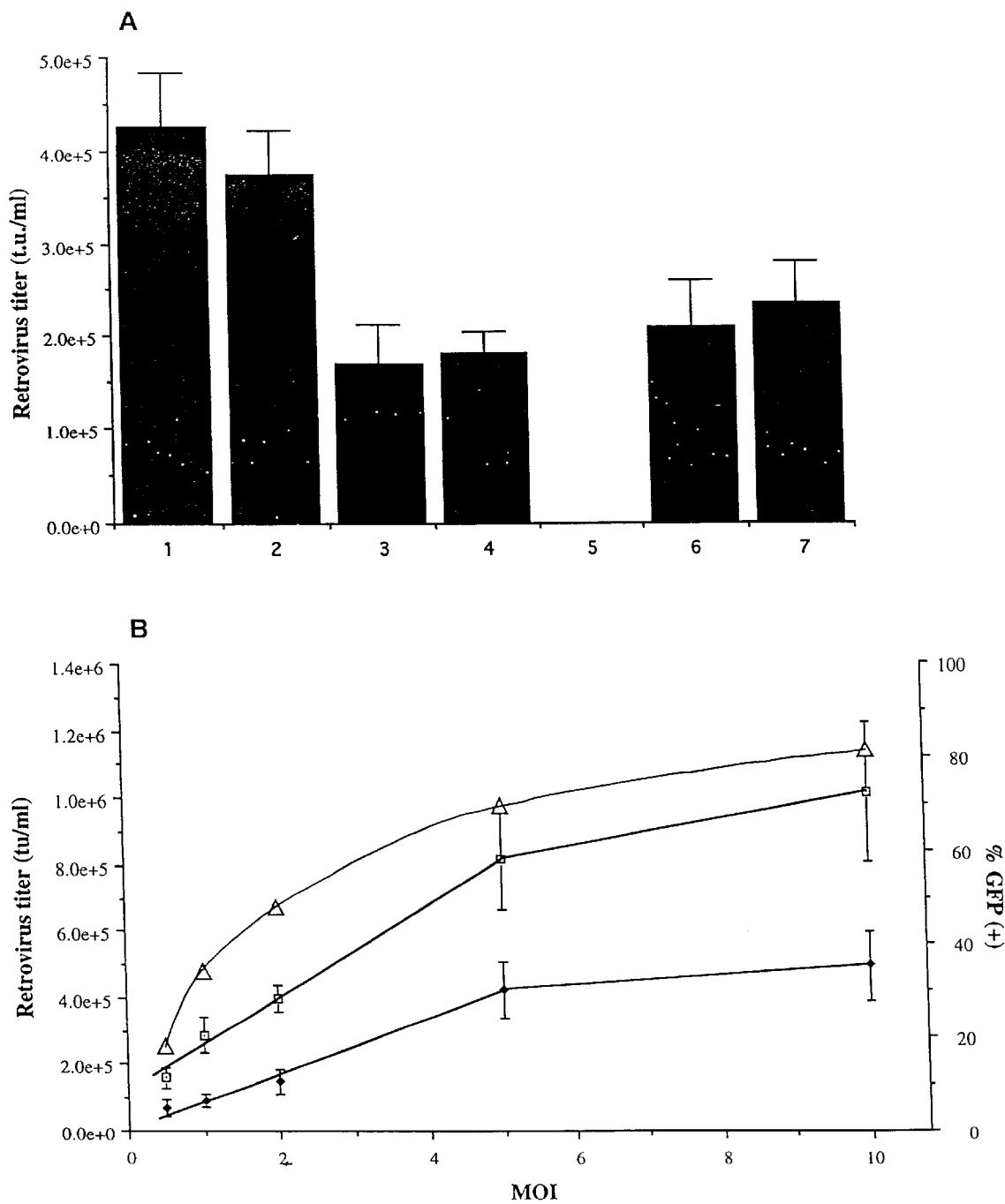
Figure 4:
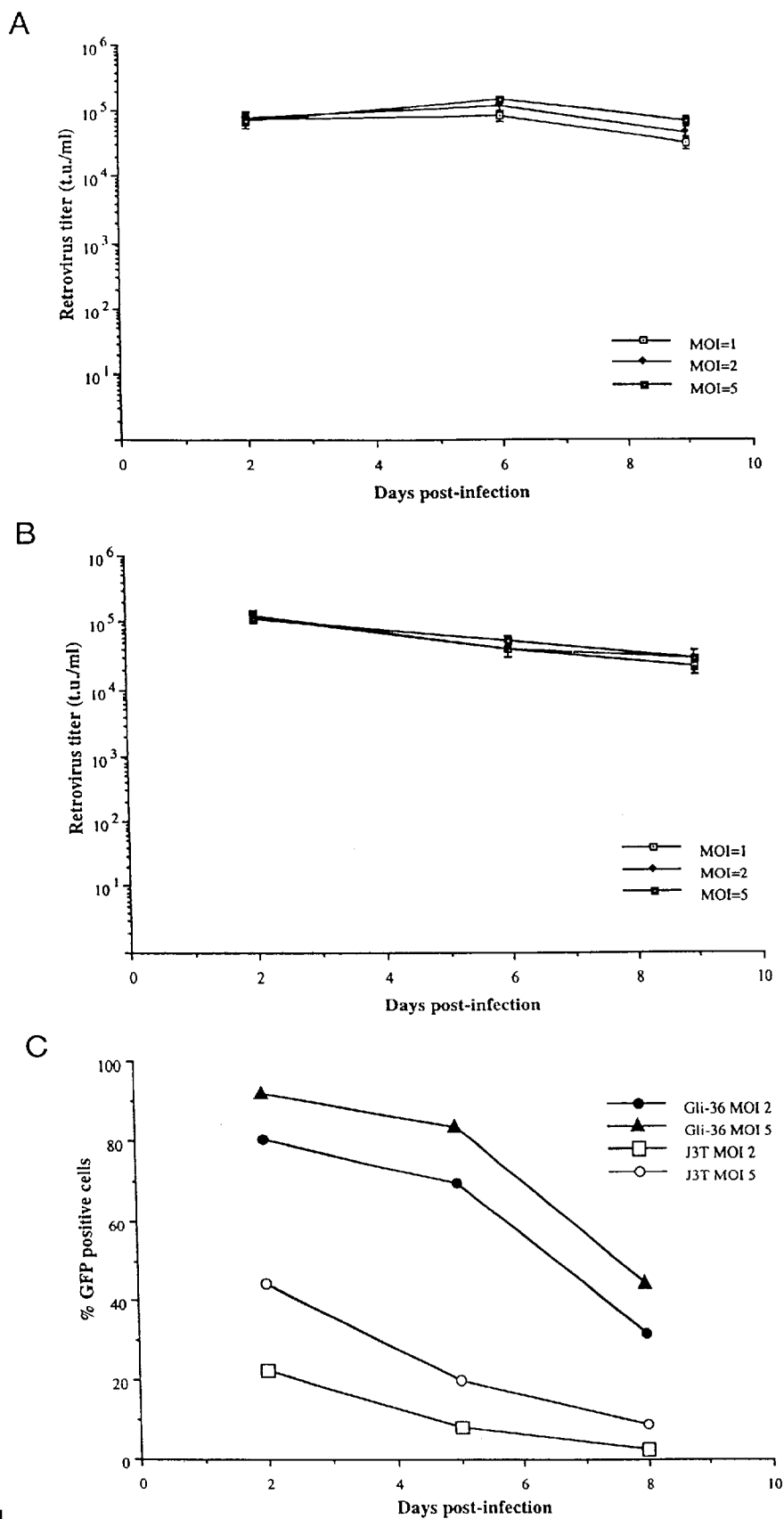
Figure 5:
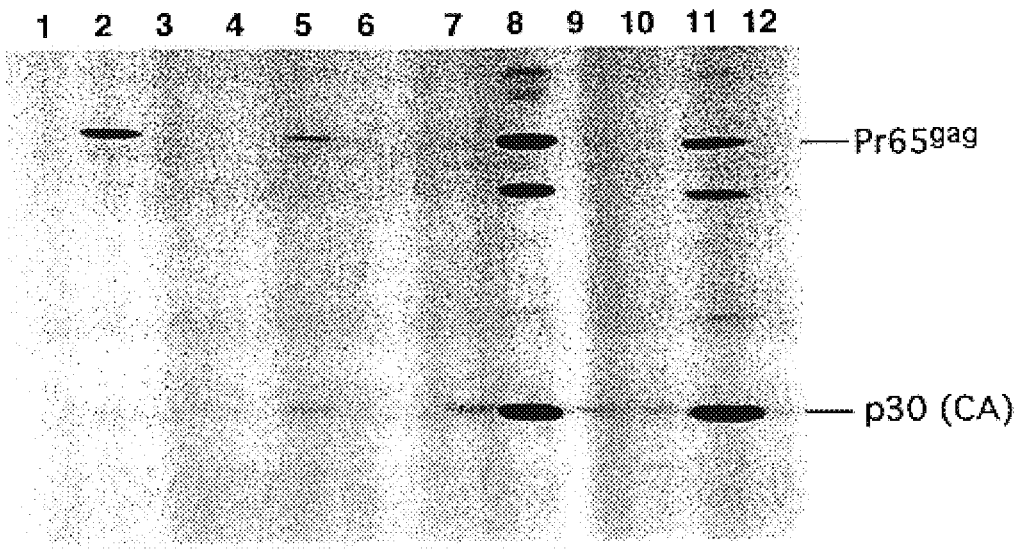
Figure 5:
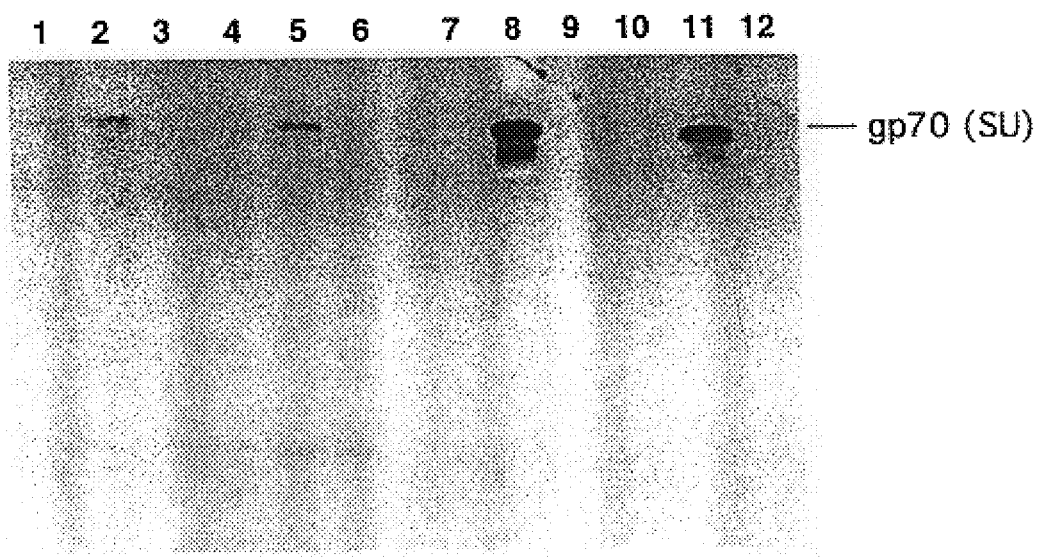
Figure 12:
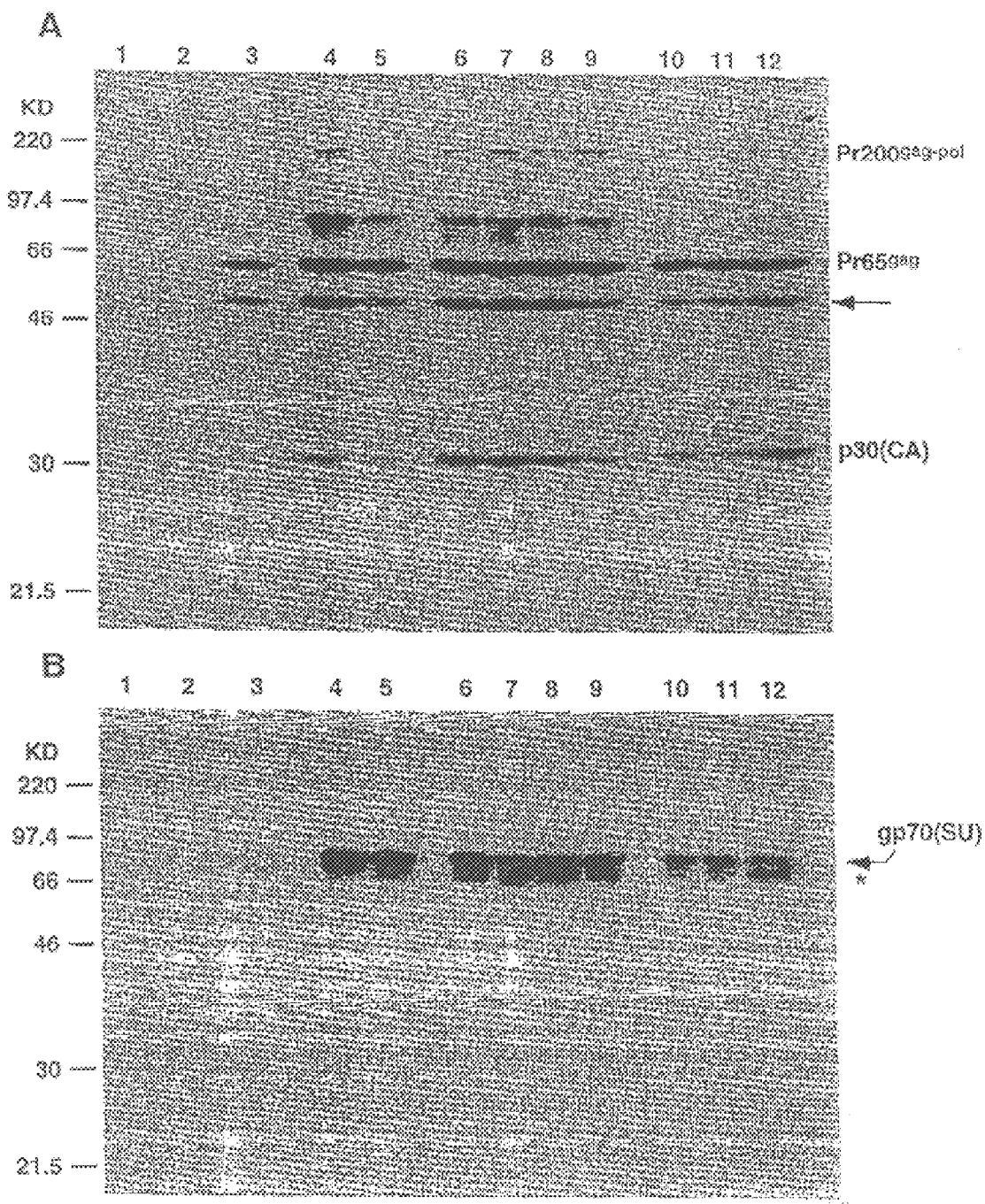

Generation of stable retrovirus packaging cell lines by simultaneous infection with amplicon vectors. HyRMOV Ampho and HSHyBPlacZ #2.2 amplicons were packaged in HSV virions using a helper virus-free packaging system (Fraefel, C., et al., *J. Virol.* 70:7190–7197 (1996)). Amplicon vector stocks were consistently produced with titers between $10^6$ and $5 \times 10^6$ tu/ml for both vectors. Gli-36, J3T, and 293T/17 cells were infected with both vectors simultaneously at the same multiplicity of infection (MOI). Gli-36 and 293T/17 cells were infected at MOIs of 1 and 5, while J3T cells were infected at MOIs of 2 and 5 (FIG. 10). At two days post-infection, retrovirus titers in the medium were $1.6 \times 10^4 \pm 9.3 \times 10^3$ (MOI 1) and $2.2 \times 10^4 \pm 1.3 \times 10^4$ tu/ml (MOI 5) for Gli-36 cells (FIG. 10—1, 2), and 273+49 (MOI 1) and $3.4 \times 10^3 \pm 3.2 \times 10^3$ tu/ml (MOI 5) for 293T/17 cells (FIG. 10—11, 12). For J3T cells infected at MOI of 2 and 5, retrovirus titers were $4.9 \times 10^3 \pm 3.6 \times 10^3$ and $3.3 \times 10^3 \pm 2.8 \times 10^3$ tu/ml, respectively (FIG. 10—5, 8). The amplicon transduction efficiency for Gli-36 cells infected at MOI of 1 and 5, was 82 and 100%, while for J3T cells infected at MOI of 1 and 5, that was 33 and 85%, respectively, as evaluated by the percentage of lacZ positive cells (blue cells after X-gal staining) at 48 hours post-infection. Infected cells were selected in medium containing puromycin and G418, and retrovirus titers were again at 30 and 55 days post-infection for non-clonal populations (FIG. 10). For Gli-36 cells infected at MOI of 1, no drug-resistant population was observed, while for MOI of 5, retrovirus titers at 30 and 55 days post-infection were $1.2 \times 10^5 \pm 2.7 \times 10^4$ and $4.9 \times 10^4 \pm 1.2 \times 10^4$ tu/ml, respectively (FIG. 10—3, 4). J3T cells infected at MOI of 2, produced retrovirus titers of $3.8 \times 10^3 \pm 2.4 \times 10^3$ and 187±50 tu/ml, at 30 and 55 days post-infection, respectively (FIG. 10—6, 7), while for MOI of 5, titers were $3.1 \times 10^3 \pm 2.8 \times 10^3$ and $7.1 \times 10^3 \pm 5.8 \times 10^3$ tu/ml for the same timepoints (FIG. 10—9, 10).

Generation of stable retrovirus producer cells lines by a double vector-double step strategy. Several studies have shown that retention of the 0.4 kb gag gene region adjacent to the retrovirus packaging signal in retrovirus vectors, increases packaging efficiency by 10-fold (Bender, M. A., et al., *J. Virol.* 61:1639–1646 (1987); Morgenstern, J. P., and Land. H., *Nucleic Acids Res.* 18:3587–3596 (1990)). Therefore, for this alternative approach of generating stable packaging cell lines, Gli-36 and J3T cells were first infected with two retrovirus vectors, BabelacZ (gag[+]) and HSHyBPlacZ #2.2 (gag[−]), packaged in 293T/17 cells by co-transfection with pcDNA3.1MOV Ampho. After infection, cells were selected in puromycin and non-clonal resistant populations were generated (Gli-36BabelacZ, J3TBabelacZ, Gli-36HSHyBPlacZ, and J3THSHyBPlacZ). X-gal staining of these populations showed that all cells were lacZ positive. Retrovirus modified Gli-36 and J3T cell populations were then infected with HyRMOV Ampho amplicon at MOI at 1 and 5 and MOI of 2 and 5, respectively (FIG. 11).

At two days post amplicon infection, retrovirus titers in the supernatants were: $3.5 \times 10^4 \pm 1.4 \times 10^4$ (MOI 1) and $1.3 \times 10^5 \pm 2.1 \times 10^4$ tu/ml (MOI 5) for Gli-36BabelacZ cells (FIG.

11—1,3); $3.5 \times 10^4 \pm 1.1 \times 10^4$ (MOI 1) and $4 \times 10^4 \pm 1.3 \times 10^4$ tu/ml (MOI 5) for J3TBabelacZ cells (FIG. 11—5, 7); $1.6 \times 10^4 \pm 9.5 \times 10^3$ (MOI 1) and $5.1 \times 10^4 \pm 1.4 \times 10^4$ tu/ml (MOI 5) for Gli-36 HSHyBPlacZ (FIG. 11—9, 11); $1.6 \times 10^4 \pm 6.8 \times 10^3$ (MOI 2) and $1.4 \times 10^4 \pm 4.4 \times 10^3$ tu/ml (MOI 5) for J3THSHyBPlacZ cells (FIG. 11—13, 15).

These cell populations were also mock infected and infected with HyRGFP amplicon at the same MOIs and the supernatants were used two days later to infect NIH3T3 cells. No lacZ positive cells were ever observed for any of these two controls. Populations infected with HyRMOV Ampho were selected in the presence of G418. At 86 days post-infection, retrovirus titers were determined again. For Gli-36 BabelacZ cells infected at MOI of 1, it was not possible to generate a G418 resistant population. For all other cells and MOIs at the same timepoint, retrovirus titers were: $2.2 \times 10^5 \pm 4.9 \times 10^4$ tu/ml (MOI 5) for Gli-36BabelacZ (FIG. 11—4); $2.5 \times 10^5 \pm 4.9 \times 10^4$ (MOI 2) and $5.1 \times 10^5 \pm 3.3 \times 10^4$ tu/ml (MOI 5) for J3TBabelacZ (FIG. 11—6,8); $1.3 \times 10^5 \pm 3.3 \times 10^4$ (MOI 1) and $2.0 \times 10^5 \pm 2 \times 10^4$ tu/ml (MOI 5) for Gli-36 HSHyBPlacZ (FIG. 11—10,12); and $2 \times 10^5 \pm 5.4 \times 10^4$ (MOI 2) and $2.5 \times 10^5 \pm 4.8 \times 10^4$ tu/ml (MOI 5) for J3THSHyBPlacZ (FIG. 11—14, 16).

At day 100 post-infection, retrovirus titers were determined again and found to be similar to the titers obtained at day 86. As a comparison, retrovirus titers produced by an established packaging cell line, ψCRIPlacZ (Danos, O., and Mulligan, R. C., *Proc. Natl. Acad. Sci. USA* 85:6460–6464 (1988)), were determined using the same culture conditions and found to be $4.5 \times 10^5 \pm 6.7 \times 10^4$ tu/ml (FIG. 11—17). The efficiency of retrovirus vector production was evaluated by calculating the average number of retrovirus transducing units produced per cell. This ratio was determined to be 0.29 to 0.64 for Gli-36 derived packaging cells, 0.57 to 1.36 for J3T derived packaging cells, and 2.1 for ψCRIPlacZ cells (Table 3).

TABLE 3

Efficiency of retrovirus vector production by different stable retrovirus packaging cell lines

| Cell line[a] | MOI | R ± SD[b] |
|---|---|---|
| Gli-36BabelacZ | 5 | 0.64 ± 0.16 |
| J3TBabelacZ | 2 | 0.84 ± 0.17 |
| J3TBabelacZ | 5 | 1.36 ± 0.29 |
| Gli-36HSHyBPlacZ | 1 | 0.31 ± 0.08 |
| Gli-36HSHyBPlacZ | 5 | 0.29 ± 0.09 |
| J3THSHyBPlacZ | 2 | 0.57 ± 0.14 |
| J3THSHyBPlacZ | 5 | 1.11 ± 0.22 |
| ψCRIPlacZ | — | 2.1 ± 0.7 |

[a]Retrovirus producer cell lines obtained after infection with HyRMOV Ampho amplicon at different MOIs and G418 selection.
[b]R - Average number of retroviral transducing units produced per cell.
Abbreviations: SD—standard deviation Expression of retrovirus proteins in stable packaging cell lines. The previous parameter suggests that glioma-derived stable retrovirus packaging cell lines originated in this study were 2 to 4-fold less efficient thatn ψCRIP cells in producing retrovirus vectors. To elucidate the origin of this difference, expression of retrovirus proteins in these cells was analyzed by western blot, using antibodies that recognize MoMLV p30(CA) (capsid protein) and gp70(SU) (surface envelope protein) (FIGS. 12 A and B). $Pr200^{gag/pol}$ and $Pr65^{gag}$ precursor polyproteins were present in all cell lines as well as p30(CA) (FIG. 12A). Another band was present between 46 and 66 KD, which could be the result of premature proteolytic processing of $Pr65^{gag}$ with cleavage of p15(MA) (matrix) or p10(NC) (nucleocapsid) proteins from the polyprotein (arrow in FIG. 12A). Densitometric analysis of the films showed that expression levels of precursor polyproteins, $Pr200^{gag/pol}$ and $Pr65^{gag}$, in J3T derived packaging cells (FIG. 12A, lanes 4, 6–9) were 10 and 1.7-fold higher, respectively, than in Gli-36 derived packaging cells (FIGS. 12A, lanes 5, 10–12). Expression of gp70(SU) was 2-fold higher in J3T derived cell lines (FIGS. 12B, lanes 4, 6–9) when compared to Gli-36 derived packaging cells (FIGS. 12B, lanes 5, 10–12). The extra band present on the blot (asterisk in FIG. 12B) could be a non-glycosylated form of gp70(SU) protein. Despite the large difference in retrovirus titers (10 to 100-fold) (FIGS. 10 and 11), no significant difference in expression of retroviral proteins was observed between the two methods of generating stable packaging cell lines: simultaneous infection with both amplicon vectors (FIGS. 12A and B, lanes 4 and 5) or double vector-double step strategy (FIGS. 12A and B, lanes 6–12). Expression of retrovirus proteins, $Pr65^{gag}$ and gp70(SU), Gli-36 and J3T derived packaging cell lines was 2 to 4-fold and 18 to 36-fold higher than in ψCRIPlacZ cells (FIG. 12A and B, lane 3), respectively.

Levels of packageable vector RNA. This was evaluated by northern blot analysis of total RNA using part of the lacZ gene (C-terminal 1.2 kb—FIG. 8B) as a probe (FIG. 13B). Densitometric analysis of the film (FIG. 13B) showed that all cell lines expressed levels of packageable vector RNA between 1.6 and 18% of that in ψCRIPlacZ cells, with the exception of BabelacZ retrovirus modified Gli-36 derived packaging cell line (FIG. 13B, lane 10), which expressed 62% (FIG. 13C—relative densities). All cell lines modified with the HSHyBPlacZ retrovirus vector or hybrid amplicon showed a band (lanes 3, 4, 8, 9, 11, 12) that was smaller than that observed for BabelacZ modified cells (lanes 6, 7, 10) as expected, since the former vector had the gag gene region deleted from the retrovirus packaging signal (see material and methods).

Discussion

The development and characterization of a second hybrid amplicon vector system capable of single step conversion of cells to retrovirus vector producer cells is described in this Example. Transduction of several cell types with this vector system resulted in the efficient production of retrovirus vectors. For the same cell line, retrovirus titers were dependent on the extent of amplicon transduction, but different cell lines displayed different capacities for retrovirus production. Infection of a population of dividing cells with this system results in continuing increase in transgene activity until a stable, steady state level is reached.

Several vector systems have been developed which can induce cells to transiently produce replication-deficient retrovirus vectors after transduction. Some systems use transfection to introduce components of the vector system into cells (Li, K. J. and H. Garoff, *Proc. Natl. Acad. Sci. USA* 93:11658–11663 (1996); Naviaux, R. K., et al., *J. Virol.* 70:5701–5705 (1996); Noguiez-Hellin, P., et al., *Proc. Natl. Acad. Sci. USA* 93:4175–4180 (1996)). This process is efficient in culture, but inefficient in vivo.

Others have used combinations of viral vectors to achieve the same result. In a two step approach, cells are first infected with a retrovirus vector and then with an HSV amplicon vector coding for the gag-pol and env genes (Savard, N., et al., *J. Virol.* 71:4111–4117 (1997)), or with an adenovirus vector carrying these genes in the same (Lin, X., *Gene Ther.* 5:1251–1258 (1998)); or separate vectors (Id.);

Yoshida, Y., *Biochem. Biophys. Res. Comm.* 232:379–382 (1997)). Retrovirus genes and vector element can both be delivered by adenoviral vectors (Duisit, G., et al., *Human Gene Ther.* 10:189–200 (1999); Feng, M., et al., *Nature Biotech.* 15:866–870 (1997)). Some of these adenovirus based systems can generate relatively high retrovirus titers ($10^5$–$10^6$ cfu/ml) in cultured cells (Duisit, G., et al., *Human Gene Ther.* 10:189–200 (1999); Yoshida, Y., *Biochem. Biophys. Res. Comm.* 232:379–382 (1997)). Although systems that employ different vectors to deliver the elements necessary for retrovirus production have a low potential to generate replication competent retroviruses (RCR), output titers depend on the efficiency of co-transduction. The more different vectors that are needed, the lower the probability that all will infect the same cell to allow retrovirus vector production.

Adenovirus vectors can be produced at very high titers (>$10^{10}$ pfu/ml) and can achieve remarkable gene transfer efficiencies in some circumstances in vivo. However, in some applications, such as gene transfer to malignant human gliomas, their transduction efficiency has been reported to be only 30–35% in certain areas, with an overall efficiency below 11% (Puumalainen, A. M., et al., *Human Gene Ther.* 9:1769–1774 (1998)). At this level of transduction, the probability that 2 or 3 vectors will infect the same cell is low, and therefore the ability to convert cells in situ into retrovirus packaging cells would be compromised. However, Feng et al. demonstrated that in a tumor model in vivo, a retrovirus production system based on two adenoviral vectors was capable of increasing transgene retention as compared to a conventional adenovirus vector (Feng, M., et al., *Nature Biotech.* 15:866–870 (1997)). The present invention demonstrates that the principle can work, but conceptually the process should be more efficient if a single adenovirus vector contained all necessary elements to generate retrovirus vectors. Although the size limitation of conventional adenovirus vectors precludes the construction of such vector, "gutless" adenovirus vectors could easily accommodate all the components.

The hybrid amplicon vector system described in this Example has several advantages over existing vector systems for generating retroviral vectors: (1) all elements necessary for production of replication-deficient retrovirus vectors are present or can be placed in the same construct. In theory, the conversion efficiency per transduced cell is 100%, independently of whether amplicon DNA is introduced into cells by transfection or infection; (2) not only do HSV virions have a wide host range, stability and high infectability, but due to their large DNA capacity and the mode of viral DNA replication, each amplicon vector carries multiple copies of the amplicon plasmid. This means that for each transduction event, multiple copies of the transgenes are delivered to the cell nucleus. This may account for the high retroviral titers obtained with this system; (3) presence of the EBV elements, oriP and the EBNA-1 gene, which mediate episomal replication and retention of amplicon DNA in dividing cells, increases the duration of retrovirus production; and (4) HSV amplicons have a large transgene capacity (theoretically up to 150 kb) which will allow the inclusion of other elements to improve the efficiency of retrovirus vector production.

The mode of retention contributed by the AAV elements (the ITRs and rep gene) is complex and cell type dependent, as it is for AAV vectors. The retention process itself can occur through replicative amplification of the ITR-flanked sequences, thus creating hundreds to thousands of copies in the cell nucleus, or by integration via a circularized intermediate either randomly or site-specifically in human chromosome 19q13.3 (Duan, D., et al., *J. Virol* 73:161–169 (1999); Flotte, T. R. and B. J. Carter, *Gene Therapy* 2:357–362 (1995)). These retention properties occur to different extents in different cell types as a function of species of origin and state of cell, including dividing/non-dividing state (Russell, D. W., et al., *Proc. Natl. Acad. Sci. USA* 91:8915–8919 (1994)); treatment by heat shock, irradiation or genotoxic agents, infection with viruses, including adenovirus and HSV (Duan, D., et al., *J Virol* 73:161–169 (1999); Ni, T. H., et al., *J Virol* 72:2777–2787 (1998); Muzyczka, N., *Curr Top Microbiol Immunol* 158:97–129 (1992); Schlehofer, J. R., et al., *Virology* 152:110–117 (1986)) and state of protein phosphorylation (Mah, C., et al., *J Virol* 72:9835–9843 (1998)). Some of these properties may, in turn, affect the ability of these cells to produce retrovirus vectors in this tribrid system.

The efficiency of gene delivery and the level of retrovirus titers mediated by this hybrid amplicon vector system is dependent on a number of factors, that were discussed in detail in the Discussion section of Example 1. These factors include infectability with HSV and retrovirus virions, capacity to produce retrovirus vectors, and retention of amplicon elements. Infectability of target cells by HSV virions is a primary determinant of the levels of retrovirus vectors produced by a cell population, while the transduction efficiency by retrovirus vectors is ultimately responsible for long term transgene retention. It is believed that the same factors affecting retrovirus titers in the HSV/EBV/retrovirus system (Example 1) may have a role in the HSV/AAV/retrovirus sytem.

The remarkable feature of the HSV/AAV/RV packaging system is that following infection with the amplicon vectors, stable, packaging cell lines were generated, which produced high titer retrovirus vectors without being maintained on drug selection for both J4T and Gli36 cells. This occurred for up to 100 days after infection with continuous division of cells, thus, supporting a mechanism of genomic intergration. This feature should allow generation of stable packaging cell lines in culture, as well as in vivo following a single infection with the amplicon vector. Assuming immune rejection of the packaging cells can be avoided by temporary repression of expression of gag-pol-env genes or by other means of inhibition of immune recognition, these cells should have an extended timespan of retrovirus vector gene delivery in vivo. Ultimately, this will allow them a longer time period to migrate or home to target cells/tissue and allow for generation of more vectors (titer/24 hrs×length of survival of cells), and thus retrovirus infection of more endogenous cells. This would be especially important for widespread targets, numerous cell targets, or slowly dividing cell targets.

This tribrid vector system provides a means to stably deliver a transgene to a large percentage of cells in a dividing population starting with transduction of a small percentage of cells.

The first genotype, amplicon-transduced cells, express GFP and lacZ encoded by the episomal amplicon, and produce retrovirus vectors carrying the lacZ gene, while at the same time they are themselves resistant to infection by those same retrovirus vectors due to the presence of the envelope proteins on the cell surface (Coffin, J. M., in B. N. Fields et al., (ed.) *Fields Virology*, Raven Publishers, Philadelphia (1996)).

The second genotype, represents uninfected cells which do not express any transgenes, but are susceptible to infection by retrovirus vectors produced by amplicon-transduced cells. With time, a third cell type appears in the population which expresses lacZ from retrovirus vector sequences stably integrated in their genome, and is receptive to multiple retroviral infections. The extent of loss of the HSV/AAV amplicon elements will vary from cell to cell, but in general, some portion of the amplicon infected cells will stably retain the packaging elements and continue to produce retrovirus vectors and resist infection by them for long to indefinite periods; another portion will lose the amplicon sequences and thus stop making retrovirus vectors, but become infectable by them. Cells which lose the amplicon also lose expression of lacZ and retroviral proteins but become susceptible to retroviral infection, depending on the half-life of gp70 on the cell surface.

The third cell type becomes more prominent with time, until it is the sole contributor to lacZ activity in the population, and essentially no more retrovirus vectors are produced. Total lacZ activity in the population at any time is the sum of lacZ expressed from the amplicon sequences and from the retrovirus vectors stably integrated in the cell genome (1 copy/infection×number of infections). Absolute levels of lacZ activity will depend on the relative activity of the LTR promoter in the context of the episome integrated sequences or at different sites of integration in different cell types.

The behavior of cell populations in accumulating transgene activity could be described by the model depicted in FIG. 7. At low initial levels of amplicon transduction, the number of transduced cells and levels of lacZ activity are low in the early post infection period. At the same time, there is a large pool of cells which are susceptible to retrovirus infection and hence able to achieve stable lacZ activity. In contrast, at high initial levels of transduction, lacZ activity is high in the early period post-infection but the percentage of retrovirus infectable cells is small and increases only as retrovirus titers are declining, thus achieving only a modest increase in lacZ activity. Cells that have lost their ability to produce retrovirus might still not be susceptible to retrovirus infection due to the continuing presence of envelope protein on the cell surface. This model would explain why lowering the percentage of amplicon transduced cells (lower MOIs) results in a higher increase in lacZ activity in the population over time.

The triple hybrid gene delivery system of the present invention could be used in vivo to directly modify specific cell populations, which by their position, migratory or tissue/organ targeting properties, could secondarily deliver retrovirus vectors to progenitor/stem cells or to a larger population of dividing cells, resulting in expanded spatial distribution of transgene expression. Several applications for this gene delivery amplification mechanism include tumor therapy and genetic modification of the developing central nervous system, hematopoietic system, lung epithelium, and other proliferating cell populations. Although the more extensive use of this gene delivery amplification mechanism in the adult is limited by the fact that the retrovirus components in this tribrid system are derived from MoMLV, which can only infect dividing cells, this could be surpassed by replacing those components with lentivirus elements, thus allowing for production of retroviral vectors that can infect both dividing and non-dividing cells.

The vector system of the invention may also be used for two modalities of therapeutic gene delivery to tumors. In one mode, the retrovirus producer cells would be derived from the tumor cells themselves and thus presumably share the same growth and migratory patterns; in the other mode, normal cells with migratory or tumor targeting properties could be used as gene delivery vehicles, e.g., neuronal progenitor cells (Aboody-Guterman, K. S., "Neural stem cells migrate throughout and express foreign genes within experimental gliomas—a potential gene therapy approach to brain tumors" (submitted for publication, 1999), endothelial cells (Lal, B., et al., *Proc. Natl. Acad. Sci. USA* 91:9695–9699 (1994)), and tumor infiltrating lymphocytes (Kasid, A., et al., *Proc. Natl. Acad. Sci. USA* 87:473–477 (1990)). Several studies have shown that packaging cell lines currently in use, which are derived from mouse fibroblasts, do not display migratory properties in the context of brain tumors (Ram, Z., et al., *Nature Med.* 3:1354–1361 (1997); Tamiya, T., et al., *Gene Ther.* 2:531–538 (1995); Tamura, M., et al., *Human Gene Ther.* 8:381–391 (1997)). This presents several restrictions to effective gene delivery. The packaging cells tend to form clusters around the injection site, and given the limited diffusion of retroviruses through cell layers, only those packaging cells close to the cluster surface release retrovirus vectors which can infect tumor cells. As a result, the number of vector particles that reach tumor cells is much lower than what would be expected from the number of packaging cells implanted. Furthermore, these retrovirus vectors have a relatively short half-life and can only infect dividing cells. In experimental brain tumor models, which have high mitotic indexes, these small 'clusters' of gene delivery can be effective in therapeutic strategies. However, in human glioblastomas (GBM), where it is estimated that only 1–8% of the cells are actively dividing (Yoshii, Y., et al., *J. Neurosurg.* 65:659–663 (1986)), the probability of a packaging cell being close to a dividing cell is extremely low. Furthermore, one of the major challenges for therapy of human GBM is the invasive nature of these cells, which migrate extensively along a limited number of routes in the CNS (Pederson, P. -H., et al., *Cancer Res.* 53:5158–5165 (1993); Yamada, M., et al., *J. Neurosci. Res.* 38:415–423 (1994)). Tamura et al. have shown that if the same type of glioma cells are implanted in the tumor mass, they tend to migrate along the same routes as the initial tumor cells and eventually reach them (Tamura, M., et al., *Human Gene Ther.* 8:381–391 (1997)). Using tumor cells themselves as retrovirus producers could possibly bypass the current restrictions to gene delivery by retrovirus vectors by spreading vector production over larger areas.

Although some tissues, like the CNS, are relatively immune privileged sites, an immune response to expressed retroviral proteins or transgene products would limit the survival of amplicon-derived packaging cells. Examples of ways to reduce the immune response would be to incorporate in the amplicon certain immune-modulatory molecules, such as those that tumors use to evade the immune system, e.g., CD95 ligand, transforming growth factor-$\beta$, interleukin-10 (Hahne, M., et al., *Science* 274:1363–1366 (1996)). The main advantage of this triple hybrid amplicon gene delivery system is that it should mediate retrovirus vector production in situ after direct injection of amplicon vector stocks into the tumor mass, without the need for any tissue culture manipulation or implantation of exogenous cells.

This transgene delivery amplification mechanism could also be used to expand the range of gene delivery in the developing CNS. Several studies performed with replication competent retrovirus vectors during development have shown that transgenes can be delivered to a large number of cells throughout the entire CNS (Fekete, D. M. and C. L. Cepko, *Mol. Cell Biol.* 13:2604–2613 (1993)). However, RCRs carry with them not only the transgene of interest but also a high risk of insertional oncogenesis. The triple hybrid system of the present invention could be used in a similar, but safer, manner to achieve widespread gene delivery in the CNS. Genetic modification of cells in the subventricular zone would create two amplifying effects: first, production of retrovirus vector in that area could result in genetic modification of neuronal progenitors that would later migrate out into the brain and differentiate into neurons. Second, amplicon-transduced cells could themselves migrate to other regions of the brain where they can come in close contact with populations of dividing glia during gliogenesis. Such spatial expansion mechanisms would be useful for gene delivery in disease states where the entire CNS is involved and can be corrected by diffusible factors, as is the case for some lysosomal storage disorders.

This same principle can be used for genetic modification of the hematopoietic system. This could be achieved by transducing CD34-positive cells in culture followed by re-implantation and migration of these cells to the bone marrow where they would come in close contact with dividing hematopoietic stem cells. Alternatively, similar to what was attempted with fibroblast-derived packaging cells (Nelson, D. M., et al., *Human Gene Ther.* 8:747–754 (1997)), the amplicon vector could be directly injected into the bone marrow. These strategies could be used for gene delivery to normal bone marrow, and also in the context of leukemia. Since bone marrow stem cells divide very slowly, it is possible that retrovirus vectors produced in situ would preferentially infect leukemic cells. As a safety mechanism, cells could be transduced with prodrug activating enzymes that result in the production of metabolites whose cytotoxic effects are cell cycle dependent, such as the HSV-tk/ ganciclovir system.

The principle of the primary producer cells being in close proximity to secondary target cells might also prove useful to attain stable gene delivery to the lung. Adenovirus vectors and liposomes are capable of transducing the lung epithelium with varying degrees of efficiency. Due to the non-integrative nature of these delivery modalities and the turn-over of cells in the lung epithelium, these strategies only achieve transient expression of transgenes. Repeated administration of some of these agents results in strong inflammatory immune responses. An alternative approach using integrating vectors, such as lentivirus vectors (Goldman, M. J., et al., *Human Gene Ther.* 8:2261–2268 (1997)), would also require repeated administration of the viral vector due to turnover of transduced cells. Since 95% of the epithelial surface is occupied by type I pneumocytes (terminally differentiated) and only 3% by type II pneumocytes (stem cells), direct vector will most likely transduce type I cells. Furthermore, in some disease states, such as cystic fibrosis, the rate of replacement seems to be accelerated (Leigh, M. W., et al., *Am. J. Resp. Cell Mol. Biol.* 12:605–612 (1995)). Since type I cells are derived from type II cells, the latter dividing cells are the appropriate targets to achieve stable genetic modification of the lung epithelium. In theory, infection of the lung epithelium with the amplicons of the invention should convert type I cells into retrovirus producer cells, which can deliver vectors to type II cells in the vicinity when they divide and they, in turn, would give rise to genetically modified type I cells.

This novel triple hybrid amplicon delivery system provides a means to extend retrovirus gene delivery to larger numbers of cells over a wider distribution in the body, as compared to current retrovirus producer cells. It also potentially allows the direct conversion of endogenous cells to packaging cells and thus should have wide application in methods of gene therapy.

EXAMPLE 3

Other Versions of the Triple Hybrid Amplicon Vector

FIG. 14 is a graph depicting the effect of Epstein-Barr virus elements on the duration of retrovirus vector production by tumor cells. Human Gli-36 glioma cells (triangles) and J3T dog glioma cells (circles) were infected at MOI of 2 with the HSV/EBV/Retrovirus tribrid amplicon (B7; closed triangle and circle) and an HSV amplicon with identical structure but missing the EBV oriP and EBNA-1 gene (HRA; open triangle and circle). Retrovirus production was analyzed over a period of 8 days. Titers were normalized for vector titers at 3 days post-infection FIG. 15 depicts the structure of "HERAC" vectors. The retrovirus vector component was modified by replacing the 5' LTR with a CMV-LTR hybrid promoter. This modified retrovirus vector was inserted in the HER backbone in two different orientations (K16 and K19).

FIG. 16 depicts the structure of "BiHERA" vectors. Expression of the retrovirus structural genes and vector element were placed under the control of a bidirectional CMV promoter. This cassette was cloned in the HSV/EBV amplicon backbone in two different orientations (Clones Q4 and Q8).

FIG. 17 is a bar graph depicting the relative retrovirus vector titers for new versions of the HERA tribrid vector. The retrovirus component of the HERA vector (B7) was modified to incorporate a hybrid CMV-LTR promoter at the 5'-end, and inserted in the HER backbone in two different orientations (HERAC K16, K19). A bidirectional cassette designed for expression of the retrovirus structural genes and vector component from the same promoter was also inserted in two directions in the hybrid HSV/EBV amplicon (BiHERA Q4, Q8). Retrovirus titers were determined at 48 hours post-transfection of 293T/17 cells.

EXAMPLE 4

Infection of Human Neural Progenitor Cells with the B7 Tribrid Amplicon $5 \times 10^5$ human neural progenitor cells, H1, were infected with the tribrid amplicon B7 at a MOI of 1, 5, and 10.

The percentage of green fluorescent protein (GFP)-positive cells was measured by fluorescence-activated cell sorting (FACS) analysis at day 2 and day 7. The results in FIG. 18 show an expected loss of the amplicon DNA mediated GFP expression from cells over 5 days.

At day 2 and day 7, NIH 3T3 cells were infected with supernatant from amplicon-infected H1 cells. Forty-eight hours after infection, NIH 3T3 cells were stained with X-Gal solution and retroviral titers were determined. The results in FIG. 19 show high titer production of retrovirus vectors ($10^6$ tu/ml) by neural progenitor cells infected with the tribrid amplicon vector, decreasing over time, but still significant after 7 days ($10^5$ tu/ml) at a MOI initial amplicon infection of 10.

EXAMPLE 5

Subcutaneous Injection of Glioma Cells Infected in Culture with the Tribrid Amplicon Mixed With Non-Infected Glioma Cells in a Mouse Tumor Model Dog glioma cells (J3T1) were infected with the B7 or C1 hybrid amplicons (described above) at a MOI of 2. Twenty-four hours post-infection, the transduction efficiency was determined by FACS analysis (GFP positive cells). Subsequently B7-infected and non-infected glioma cells were mixed in a ratio of 5%/95%, 10%/90%, 20%/80% and 40%/60%. As a control, C1-infected cells were mixed with non-infected cells in a ratio of 40%/60%. Subsequently, $5\times10^6$ cells were injected subcutaneously into nude mice. The animals were sacrificed 10 days later (tumor volume ranged from 90–145 mm$^3$). Using a cryostat, the tumor was cut into 50 μm sections and stained with X-gal.

FIG. 20A is a photograph depicting tumor derived from a mixture of tribrid amplicon C1-infected J3T I cells with non-infected J3T I cells, in a ratio of 40%/60%. Only a few lacZ positive cells could be detected in the center of the tumor. The loss of transgene expression (40% to less than 10% of tumor) is expected as lacZ is carried only in the amplicon backbone, which is lost over time.

FIG. 20B is a photograph depicting tumor derived from a mixture of tribrid amplicon B7-infected J3T I cells with non-infected J3T I cells, in a ratio of 5%/95%. In contrast to the control C1 tumors (FIG. 20A), lac Z positive cells were abundant, and equally distributed throughout the tumor. Since even fewer lacZ-positive cells were initially injected here in comparison to the C1 experiment above (5%/95% vs. 40%/60%), the large number of lacZ cells observed in FIG. 20B indicated retrovirus mediated transfer of lacZ and transmission to daughter cells.

FIG. 20C is a photograph depicting tumor derived from a mixture of tribrid amplicon B7-infected J3T I cells with non-infected J3T I cells, in a ratio of 10%/90%. With the increased concentration of amplicon cells, the abundance of transgene positive cells increased dramatically. The inventors estimate that at least 50% of tumor cells are transgene positive with long-term expression.

FIG. 20D is a photograph depicting tumor derived from a mixture of B7-infected J3T I cells with non-infected J3T I cells, in a ratio of 20%/80%. When 20% of the initial tumor population bears the retrovirus-producing amplicon, virtually the whole tumor becomes positive over 10 days of growth in vivo.

FIG. 20E is a photograph depicting tumor derived from a mixture of B7-infected J3T I cells with non-infected J3T I cells, in a ratio of 40%/60%. With the increasing percentage of cells bearing the retrovirus-producing amplicon vector, successive infections with the retrovirus vectors give multiple transgene copies per cell, and hence higher levels per cell of lacZ expression. Such an increased dose per cell could lead to increased therapeutic potential of the transgene.

EXAMPLE 6

Injection of Tribrid Amplicon in Subcutaneous Gliomas in a Nude Mouse Model

In a nude mouse model, dog-derived J3T I glioma cells ($5\times10^6$ cells in 100 μl) were injected subcutaneously into the flank. After the tumor reached a size of about 100 mm$^3$, either 10 ml of B7 (Tribrid Amplicon, Titer $3.14\times10^8$ tu/ml) or 10 μl of C1 (Control Amplicon, Titer $2.18\times10^8$ tu/ml) were infused into the tumor over a 10 minute period as a single injection. The animals were sacrificed 10 days later. Using a sliding microtome, the tumors were cut into 20 mm sections and stained with X-gal.

FIG. 21A is a photograph depicting tumor injection with B7 amplicons. Numerous lacZ positive cells are concentrated around the needle tract. In comparison to the control injection with C1 (FIG. 21B), this indicated successful secondary retroviral infection of tumor cells.

FIG. 21B is a photograph depicting tumor injection with the control C1 amplicons. Only a few lacZ positive cells are visible around the needle tract.

Although the foregoing invention has been described in some detail by way of illustration and example for purposes of clarity of understanding, this invention is not limited to the particular embodiments disclosed, but is intended to cover all changes and modifications that are within the spirit and scope of the invention as defined by the appended claims.

All publications and patents mentioned in this specification are indicative of the level of skill of those skilled in the art to which this invention pertains. All publications and patents are herein incorporated by reference to the same extent as if each individual publication or patent application were specifically and individually indicated to be incorporated by reference.

What is claimed is:

1. A hybrid amplicon vector comprising:
   (a) an HSV origin of replication (ori S);
   (b) an HSV packaging signal (pac);
   (c) an EBV origin of replication (ori P);
   (d) an expression cassette of the EBNA-1 protein of EBV;
   (e) gag, pol, and env genes of a retrovirus; and
   (f) retroviral vector sequences, containing at least one transgene of interest;
      wherein said hybrid amplicon vector is capable of converting dividing or non-dividing cells into retroviral packaging cells in a single transduction.

2. The hybrid amplicon vector of claim 1, wherein the retrovirus elements (e) and (f) are from lentivirus.

3. The hybrid amplicon vector of claim 1, wherein the cells are mammalian cells.

4. An isolated host cell transformed with the hybrid amplicon vector of claim 1.

5. A method for expressing at least one transgene in a cell, in vitro, comprising:
   (a) introducing the HSV/EBV/retrovirus hybrid amplicon vector of claim 1 into the cell; and
   (b) expressing at least one transgene in the cell.

6. The method of claim 5, wherein said cell is a proliferating cell.

7. The method of claim 5, wherein said transgene is a therapeutic gene, a reporter gene, or a selectable marker gene.

8. The method of claim 7, wherein said transgene is a therapeutic gene.

9. The method of claim 7, wherein said transgene is a reporter gene or a selectable marker gene.

10. The hybrid amplicon vector of claim 1, wherein the retrovirus elements (e) and (f) are from MoMLV and the cells are dividing cells.

11. A method for selectively killing neoplastic cells comprising:
    (a) infecting said neoplastic cells intratumorally with the hybrid amplicon vector of claim 1, wherein said transgene of interest in step (f) of claim 1 comprises a polynucleotide sequence encoding HSV thymidine kinase (TK), wherein said TK renders said tumor cells sensitive to ganciclovir or acyclovir;
    (b) administering an effective amount of ganciclovir or acyclovir sufficient to kill said neoplastic cells; and
    (c) selectively killing said neoplastic cells.

12. The method of claim 11, wherein said hybrid amplicon vector further comprises a polynucleotide sequence encoding bacterial cytosine deaminase (CD) and wherein an effective amount of 5-fluorocytosine (5-FC) is administered sufficient to kill said neoplastic cells.

13. A method for selectively killing neoplastic cells comprising:
    (a) infecting said neoplastic cells intratumorally with the hybrid amplicon vector of claim 1, wherein said transgene of interest in step (f) of claim 1 comprises a polynucleotide sequence encoding cytochrome P450, wherein said cytochrome P450 renders said tumor cells sensitive to cyclophosphamide or ifosphamide;
    (b) administering an effective amount of cyclophosphamide or ifosphamide sufficient to kill said neoplastic cells; and
    (c) selectively killing said neoplastic cells.

14. The method of claim 13, wherein said hybrid amplicon vector further comprises a polynucleotide sequence encoding HSV thymidine kinase, and wherein an effective amount ganciclovir or acyclovir is administered sufficient to kill said neoplastic cells.

15. A hybrid amplicon vector comprising:
    (a) an HSV origin of replication (ori S);
    (b) an HSV packaging signal (pac);
    (c) an AAV rep gene;
    (d) AAV ITR elements;
    (e) gag, pol, and env genes of a retrovirus; and
    (f) retroviral vector sequences, containing at least one transgene of interest;
       wherein said hybrid amplicon vector is capable of converting dividing or non-dividing cells into retroviral packaging cells in one or two transductions.

16. The hybrid amplicon vector of claim 15, wherein the retrovirus elements (e) and (f) are from lentivirus.

17. The hybrid amplicon vector of claim 15, wherein the cells are mammalian cells.

18. An isolated host cell transformed with the hybrid amplicon vector of claim 15.

19. A method for expressing at least one transgene in a cell, in vitro, comprising:
    (a) introducing the HSV/AAV/retrovirus hybrid amplicon vector of claim 15 into the cell; and
    (b) expressing at least one transgene in the cell.

20. The method of claim 19, wherein said cell is a proliferating cell.

21. The method of claim 19, wherein said transgene is a therapeutic gene, a reporter gene, or a selectable marker gene.

22. The method of claim 21, wherein said transgene is a therapeutic gene.

23. The method of claim 21, wherein said transgene is a reporter gene or a selectable marker gene.

24. A method for selectively killing neoplastic cells comprising:
    (a) infecting said neoplastic cells intratumorally with the hybrid amplicon vector of claim 15, wherein said transgene of interest in step (f) of claim 15 comprises a polynucleotide sequence encoding HSV thymidine kinase (TK), wherein said TK renders said tumor cells sensitive to ganciclovir or acyclovir;
    (b) administering an effective amount of ganciclovir or acyclovir sufficient to kill said neoplastic cells; and
    (c) selectively killing said neoplastic cells.

25. The method of claim 24, wherein said hybrid amplicon vector further comprises a polynucleotide sequence encoding bacterial cytosine deaminase (CD) and wherein an effective amount of 5-fluorocytosine (5-FC) is administered sufficient to kill said neoplastic cells.

26. A method for selectively killing neoplastic cells comprising:
    (a) infecting said neoplastic cells intratumorally with the hybrid amplicon vector of claim 15, wherein said transgene of interest in step (f) of claim 15 comprises a polynucleotide sequence encoding cytochrome P450, wherein said cytochrome P450 renders said tumor cells sensitive to cyclophosphamide or ifosphamide;
    (b) administering an effective amount of cyclophosphamide or ifosphamide sufficient to kill said neoplastic cells; and
    (c) selectively killing said neoplastic cells.

27. The method of claim 26, wherein said hybrid amplicon vector further comprises a polynucleotide sequence encoding HSV thymidine kinase, and wherein an effective amount ganciclovir or acyclovir is administered sufficient to kill said neoplastic cells.

28. A method for expressing at least one reporter gene or selectable marker gene in a cell, in vivo, comprising:
   (a) introducing the HSV/EBV/retrovirus hybrid amplicon vector of claim 1 into the cell; and
   (b) expressing at least one reporter gene or selectable marker gene in said cell.

29. A method for expressing at least one reporter gene or selectable marker gene in a cell, in vivo, comprising:
   (a) introducing the HSV/AAV/retrovirus hybrid amplicon vector of claim 15, into the cell; and
   (b) expressing at least one reporter gene or selectable marker gene in said cell.

30. The hybrid amplicon vector of claim 15, wherein the retrovirus elements (e) and (f) are from MoMLV and the cells are dividing cells.

* * * * *

SEQUENCE LISTING

<160> NUMBER OF SEQ ID NOS: 8

<210> SEQ ID NO 1
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 1
gctagccctc ttgcagttgc atccgac                                27

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 2
aggagcaact ggcgatagtg gac        23

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 3
tctagactat ggctcgtact c        21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 4
ctgtttaaca gatccccttg g        21

<210> SEQ ID NO 5
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 5
gcggccgctg atcattccgc gcacatttcc ccgaaaag        38

<210> SEQ ID NO 6
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 6
gtcgacagat ctcagcagac aagacgcgcg gcttcgg        37

<210> SEQ ID NO 7
<211> LENGTH: 41
<212> TYPE: DNA
<213> ORGANISM: Artificial Sequence
<220> FEATURE:
<223> OTHER INFORMATION: Description of Artificial Sequence: Primer

<400> SEQUENCE: 7
atgcatgcgg ccgctgatca aaatgaaaga cccccgctga c        41

<210> SEQ ID NO 8
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 8
atcgatgtcg acattaatgt ctccagaaaa aggggggaat gaaag        45